United States Patent
Prockop et al.

(10) Patent No.: US 9,062,103 B2
(45) Date of Patent: Jun. 23, 2015

(54) ADULT STEM CELLS/PROGENITOR CELLS AND STEM CELL PROTEINS FOR TREATMENT OF EYE INJURIES AND DISEASES

(71) Applicants: Darwin J. Prockop, Philadelphia, PA (US); Joo Youn Oh, Temple, TX (US); Barry Berkowitz, Framingham, MA (US); Gavin W. Roddy, Rochester, MN (US); Robert Rosa, Holland, TX (US)

(72) Inventors: Darwin J. Prockop, Philadelphia, PA (US); Joo Youn Oh, Temple, TX (US); Barry Berkowitz, Framingham, MA (US); Gavin W. Roddy, Rochester, MN (US); Robert Rosa, Holland, TX (US)

(73) Assignees: The Texas A&M University System, College Station, TX (US); Temple Therapeutics, Inc., Framingham, MA (US); Scott & White Healthcare, Temple, TX (US)

( * ) Notice: Subject to any disclaimer, the term of this patent is extended or adjusted under 35 U.S.C. 154(b) by 0 days.

(21) Appl. No.: 14/250,807

(22) Filed: Apr. 11, 2014

(65) Prior Publication Data
US 2014/0308295 A1   Oct. 16, 2014

Related U.S. Application Data

(62) Division of application No. 13/643,592, filed as application No. PCT/US2011/000771 on May 3, 2011, now Pat. No. 8,785,395.

(60) Provisional application No. 61/464,172, filed on Feb. 28, 2011, provisional application No. 61/330,735, filed on May 3, 2010.

(51) Int. Cl.
| | |
|---|---|
| *A61K 38/00* | (2006.01) |
| *A61P 27/02* | (2006.01) |
| *C07K 16/18* | (2006.01) |
| *A61K 9/00* | (2006.01) |
| *A61K 35/28* | (2015.01) |
| *C12N 5/0775* | (2010.01) |
| *A61K 35/12* | (2015.01) |

(52) U.S. Cl.
CPC ............. *C07K 16/18* (2013.01); *A61K 9/0048* (2013.01); *A61K 9/0051* (2013.01); *A61K 35/28* (2013.01); *A61K 2035/124* (2013.01); *C12N 5/0663* (2013.01); *C12N 2501/48* (2013.01); *C12N 2501/25* (2013.01)

(58) Field of Classification Search
CPC ........... A61K 2300/00; A61K 38/1709; A61K 9/0048; A61K 38/00; C07K 14/4718
See application file for complete search history.

(56) References Cited

U.S. PATENT DOCUMENTS

| | | |
|---|---|---|
| 6,313,091 B1 | 11/2001 | Wisniewski et al. |
| 6,518,401 B1 | 2/2003 | Lee et al. |
| 8,182,841 B2 | 5/2012 | Tseng et al. |

OTHER PUBLICATIONS

Oh, et al., Stem Cells, vol. 26, pp. 1047-1055 (Jan. 10, 2008).
Johnson, et al., Invest. Ophthalmol. Vis. Sci., vol. 51, No. 4, pp. 2051-2059 (Nov. 20, 2009).
Block, et al., Stem Cells, vol. 27, No. 3, pp. 670-681 (2009).
Ma, et al., Stem Cells, vol. 24, No. 2, pp. 315-321 (2006).
Du, et al., Stem Cells, vol. 27, No. 7, pp. 1635-1642 (2009).
Ng, et al., Can.J.Ophthalmol., vol. 40, No. 3, pp. 352-368 (2005).
Liu, et al., PLoS ONE, vol. 5, No. 5, p. e10707 (May 19, 2010).
Andreoli, et al., Curr. Opin. Opthalmol., vol. 18, No. 6, pp. 502-508.
Biswas, et al. Journal of Leukocyte Biology, vol. 76, pp. 868-875 (2004).

*Primary Examiner* — Daniel C Gamett
(74) *Attorney, Agent, or Firm* — Raymond J. Lillie

(57) ABSTRACT

The present invention encompasses methods and compositions for treating an ocular disease, disorder or condition in a mammal. The invention includes a population of mesenchymal stromal cells that possess anti-inflammatory, anti-apoptotic, immune modulatory and anti-tumorigenic properties. The invention includes administration of TSG-6, STC-1, or a combination thereof to the ocular as a treatment for an ocular disease, disorder or condition in a mammal.

5 Claims, 60 Drawing Sheets

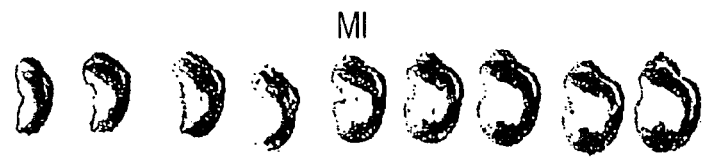
FIG. 12A — MI
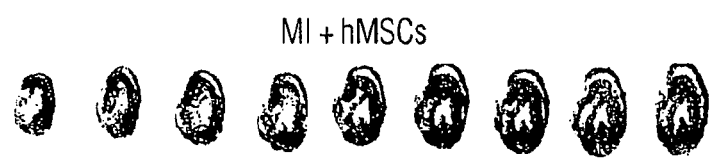
FIG. 12B — MI + hMSCs
FIG. 12C — MI + scr siRNA
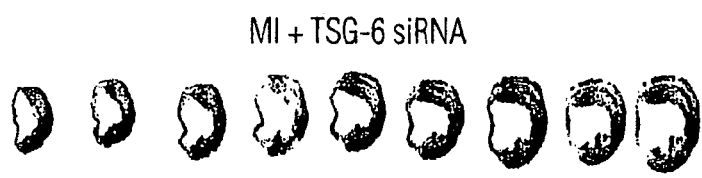
FIG. 12D — MI + TSG-6 siRNA
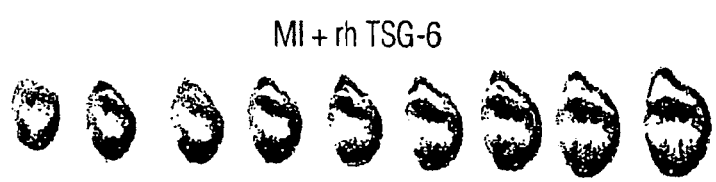
FIG. 12E — MI + rh TSG-6

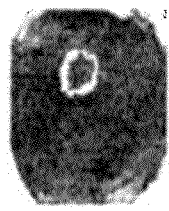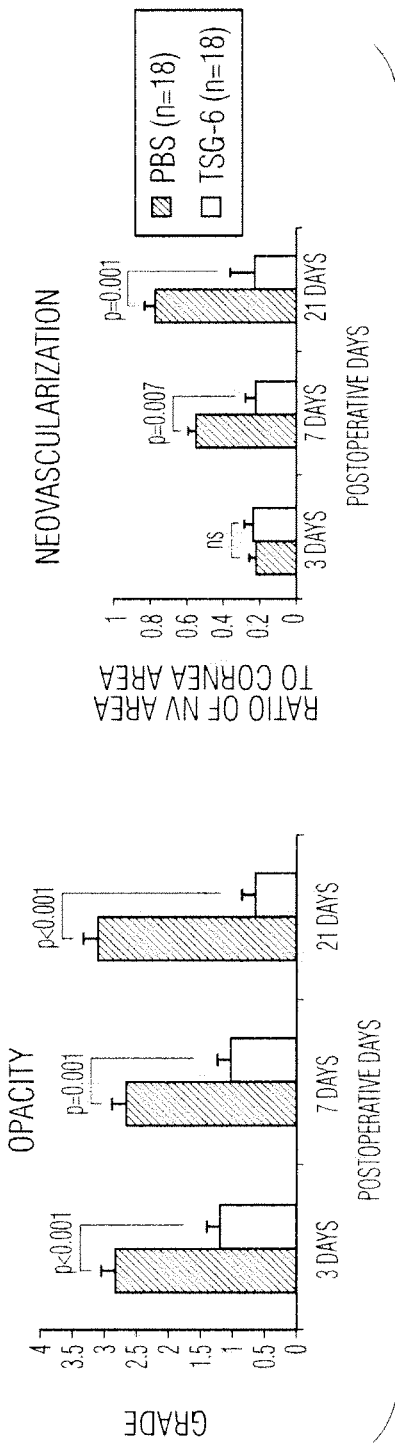
FIG. 16

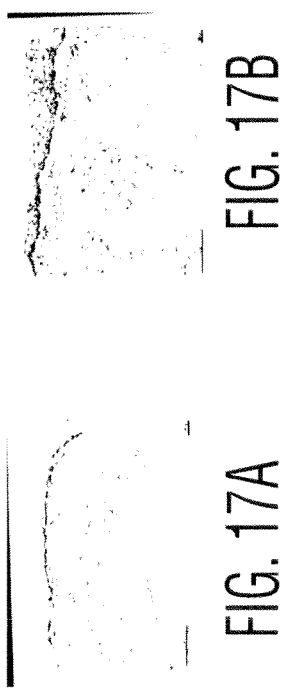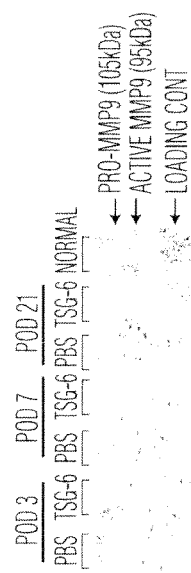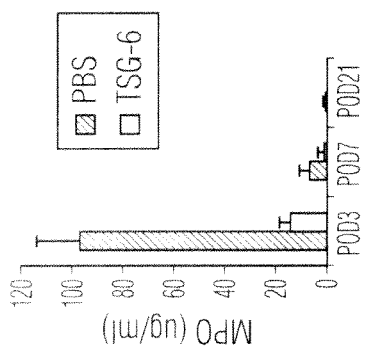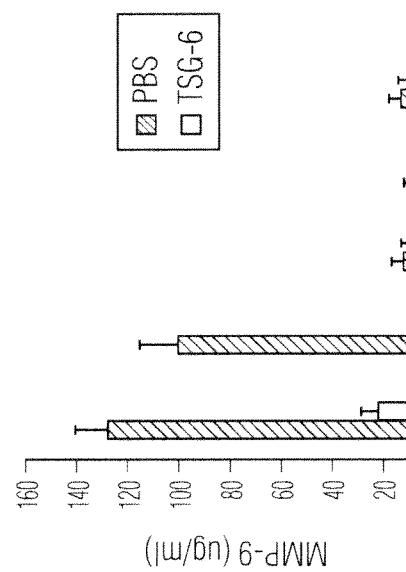

INJURY
0 4h 24h

SELECTED ENRICHED GENE ONTOLOGIES ($p < 10^{-5}$)

GROUP A (842 GENES)
ANATOMICAL STRUCTURE DEVELOPMENT
COGNITION
DETECTION OF STIMULUS
EYE DEVELOPMENT
PHOTOTRANSDUCTION
VISUAL PERCEPTION

GROUP B (108 GENES)
APOPTOSIS
CELL DEATH
DEFENSE RESPONSE
INFLAMMATORY RESPONSE
RESPONSE TO ABIOTIC STIMULUS
RESPONSE TO WOUNDING

GROUP C (307 GENES)
ACUTE INFLAMMATORY RESPONSE
CYTOKINE ACTIVITY
DEFENSE RESPONSE
IMMUNE RESPONSE
NEUTROPHIL CHEMOTAXIS
PHAGOCYTOSIS
RESPONSE TO STRESS

FIG. 31D

SECRETONEURIN (CORNEA)

HSPB4 (CORNEA)

ADULT STEM CELLS/PROGENITOR CELLS AND STEM CELL PROTEINS FOR TREATMENT OF EYE INJURIES AND DISEASES

This application is a divisional of application Ser. No. 13/643,592, filed Oct. 26, 2012, which is the national phase application of PCT Application No. PCT/US2011/000771, filed May 3, 2011, which claims priority based on provisional application Ser. No. 61/464,172, filed Feb. 28, 2011, and provisional application Ser. No. 61/330,735, filed May 3, 2010, the contents of which are incorporated by reference in their entireties.

This invention was made, in part, using funds obtained from the U.S. Government (National Institutes of Health Grant No. R21EY020962), and the U.S. Government therefore may have certain rights in this invention.

BACKGROUND OF THE INVENTION

Stem cells have significant therapeutic potential. In a non-limiting aspect, the present invention is directed to using mesenchymal stem cells to treat eye injuries and diseases. Other non-limiting aspects are directed to the therapeutic use of mesenchymal stem cells for treating diseases which include those of the lung and heart. Another non-limiting aspect of the present invention is directed to the use of anti-apoptotic and anti-inflammatory proteins such as STC-1 and TSG-6, which are expressed by mesenchymal stem cells, for treating the above-mentioned diseases and disorders.

The cornea, apart from being an important component of the refractive system of the eye, serves as a biologic and physical barrier by protecting the interior structures of the eye from environmental insults. The transparency of the cornea and, consequently, visual acuity are both dependent upon the integrity and functionality of the outermost layer, the epithelium. Most of the diseases occurring in corneal epithelium (i.e., corneal surface diseases) are accompanied by sterile inflammation and defects in wound healing. Therapies for these diseases remain problematic.

The most severe form of corneal surface diseases is limbal epithelial stem cell deficiency (LSCD). It can be primary as a result of inherited eye disease, but more commonly it is the result of acquired conditions such as chemical or thermal burn injuries, systemic autoimmune disease, contact lens keratopathy, recurrent ocular surgeries, or Stevens-Johnson Syndrome (SJS). The incidence of chemical burns is 500,000 cases per year and accounts for 7 to 18% of the 2.5 million cases of ocular trauma seen in emergency departments each year in the U.S. (Melsaether et al., 2009). The annual incidence of SJS that causes severe LSCD is 2.6 to 7.1 cases per 1 million people or about 200,000 people in the U.S. population (Foster et al., 2008). LSCD not only inflicts enormous psychological stress on patients, but it also carries an economic burden in terms of loss of productivity and prohibitive health care costs over the lifetime of the patients.

The current treatments of LSCD include anti-inflammatory drug therapy (e.g. steroids) in the early phase and transplantation of limbal epithelial stem cells (LESCs) in the late stage (Limb and Daniels, 2008). However, the anti-inflammatory drugs currently available are disappointing and are unable to prevent subsequent loss of LESCS. The current strategies for correcting LSCI by transplanting LESCs from a patient's healthy eye (limbal autograft), a living-relative, or cadaveric donors (limbal allograft) have many drawbacks (Ilari et al. 2002; Solomon et al, 2002; Cauchi et al. 2008). The limbal autograft carries the risk of creating LSCD in the donor eye (Jenkins et al., 1993) and cannot be used in patients with bilateral LSCD. Limbal allografts require long-term systemic immunosuppression because of the presence of HLA-DR antigens and Langerhans cells in the graft. Even with immunosuppression, immunological rejection occurs in 42.9% to 64.0% patients after limbal allografts (Rao et al., 1999; Tseng et al., 1998; Shi et al., 2008; Reinhard et al., 2004; Tsubota et al., 1999). Currently, ex vivo cultivation and transplantation of LESCs are being used for LSCD in some centers (summarized in Shortt et al., 2007). However, the putative stem cells observed in the limbus have not yet been reproducibly isolated or fully characterized. Moreover, the main clinical limitation for using cultured LESCs therapeutically is the availability of an autologous donor tissue. Although cultured allogeneic cells may be used in combination with systemic immunosuppression, donor allogeneic LESCs do not survive beyond a period of 9 months (Daya et al., 2005; Sharpe et al., 2007). Effective suppression of inflammation at the ocular surfaces is critical for success. Therefore, the therapies that are the goal of the present application can provide an important advance to the current therapy.

In addition to vision-threatening LSCD, there are a number of ocular surface diseases accompanied by corneal inflammation and defects in wound healing, such as keratoconjunctivitis sicca, recurrent corneal erosion, or post-refractive surgery keratitis. The most common is dry eye syndrome that affects nearly 10% of the U.S. population (Moss et al., 2000; Sehaumberg et al., 2003; Moss et al., 2008). As many as 20 to 30 million people in the United States have exhibited early signs or symptoms of dry eye, and an estimated 6 million women and 3 million men suffer from advanced effects of dry eye that alter the quality of life (Mertzanis et al., 2005; Miljanovic et al., 2007). Unfortunately, most of the currently-available therapeutic agents are only palliative and none of them abolish signs and symptoms of dry eye completely (Pflugfelder, 2007). Several studies (Clegg et al., 2006; Reddy et al., 2004; Callaghan et al., 2007) have established that the economic impact of dry eye syndrome is also substantial, in terms of both direct medical costs (e.g. for medications and physician visits) and indirect costs (e.g. lost work time and impaired productivity). In effect, there are no efficient and safe therapeutic strategies for diseases of the corneal surface.

Retinal degenerations, including age-related macular degeneration (AMD) and retinitis pigmentosa (RP), are the leading causes of legal blindness in the United States. AMD and RP share clinical and pathologic features including end-stage blindness due to photoreceptor and/or retinal pigment epithelium (RPE) cell death. Of special importance is that apoptosis of photoreceptors has been shown to be a prominent feature of human AMD (Dunaief, et al., *Arch. Ophthalmol.*, Vol. 120, No. 11, pgs. 1435-1442 (2002); Xu, et al., *Trans. Am. Ophthalmol. Soc., Vol.* 94, pgs. 411-430 (1996)). and RP (Cottet, et al., *Curr. Mol. Med.*, Vol. 9, No. 3, pgs. 375-383 (2009); Doonan, et al., *Curr. Neurosci. Res.*, Vol 1, No. 1, pgs. 47-53 (2004)) and is the underlying feature in many of the animal models of retinal degeneration (Doonan, 2004; Yu, *Invest. Ophthalmol. Vis. Sci.*, Vol. 45, No. 6, pgs. 2013-2019 (2004); Katai, et al., *Invest. Ophthalmol. Vis. Sci.*, Vol. 40, No. 8, pgs. 1802-1807 (1999); Katai, et al., *Jpn. J. Ophthalmol.,* Vol 50, No. 2, pgs. 121-127 (2006)). Reactive oxygen species (ROS) have been implicated in the initiation and/or exacerbation of cell death in AMD (Fletcher, et al., *Ophthalmic Res.*, Vol. 44, No. 3, pgs. 191-198 (2010); Beatty, et al., *Surv. Ophthalmol.*, Vol. 45, No. 2, pgs. 115-134 (2000); Winkler, *Mol. Vis.*, Vol. 5, pg. 32 (1999); Johnson, *Curr. Opin. Cln. Nutr. Metab. Care,* Vol. 13, pgs. 28-33 (2010); Totan, et al., Curr. Eye Res., Vol. 34, No. 12, pgs. 1089-1093 (2009)) and antioxidant vitamin therapy is currently one of the mainstays of treatment in non-exudative AMD and RP (Johnson, 2010; Hartong, et al., Lancet, Vol. 368, pgs. 1795-1809 (2006)). Although not curative, reduction of risk of disease and stabilization of vision have been observed following antioxidant vitamin therapy (Flectcher, 2010; Beatty, 2000; Johnson, 2010; Hartong, 2006). Moreover, two of the top modifiable risk factors in AMD-smoking and light exposure—are thought to injure photoreceptors or RPE through ROS-mediated damage (Flectcher, 2010; Johnson, 2010). In addition, oxidative damage studies in animal models of RP have implicated ROS as partially responsible for the apoptotic loss of photoreceptors (Komeima, et al., Proc. Nat. Acad. Sci., Vol. 103, No. 30, pgs. 11300-11305 (2006); Shen, et al., J. Cell. Physiol., Vol. 203, No. 3, pgs. 457-464 (2005)). Further evidence includes studies demonstrating that antioxidant based therapies slow photoreceptor death in animal models of RP (Komeima, et al; J. Cell. Physiol., Vol. 213, No. 3, pgs. 809-815 (2007); Galbinar, et al., J. Ocul. Pharmacol. Ther., Vol 25, No. 6, pgs. 475-482 (2009); Chen, et al., Nat. Nanotechnol., Vol. 1, No. 2, pgs. 142-150 (2006)) and decrease primary retinal cell (Chen, 2006; Chucair, et al., Invest. Ophthalmol. Vis. Sci., Vol. 48, No. 11, pgs. 5168-5177 (2007)) or RPE cell death in vitro (Cao, et al., Exp. Eye Res., Vol. 91, No. 1, pgs. 15-25 (2010); Kim, et al., Invest. Ophthalmol. Vis. Sci., Vol. 51, No. 1, pgs. 561-566 (2010)). Photoreceptors are sensitive particularly to oxidative stress for several reasons: (a) oxygen consumption by the retina is greater than any other tissue (Beatty, 2000); (b) photoreceptor outer segments reside near a rich vascular supply and contain high concentrations of polyunsaturated fatty acids (PUFAs) that undergo oxidation when oxygen is present (Winkler, 1999); (c) lipofuscin accumulates in the RPE during aging and is thought to be a source of ROS that is toxic to the RPE (Beatty, 2000); and (d) photoreceptors are subject to repeated photochemical injury, a process known to produce ROS (Beatty, 2000). These findings in conjunction with our preliminary data provide a strong rationale to test new stem cell based therapies known to reduce ROS-mediated apoptosis in currently incurable degenerative diseases of the retina.

Inflammation is being shown increasingly to play a role in a number of diseases, such as in myocardial infarction, stroke, Alzheimer's disease and atherosclerosis, for example. Thus, the present invention in a non-limiting aspect, is directed to the use of mesenchymal stem cells and the role of certain proteins, such as TSG-6, in treating myocardial infarction and lung diseases.

In summary, there are no effective drugs to treat corneal inflammation and ulceration caused by chemical injury to the cornea. In addition, there is a need for additional therapies for macular degeneration. There also are needs for additional therapies for diseases of the lung and heart. Thus, the present invention is directed to the use of mesenchymal stem cells and stem cell proteins as therapeutic agents.

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings embodiment(s) which are presently preferred. It should be understood, however, that the invention is not limited to the precise arrangements and instrumentalities shown.

FIGS. 1A through 1C, is a series of images depicting induction of corneal inflammation and neovascularization, one week post-injury. FIG. 1A is an image demonstrating that on slit lamp examination, corneal inflammation with active new vessels was observed, FIG. 1B is an image of immunofluorescent staining for VEGF showing the marked increase in VEGF expression in cornea. VEGF as green and the nuclei counterstained as blue. FIG. 1C is an image depicting Hematoxylin-eosin staining revealing that the cornea was densely infiltrated with inflammatory cells.

FIGS. 2A and 2B, is a series of images depicting application of cells to cornea. FIG. 2A is an image of a 6-mm-diameter hollow plastic tube emplaced to keep the eye open and the cells or media applied to the cornea into a customized applicator. FIG. 2B is an image depicting engraftment of MSCs in the cornea confirming by identification of PKH26-labeled cells in corneas by fluorescein microscopy.

FIGS. 3A through 3L, is a series of images depicting photography of cornea one (FIGS. 3A-3D), two (FIGS. 3E-3H), and three weeks (FIGS. 3I-3L) post-injury. With time, neovascularization and opacity markedly decreased in the corneas with MSCs (FIGS. 3D, 3H, 3L) or MSC-CM media three times (FIGS. 3C, 3G, 3K), while increased in the control (FIGS. 3A, 3E, 3I). Corneas treated with MSC-CM once (FIGS. 3B, 3F, 3J) showed the intermediate outcome.

FIGS. 4A through 4D, is a series of images depicting Hematoxylin-eosin staining of cornea three weeks post-injury. Control (FIG. 4A) and corneas treated with MSC-conditioned media once (FIG. 4B) were densely infiltrated with inflammatory cells in the stroma and goblet cells in the epithelium. The infiltration was markedly reduced in the corneas with MSC-conditioned media three times (FIG. 4C) or MSCs (FIG. 4D).

FIG. 5, comprising

FIG. 6, comprising

FIG. 9, comprising FIG. 9A is an image depicting clearance of human Alu sequences from blood after IV infusion of about $2\times10^6$ hMSCs into mice. Values are mean+/−$_{/-}$ SD; n=6. FIG. 9B is an image depicting standard curves for real time PCR assays of human Alu sequences in 7 organs. Values indicate $\Delta\Delta$Ct for primers for mouse/human GAPDH genes and Alu sequences on same samples. FIG. 9C is an image depicting tissue distribution of human Alu sequences 15 mm after IV infusion of about $2\times10^6$ hMSCs into mice. Values are mean+/−SD; n=6.

FIG. 9D is an image depicting standard curves for real time RT-PCR assays of human mRNA for GAPDH. Values indicate AACt for primers for mouse/human GAPDH genes and cDNA for human-specific GAPDH on same samples. FIG. 9E is an image depicting kinetics of hMSCs in lung and 6 other tissues after IV infusion of about $2 \times 10^6$ hMSCs, Values are mean +/−SD; n=6. FIG. 9F is an image depicting appearance of hMSCs in heart after IV infusion of about $1 \times 10^6$ hMSCs 1 day after permanent ligation of the left anterior descending coronary artery.

FIG. 10, comprising FIG. 10A is an image depicting real-time RT-PCR for human-specific mRNA in lung 10 hr after IV infusion of $2 \times 10^6$ hMSCs. Values are fold increase over values for cultured hMSCs, normalized by $\Delta\Delta Ct$ for hGAPDH. Symbols: hMSCs con, sample of hMSCs added to lung from control mouse before extraction of RNA; hMSCs IV 1 and 2, samples from lungs of 2 mice 10 hr after IV infusion of hMSCs. FIG. 10B is an image depicting real-time RT-PCR for human TSG-6 in mouse lung. About $2 \times 10^6$ hMSCs were infused IV into naïve mice (IV-nor) or mice at 1 hr after Ml (IV-MI) and lungs were recovered 0.25 hr to 24 hr later. Values are +/−SD; n=2 or 3 for normal mice; n=6 for MI mice. FIG. 10C is an image depicting real-time RT-PCR for TSG-6 in hMSCs and human fibroblasts from the same donor incubated in serum-free medium with 10 ng/ml TNF-α for 24 or 48 hr. Results with two passages of the same cells are shown. Values are +/−SD; n=3. FIG. 10D is an image depicting ELISAs for TSG-6 in medium from hMSCs and human fibroblasts incubated in serum-free medium with 10 ng/ml TNF-a for 48 hr. Values are ±/−SD; n=3. FIG. 10E is an image depicting real-time RT-PCR assays for TSG-6 of control hMSCs (Con), hMSCs treated with transfection reagents only (no siRNA), hMSCs transfected with a scrambled siRNA (scr siRNA) or hMSCs transduced with TSG-6 siRNA (TSG-6 siRNA). Cells were incubated with or without 10 ng/ml TNF-a for 6 hr. Values are +/−SD; n=3. FIG. 10F is an image depicting ELISAs for TSG-6 in medium after incubation of cells with or without TNF-α for 48 hr. Symbols: as in FIG. 10E. Values are +/−SD; n=3.

FIG. 11, comprising FIG. 11A is an image depicting an assay for cardiac troponin I in serum 48 hr after MI. Values are +/−SD; $p<0.01$ with n=3 (Normal) or 6 mice (MI) per group. FIG. 11B, is an image depicting plasmin activity in serum 48 hr after MI. Symbols: Normal, naïve mice; −, MI only; hMSCs, $2 \times 10^6$ hMSCs infused IV 1 hr after MI; scr siRNA, $2 \times 10^6$ hMSCs transduced with scrambled siRNA infused IV 1 hr after MI; TSG-6 siRNA, $2 \times 10^6$ hMSCs transduced with TSG-6 siRNA infused IV 1 hr after MI; rhTSG-6, 30 μg rhTSG-6 protein infused IV 1 hr and again 24 hr after MI. Values are +/−SD; $p<0.01$ with n=3 mice per group. N.S.=not significant. FIG. 11C, is an image depicting hearts assayed for pro- and active-matrix MMP9 on a gelatin zymogen gel 48 hr after MI. Image is reversed. Symbols: as in FIG. 11B. FIGS. 11D and 11E are images depicting granulocyte and monocyte infiltration in the heart 48 hr after MI. Sections stained with anti-Ly-6G and Ly-6C.Symbols: as in FIG. 11B except 100 μg rhTSG-6 protein was infused IV 1 hr and again 24 hr after MI. Magnification ×4. Scale bars, 250 μm. Values are +/−SD; n=3 or 4 for each group. $p<0.001$; N.S.=not significant.

FIG. 12, comprising FIGS. 12A through 12F, is a series of images depicting assays of Infarct Size 3 wk after MI. Each heart was cut from the apex through the base into over 400 sequential 5 μm sections and stained with Masson Trichrome. Every 20th section is shown from typical specimens. FIG. 12A is an image depicting MI. Heart with no treatment. FIG. 12B is an image depicting MI+hMSCs. $2 \times 10^6$ hMSCs infused IV 1 hr after MI. FIG. 12C is an image depicting MI+scr siRNA, $2 \times 10^6$ hMSCs transduced with scrambled siRNA infused IV 1 hr after MI. FIG. 12D is an image depicting MI+TSG-6 siRNA. $2 \times 10^6$ hMSCs transduced with TSG-6 siRNA infused IV 1 hr after MI. FIG. 12E is an image depicting MI+hTSG-6 100 μg rhTSG-6 protein infused IV 1 hr and again 24 hr after MI. FIG. 12F is an image depicting Infarct size measurements (%) obtained by midline length measurement from every $10^{th}$ section of the infarct area for a total of 20 sections per heart (Takagawa et al., 2007). Values are +/−SD; n=3 or 4 mice per group; ***$p<0.0001$ compared to MI controls; N.S. not significant compared to MI controls; *$p<0.05$ for MI+MSCs versus MI+rhTSG-6.

FIG. 16, comprising FIGS. 16A through 16F, is a series of images demonstrating that intracameral injection of TSG-6 (2 ug) decreased corneal opacity and neovascularization in cornea after injury. FIGS. 16A-16F are photo images of cornea. FIGS. 16A-16C are images depicting PBS-treated control. FIGS. 16D-16F are images depicting TSG-6-treated cornea. FIGS. 16A, 16D depict postoperative day 3. FIGS. 16B, 16E depict postoperative day 7. FIGS. 16C, 16F depict postoperative day 21. Bottom frames: Clinical evaluations of opacity (left frame) and neovascularization (right frame) of the cornea.

FIG. 17, comprising FIGS. 17A through 17G, is a series of images demonstrating intracameral injection of TSG-6 (2 ug) decreased the infiltration of neutrophils and production of MMP-9 in cornea after injury. (FIGS. 17A-17D) Hematoxylin-eosin staining of cornea. (FIGS. 17A, 17B) PBS-treated cornea. (FIGS. 17C, 17D) TSG-6-treated cornea. (FIGS. 17A, 17C) Postoperative day 3. (FIGS. 17B, 17D) Postoperative day 21. (FIG. 17E) Myeloperoxidase assay. (FIG. 17F) Gel zymography for MMP-9. (FIG. 17G) ELISA for total and active MMP-9.

FIG. 19, comprising (FIGS. 19A-19D) Photography of cornea. (FIG. 19A) PBS-treated cornea. (FIG. 19B) TSG-6 0.02 ug-treated cornea. (FIG. 19C) TSG-6 0.2 ug-treated cornea. (FIG. 19D) TSG-6 2 ug-treated cornea.

Myeloperoxidase assay and clinical grading of opacity.

DETAILED DESCRIPTION

Figure 1:
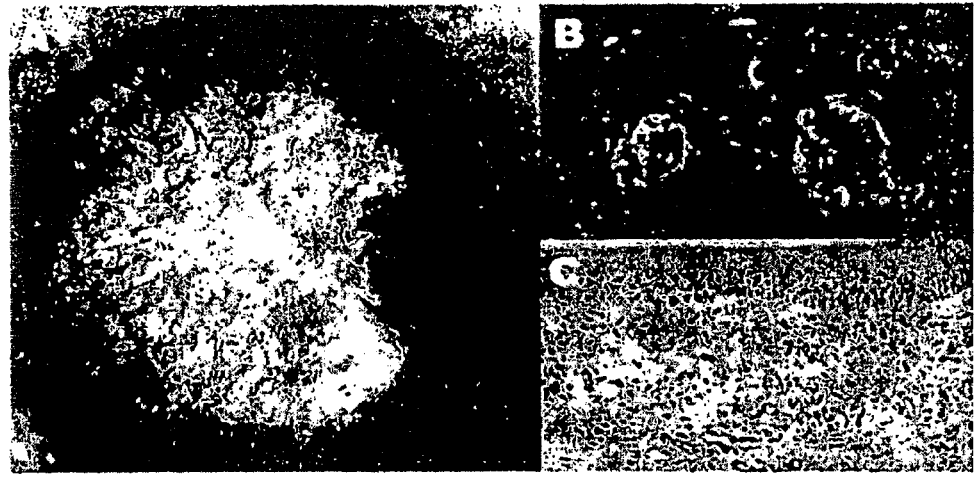
FIG. 1, comprising

The present invention relates to the discovery that adult stem/progenitor cells such as mesenchymal stromal cells (MSCs) possess novel therapeutic characteristics and therefore can be useful in therapy of a desired disease such as a disease of the eye. For example, the MSCs can be used to treat diseases associated with including but not limited to noninfectious inflammatory diseases of the cornea. This is because the MSCs of the invention can be manipulated to possess therapeutic characteristics including but not limited to expression of an anti-inflammatory protein, an anti-apoptotic protein, a protein that regulates hematopoiesis, a protein that kills cancer cells, a protein that regulates immune response, a protein that regulates homing of cells, a protein involved in cell adhesion and cell signaling, a protein that enhances angiogenesis, and the like.

The present invention is based on discovery of that MSCs can be used to treat inflammatory diseases of the cornea and other diseases or disorders of the eye using intraocular injection of the recombinant therapeutic proteins MSCs produced in response to signals from injured tissues. This therapy is based on the discovery that after a chemical burn to the cornea of a rat, application of MSCs or conditioned medium from MSCs reduced inflammation and revascularization. In another non-limiting embodiment, inflammation and revascularization of the cornea can be reduced, and other diseases or disorders of the eye may be treated by application of one or more therapeutic proteins produced by activated MSCs, such as the anti-inflammatory protein TSG-6 and biologically active fragments or analogs thereof and/or the anti-apoptotic protein STC-1 and biologically active fragments or analogs thereof.

Thus, in accordance with an aspect of the present invention, there is provided a method of treating or preventing a disease or disorder of the eye in a patient. The method comprises administering to a patient mesenchymal stem cells which have been cultured under conditions to express an increased amount of at least one protein selected from the group consisting of anti-apoptotic proteins and anti-inflammatory proteins, compared to the amount of said at least one anti-apoptotic protein and/or anti-inflammatory protein expressed by an otherwise identical population of mesenchymal stem cells which have not been cultured under conditions to express an increased amount of said at least one anti-apoptotic protein and/or anti-inflammatory protein. The mesenchymal stem cells are administered in an amount effective to treat or prevent the disease or disorder of the eye in the patient.

In a non-limiting embodiment, the at least one protein is an anti-apoptotic protein. In another non-limiting embodiment, the at least one anti-apoptotic protein is selected from the group consisting of stanniocalcin-1 (STC-1) and stanniocalcin-2 (STC-2) and biologically active fragments or analogs thereof. In yet another non-limiting embodiment, the at least one anti-apoptotic protein is STC-1 or a biologically active fragment or analogue thereof.

In another non-limiting embodiment, the at least one protein is an anti-inflammatory protein. In yet another non-limiting embodiment, the anti-inflammatory protein is TSG-6 or a biologically active fragment or analog thereof.

In another non-limiting embodiment, the at least one anti-inflammatory protein may be an anti-apoptotic protein, including, but not limited to, STC-1 or a biologically active fragment or analog thereof. Although the scope of this embodiment is not to be limited to any theoretical reasoning, unresolved inflammation may be caused in part by an increase in reactive oxygen species, or ROS. STC-1 recently has been shown to reduce reactive oxygen species by increasing expression of uncoupling protein-2, which makes mitochondria more efficient in reducing ROS. Therefore, anti-apoptotic proteins, such as STC-1, and cells which express at least one anti-apoptotic protein, including the MSCs of the present invention, may be useful in reducing ROS and unresolved inflammation in the diseases and disorders of the eye mentioned herein. Thus, such anti-apoptotic proteins and the cells mentioned herein also may be anti-inflammatory as well as anti-apoptotic.

In another aspect of the present invention, there is provided a method of treating or preventing a disease or disorder of the eye in a patient by administering to the patient at least one protein selected from the group consisting of anti-apoptotic proteins and anti-inflammatory proteins in an amount effective to treat or prevent the disease or disorder of the eye in the patient.

In a non-limiting embodiment, the at least one protein is an anti-apoptotic protein. In another non-limiting embodiment, the anti-apoptotic protein is STC-1 or STC-2 or biologically active fragments or analogs thereof. In yet another non-limiting embodiment, the anti-apoptotic protein is STC-1 or a biologically active fragment or analog thereof.

In another non-limiting embodiment, the at least one protein is an anti-inflammatory protein. In another non-limiting embodiment, the anti-inflammatory protein is TSG-6 or a biologically active fragment or analog thereof.

The present invention should not be limited only to treating disease of the cornea, but is applicable to any disease associated with the eye, such as diseases of the retina or the macula, including, but not limited to, macular degeneration. That is, the invention is useful for treating diseases, disorders, or conditions of the eye associated with inflammation or degeneration of eye tissue.

Definitions

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

The term "about" will be understood by persons of ordinary skill in the art and will vary to some extent on the context in which it is used.

As used herein, the term "autologous" is meant to refer to any material derived from the same individual to which it is later to be re-introduced into the individual.

As used herein, the term "biocompatible lattice," is meant to refer to a substrate that can facilitate formation into three-dimensional structures conducive for tissue development. Thus, for example, cells can be cultured or seeded onto such a biocompatible lattice, such as one that includes extracellular matrix material, synthetic polymers, cytokines, growth factors, etc. The lattice can be molded into desired shapes for facilitating the development of tissue types. Also, at least at an early stage during culturing of the cells, the medium and/or substrate is supplemented with factors (e.g., growth factors, cytokines. extracellular matrix material, etc.) that facilitate the development of appropriate tissue types and structures.

As used herein, the term "bone marrow stromal cells," "stromal cells," "mesenchymal stem cells," "mesenchymal stromal cells" or "MSCs" are used interchangeably and refer to a cell derived from bone marrow (reviewed in Prockop, 1997), peripheral blood (Kuznetsov et al., 2001), adipose tissue (Guilak et al., 2004), umbilical cord blood (Rosada et al., 2003), synovial membranes (De Bari et al., 2001), and periodontal ligament (Seo et al., 2005), embryonic yolk sac, placenta, umbilical cord, skin, and blood (U.S. Pat. Nos. 5,486,359 and 7,153,500), fat, and synovial fluid. MSCs are characterized by their ability to adhere to plastic tissue culture surfaces (Friedenstein et al.; reviewed in Owen & Friedenstein, 1988), and by being effective feeder layers for hematopoietic stem cells (Eaves et al., 2001). In addition, MSCs can be differentiated both in culture and in vivo into osteoblasts and chondrocytes, into adipocytes, muscle cells (Wakitani et al., 1995) and cardiomyocytes (Fukuda and Yuasa, 2006), into neural precursors (Woodbury et al, 2000; Deng et al., 2001, Kim et al., 2006; Marcsehi et al., 2006; Krampera et al, 2007). Mesenchymal stem cells (MSCs) may be purified using methods known in the art (Wakitani et al., 1995; Fukuda and Yuasa, 2006; Woodbury et al., 2000; Deng et al., 2001; Kim et al., 2006; Mareschi et al., 2006; Krampera et al., 2007), and serve as progenitors for mesenchymal cell lineages, including bone, cartilage, ligament, tendon, adipose, muscle, cardiac tissue, stroma, dermis, and other connective tissues. (See U.S. Pat. Nos. 6,387,369 and 7,101,704). Mesenchymal stem cells (MSCs) may be purified using methods known in the art (Wakitami, et al., 1995; Fukuda and Yuasa, 2006; Woodbury, et al., 2000; Deng, et al., 2001; Kim, et al., 2006; Mareschi, et al., 2006, Krampera, et al., 2007).

As used herein, the term "modulate" is meant to refer to any change in biological state, i.e. increasing, decreasing, and the like.

The terms "precursor cell," "progenitor cell," and "stem cell" are used interchangeably in the art and herein and refer either to a pluripotent, or lineage-uncommitted, progenitor cell, which is potentially capable of an unlimited number of mitotic divisions to either renew itself or to produce progeny cells which will differentiate into the desired cell type. Unlike pluripotent stem cells, lineage-committed progenitor cells are generally considered to be incapable of giving rise to numerous cell types that phenotypically differ from each other. Instead, progenitor cells give rise to one or possibly two lineage-committed cell types.

"Ocular region" or "ocular site" means any area of the eyeball, including the anterior and posterior segment of the eye, and which generally includes, but is not limited to, any functional (e.g., for vision) or structural tissues found in the eyeball, or tissues or cellular layers that partly or completely line the interior or exterior of the eyeball. Specific examples of areas of the eyeball in an ocular region include, but are not limited to, the anterior chamber, the posterior chamber, the vitreous cavity, the choroid, the suprachoroidal space, the conjunctiva, the subconjunctival space, the episcieral space, the intracorneal space, the epicorneal space, the sclera, the pars plana, surgically-induced avascular regions, the macula, and the retina.

"Ocular condition" means a disease, ailment or condition which affects or involves the eye or one of the parts or regions of the eye. Broadly speaking the eye includes the eyeball, including the cornea, and other tissues and fluids which constitute the eyeball, the periocular muscles (such as the oblique and rectus muscles) and the portion of the optic nerve which is within or adjacent to the eyeball.

"Graft" refers to a cell, tissue, organ, or otherwise any biological compatible lattice for transplantation.

"Glaucoma" means primary, secondary and/or congenital glaucoma. Primary glaucoma can include open angle and closed angle glaucoma. Secondary glaucoma can occur as a complication of a variety of other conditions, such as injury, inflammation, vascular disease and diabetes. The increased pressure of glaucoma causes blindness because it damages the optic nerve where it enters the eye. Thus, in one non-limiting embodiment, by lowering reactive oxygen species, STC-1, or MSCs which express increased amounts of STC-1, may be employed in the treatment of glaucoma and prevent or delay the onset of blindness.

"Inflammation-mediated" in relation to an ocular condition means any condition of the eye which can benefit from treatment with an anti-inflammatory agent, and is meant to include, but is not limited to, uveitis, macular edema, acute macular degeneration, retinal detachment, ocular tumors, fungal or viral infections, multifocal choroiditis, diabetic uveitis. proliferative vitreoretinopathy (PVR), sympathetic opthalmia, Vogt Koyanagi-Harada (VKH) syndrome, histoplasmosis, and uveal diffusion.

"Injury" or "damage" are interchangeable and refer to the cellular and morphological manifestations and symptoms resulting from an inflammatory-mediated condition, such as, for example, inflammation, as well as tissue injuries caused by means other than inflammation, such as chemical injury, including chemical burns, as well as injuries caused by infections, including but not limited to, bacterial, viral, or fungal infections.

"Intraocular" means within or under an ocular tissue. An intraocular administration of a drug delivery system includes administration of the drug delivery system to a sub-tenon, subconjunctival, suprachoroidal, intravitreal and like location. An intraocular administration of a drug delivery system excludes administration of the drug delivery system to a topical, systemic, intramuscular, subcutaneous, intraperitoneal, and the like location.

"Macular degeneration related condition" refers to any of a number of disorders and conditions in which the macula degenerates or loses functional activity. The degeneration or loss of functional activity can arise as a result of, for example, cell death, decreased cell proliferation, loss of normal biological function, or a combination of the foregoing. Macular degeneration can lead to and/or manifest as alterations in the structural integrity of the cells and/or extracellular matrix of the macula, alteration in normal cellular and/or extracellular matrix architecture, and/or the loss of function of macular cells. The cells can be any cell type normally present in or near the macula including RPE cells, photoreceptors, and capillary endothelial cells. Age-related macular degeneration, or ARMD, is the major macular degeneration related condition, but a number of others are known including, but not limited to, Best macular dystrophy, Sorsby fundus dystrophy, Mallatia Leventinese and Doyne honeycomb retinal dystrophy.

"Ocular neovascularization" (ONV) is used herein to refer to choroidal neovascularization or retinal neovascularization, or both.

"Retinal neovascularization" (RNV) refers to the abnormal development, proliferation, and/or growth of retinal blood vessels, e.g., on the retinal surface.

"Cornea" refers to the transparent structure forming the anterior part of the fibrous tunic of the eye. It consists of five layers, specifically: 1) anterior corneal epithelium, continuous with the conjunctiva; 2) anterior limiting layer (Bowman's membrane); 3) substantia propria, or stromal layer; 4) posterior limiting layer (Descemet's membrane); and 5) endothelium of the anterior chamber or keratoderma.

"Retina" refers to the innermost of the three tunics of the eyeball, surrounding the vitreous body and continuous posteriorly with the optic nerve. It is divided into the pars optica, which rests upon the choroids, the pars ciliaris, which rests upon the ciliary body. and the pars iridica. which rests upon the posterior surface of the iris. Grossly, the retina is composed of an outer, pigmented layer (pars pigmentosa) and an inner, transparent layer (pars nervosa), which together make up the pars optica. The optic part of the eye consists of 9 layers named from within to outward as: 1) internal limiting membrane; 2) nerve fiber layer; 3) layer of ganglion cells; 4) inner plexiform layer; 5) inner nuclear layer; 6) outer plexiform layer; 7) outer nuclear layer; 8) external limiting membrane; and 9) a layer of rods and cones.

"Allogeneic" refers to a graft derived from a different animal of the same species.

"Xenogeneic" refers to a graft derived from an animal of a different species.

"Transplant" refers to a biocompatible lattice or a donor tissue, organ or cell, to be transplanted. An example of a transplant may include but is not limited to skin cells or tissue, bone marrow, and solid organs such as heart, pancreas, kidney, lung and liver, Preferably, the transplant is a human neural stem cell.

As defined herein, an "allogeneic bone marrow stromal cell (BMSC)" is obtained from a different individual of the same species as the recipient.

"Donor antigen" refers to an antigen expressed by the donor tissue to be transplanted into the recipient.

"Alloantigen" is an antigen that differs from an antigen expressed by the recipient.

As used herein, an "effector cell" refers to a cell which mediates an immune response against an antigen. In the situation where a transplant is introduced into a recipient, the effector cells can be the recipient's own cells that elicit an immune response against an antigen present in the donor transplant. In another situation, the effector cell can be part of the transplant, whereby the introduction of the transplant into a recipient results in the effector cells present in the transplant eliciting an immune response against the recipient of the transplant.

As used herein, a "therapeutically effective amount" is the amount of an agent which is sufficient to provide a beneficial effect to the subject to which the agent is administered.

As used herein "endogenous" refers to any material from or produced inside an organism, cell or system.

"Exogenous" refers to any material introduced from or produced outside an organism, cell, or system.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and nonviral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses that incorporate the recombinant polynucleotide.

Description

The present invention relates to the discovery that MSCs express high levels of a series of therapeutic genes such as TSG-6, for an anti-inflammatory protein and STC-1, for an anti-apoptotic protein. Accordingly, MSCs are useful as anti-inflammatory therapy in ocular diseases, including but not limited to noninfectious inflammatory diseases of the cornea, ocular hypertension, dry eye syndrome, macular degeneration, and retinal degeneration diseases or conditions.

The present invention encompasses methods and compositions for reducing and/or eliminating an inflammatory response in a mammal by treating the mammal with an amount of MSC effective to reduce or inhibit inflammation in the eye of a mammal, and/or effect repair or healing of damaged tissue in the eye of a mammal. In one non-limiting embodiment, local application of MSCs, that have been pre-activated in culture to express high levels of therapeutic proteins to the site of injury is useful for treating the injury. In another non-limiting embodiment, the therapeutic proteins that are secreted from the pre-activated MSCs are administered locally to the site of injury. In yet another non-limiting embodiment, recombinant proteins or synthetic or purified proteins, that correspond or mimic the desirable proteins secreted by the MSCs can be administered to the site of injury.

In one non-limiting embodiment, at least one therapeutic protein secreted from MSCs or a recombinant, synthetic, or purified version of the therapeutic protein is administered to the mammal by way of intraocular administration. For example, in a non-limiting embodiment, the MSCs or proteins may be administered intravitreally.

The present invention provides a method for treating an ocular disease, comprising injecting intraocularly into the mammal an effective amount of a therapeutic protein derived from, or expressed by MSCs or a recombinant version or a synthesized or purified version thereof, such as TSG-6, including biologically active fragments or analogs thereof, STC-1, including biologically active fragments or analogs thereof, or a combination thereof. The invention, however, should not be limited only to TSG-6 and STC-1. Rather, any therapeutic protein secreted by MSCs is applicable to the present invention of treating an ocular disease in a mammal. For example, MSCs exhibit high viability and express high levels of a series of genes for therapeutic proteins: TSG-6, for an anti-inflammatory protein; STC-1, for an anti-apoptotic protein; LIF, for a protein that regulates cell growth and development; IL-11, for a protein that regulates hematopoiesis; TNFSF10 (also known as TRAIL), for a protein that kills some cancer cells and regulates immune response; IL-24, for a protein that kills some cancer cells; CXCR4, for a protein that regulates homing of cells; ITGA2 (also known as integrin α2), for a protein involved in cell adhesion and cell signaling; and IL-8, for a protein that enhances angiogenesis.

Ocular Injuries (A) Foreign Bodies

25% of all ocular injuries involve foreign bodies on the surface of the cornea. No scarring will occur if the injury affects only the corneal epithelium, but if it also affects the Bowman zone, scarring is possible. After removal of the foreign body, the eye is treated with a sulfonamide or antibiotic and, if there is ciliary congestion and photophobia, or if the removal of the foreign body were difficult, it is treated with a cycloplegic such as 5% homatropine. In some instances, the therapeutic compositions of the present invention are designed to accelerate healing of the injury caused by the foreign body and to prevent infection, and to improve the clinical outcome.

(B) Chemical Burns

Chemical burns are treated by first diluting the chemical by flushing the eye with fluid, and then preventing infection through the use of topical antibiotics.

Intraocular pressure may be reduced by applying timolol, epinephrine, acetazolamide. or other similar agents. If epithelialization of the cornea is incomplete after one week, there is a danger of stromal necrosis, in addition to the risk of infection. It is therefore critical that the healing be accelerated to reduces these risks.

Severe scarring is another common result of chemical burns. The therapeutic compositions of the present invention are designed to accelerate the healing of the corneal erosion caused by the chemical burns, to prevent stromal necrosis and infection of the eye, and to reduce corneal scarring and thereby restore/preserve corneal transparency.

Unexpectedly the compositions of the present invention are able to prevent or reduce scar formation while simultaneously enhancing ocular healing, wound repair, and maintaining corneal transparency. While not wishing to be bound by any specific mechanism of action, it appears that these beneficial effects can be obtained due to the anti-inflammatory actions of the compositions. In some instances, the beneficial effects can be obtained due to the combination of anti-inflammatory and anti-apoptotic actions of the compositions of the invention.

(C) Lacerations

Lacerations of the cornea are followed by prolapse of the iris, which closes the injury. As in all eye injuries, there is a risk of infection. Lacerations also may extend to the sclera, which is a much more severe injury. In such a case, surgery is required to remove prolapsed uveal tissue from the injured area, and the sclera is closed with sutures. The therapeutic compositions of the present invention are designed to accelerate the healing of the laceration and to prevent infection.

(D) Traumatic, Toxic, Deficiency, and Hereditary Optic Neuropathies

Optic neuropathies affect the optic nerve, which may affect vision adversely. Traumatic optic neuropathies may be caused when the head is struck by an object, such as a ball, or if it is pierced by an object such as a bullet. Toxic optic neuropathies are caused by chemicals toxic to the optic nerve; a common example is the ingestion of methanol. Deficiency optic neuropathies can result from vitamin deficiencies such as a B12 deficiency, and may cause lesions in the optic nerve. Hereditary optic neuropathies can be caused by mutations in the nuclear or mitochondrial genomes. The therapeutic and prophylactic compounds of this invention could be used to heal the optic nerve and correct vitamin deficiencies. They may also create an environment which would reduce or prevent mutations in optic cell genomes.

(E) Inflammatory Conditions

Inflammation-mediated conditions of the eye which may be treated by the methods of the invention include but is not limited to uveitis, macular edema, acute macular degeneration, retinal detachment, ocular tumors, fungal or viral infections, multifocal choroiditis, diabetic uveitis, proliferative vitreoretinopathy (PVR), sympathetic opthalmia, Vogt Koyanagi-Harada (VKH) syndrome, histoplasmosis, and uveal diffusion. In a non-limiting embodiment, the inflammation-mediated condition of the eye is uveitis. In another non-limiting embodiment, the inflammation-mediated condition of the eye is proliferative vitrioretinopathy (PVR).

Suspensions of microspheres may be used as an anti-inflammatory therapy of the eye, especially for treating inflammatory conditions of the ocular adnexa, palpebral or bulbar conjunctiva, cornea and anterior segment of the globe. Common therapeutic applications for anti-inflammatory suspensions of microspheres include viral, allergic conjunctivitis, acne rosacea, iritis and iridocyclitis. Microspheres may also be used to ameliorate inflammation associated with, corneal injury due to chemical or thermal burns, or penetration of foreign bodies. Such conditions may result from surgery, injury, allergy or infection to the eye and can cause severe discomfort.

Notably, microspheres have considerable therapeutic advantages in reducing inflammatory responses, compared to the prevalent topical ocular use of NSAI agents and corticosteroids. Use of topical steroids is associated with a number of complications, including posterior subcapsular cataract formation, elevation of intraocular pressure, secondary ocular infection, retardation of corneal wound healing, uveitis, mydriasis, transient ocular discomfort and ptosis. Numerous systemic complications also may arise from the topical ocular application of corticosteroids. These complications include adrenal insufficiency, Cushing's syndrome, peptic ulceration, osteoporosis, hypertension, muscle weakness or atrophy, inhibition of growth, diabetes, activation of infection, mood changes and delayed wound healing.

(F) Ocular Surgical Applications

Compositions of microspheres in accordance with the present invention, may also be used to ameliorate inflammation associated with ocular surgery, and in this context are particularly useful in a prophylactic modality as well as in promoting healing and reducing scarring as has been detailed above.

Of particular suitability is the use of the compositions of the invention for:

post-trabeculectomy (filtering surgery); post pterygium surgery; post ocular adnexa trauma and surgery; post intraocular surgery and specifically: post vitrectomy, post retinal detachment and post retinotomylectomy.

It will be appreciated by the artisan that these are intended to serve as non-limitative examples of prevalent surgical procedures for which the compositions and methods of the invention are useful.

Pre-Activated

Based upon the disclosure provided herein, MSCs can be obtained from any source. The MSCs may be autologous with respect to the recipient (obtained from the same host) or allogeneic with respect to the recipient. In addition, the MSCs may be xenogeneic to the recipient (obtained from an animal of a different species), for example rat MSCs may be used to suppress inflammation in a human.

In a further non-limiting embodiment, MSCs used in the present invention can be isolated, from the bone marrow of any species of mammal, including but not limited to, human, mouse, rat, ape, gibbon, bovine. In a non-limiting embodiment, the MSCs are isolated from a human, a mouse, or a rat. In another non-limiting embodiment, the MSCs are isolated from a human.

Based upon the present disclosure, MSCs can be isolated and expanded in culture in vitro to obtain sufficient numbers of cells for use in the methods described herein provided that the MSCs are cultured in a manner that promotes aggregation and formation of spheroids. For example, MSCs can be isolated from human bone marrow and cultured in complete medium (DMEM low glucose containing 4 mM L-glutamine, 10% FBS, and 1% penicillin/streptomycin) in hanging drops or on non-adherent dishes. However, the invention should in no way be construed to be limited to any one method of isolating and culturing medium. Rather, any method of isolating and culturing medium should be construed to be included in the present invention provided that the MSCs are cultured in a manner that promotes aggregation and formation of spheroids.

Any medium capable of supporting MSCs in vitro may be used to culture the MSCs. Media formulations that can support the growth of MSCs include, but are not limited to, Dulbecco's Modified Eagle's Medium (DMEM), alpha modified Minimal Essential Medium (αMEM), and Roswell Park Memorial Institute Media 1640 (RPMI Media 1640) and the like. Typically, 0 to 20% fetal bovine serum (FBS) or 1-20% horse serum is added to the above medium in order to support the growth of MSCs. A defined medium, however, also can be used if the growth factors, cytokines, and hormones necessary for culturing MSCs are provided at appropriate concentrations in the medium. Media useful in the methods of the invention may contain one or more compounds of interest, including but not limited to antibiotics, mitogenic or differentiation compounds useful for the culturing of MSCs. The cells may be grown in one non-limiting embodiment, at temperatures between 27° C. to 40° C., in another non-limiting embodiment at 31° C. to 37° C., and in another non-limiting embodiment in a humidified incubator. The carbon dioxide content may be maintained between 2% to 10% and the oxygen content may be maintained between 1% and 22%; however, the invention should in no way be construed to be limited to any one method of isolating and culturing MSCs. Rather, any method of isolating and culturing MSCs should be construed to be included in the present invention.

Antibiotics which can be added into the medium include, but are not limited to, penicillin and streptomycin. The concentration of penicillin in the culture medium is about 10 to about 200 units per ml. The concentration of streptomycin in the culture medium is about 10 to about 200 µg/ml.

In a non-limiting embodiment, the mesenchymal stem cells are cultured under conditions which, as noted hereinabove, provide for the aggregation of the mesenchymal stem cells into a spheroidal aggregate, and provide for optimal expression of the therapeutic protein(s).

In one non-limiting embodiment, the mesenchymal stem cells are cultured in a medium, such as complete culture medium (CCM), for example, which includes serum in an amount effective to upregulate one or more of the hereinabove noted therapeutic proteins. For example, the medium may include fetal bovine serum in an amount of up to 20%. In a non-limiting embodiment, the fetal bovine serum is present in an amount of about 17%. The mesenchymal stem cells are cultured under conditions and for a period of time (for example, 7 or 8 days) sufficient to provide a sufficient number of cells for further culturing. The culture medium may include growth factors other than or in addition to serum to upregulate one or more of the hereinabove noted therapeutic proteins.

In one non-limiting embodiment, the spheroids can be prepared by culturing the MSCs on bacterial plates (as distinct from plates treated for culture of animal cells) so that the MSCs aggregate spontaneously into spheroids (Bartosh, 2010).

The cells then are cultured under conditions which promote the formation of spheroidal aggregates of the cells. In one non-limiting embodiment, the cells are cultured as hanging drops. Each drop of cells contains mesenchymal stem cells in an amount which provides for optimal expression of the at least one therapeutic protein. In a non-limiting embodiment, the hanging drops of the cells are cultured in a medium, such as complete culture medium, containing fetal bovine serum in an amount of up to 20%. In a non-limiting embodiment, the fetal bovine serum is present in an amount of about 17%.

In another non-limiting embodiment, each hanging drop of mesenchymal stem cells that is cultured contains from about 10,000 to about 500,000 cells/drop. In another non-limiting embodiment, each hanging drop of mesenchymal stem cells that is cultured contains from about 10,000 to about 250,000 cells/drop. In a further non-limiting embodiment, each hanging drop of cells contains from about 10,000 to about 25,000 cells/drop. In yet another non-limiting embodiment, each hanging drop of cells contains about 25,000/drop.

The hanging drops of mesenchymal stem cells are cultured for a period of time sufficient for forming spheroidal aggregates of the mesenchymal stem cells. In general, the drops of cells are cultured for a period of time of up to 4 days.

Once the spheroidal aggregates of the mesenchymal stem cells are formed, the mesenchymal stem cells may, if desired, be dissociated from the spheroids by incubating the spheroids in the presence of a dissociation agent, such as trypsin and/or EDTA, for example.

The invention comprises the treatment of an MSC in culture to express therapeutic proteins that are effective in treating a disease of the ocular. For example, the MSCs can be cultured in the presence of TNF-α. In some instances, the MSCs can be pre-activated by culturing in the presence of IFN-µγ. In other instances, the MSCs can be pre-activated by culturing in the presence of IL-1B. In some instances, MSCs can be pre-activated using any combination of TNF-α, IFN-µ, and IL-1B Pre-activation of the MSCs induce the cells to secrete therapeutic proteins. Thus, the MSCs themselves, the secreted proteins, or the combination of both provide a source of a therapeutic composition. In one embodiment, a recombinant version of the therapeutic protein secreted from the pre-activated MSCs can be used as a therapeutic composition.

In some instances, the MSCs are contacted with an agent that induces MSCs to secrete therapeutic proteins in a culturing medium. The culturing medium generally comprises a base media. Non-limiting examples of base media useful in the methods of the invention include Minimum Essential Medium Eagle, ADC-1, LPM (Bovine Serum Albumin-free), F10(HAM), F12 (HAM), DCCM1, DCCM2, RPMI 1640, BGJ Medium (with and without Fitton-Jackson Modification), Basal Medium Eagle (BME-with the addition of Earle's salt base), Dulbecco's Modified Eagle Medium (DMEM-without serum), Yamane, IMEM-20, Glasgow Modification Eagle Medium (GMEM), Leibovitz L-15 Medium, McCoy's 5A Medium, Medium M199 (M199E-with Earle's salt base), Medium M199 (M199H-with Hank's salt base), Minimum Essential Medium Eagle (MEM-E-with Earle's salt base), Minimum Essential Medium Eagle (MEM-H-with Hank's salt base) and Minimum Essential Medium Eagle (MEM-NAA with non essential amino acids), among numerous others, including medium 199, CMRL 1415, CMRL 1969, CMRL 1066, NCTC 135, MB 75261, MAB 8713. DM 145, Williams' G, Neuman & Tytell, Higuchi, MCDB 301, MCDB 202, MCDB 501, MCDB 401, MCDB 411, MDBC 153. A preferred medium for use in the present invention is DMEM. These and other useful media are available from GIBCO, Grand Island, N.Y., USA and Biological Industries, Bet HaEmek, Israel, among others. A number of these media are summarized in *Methods in Enzymology*, Volume LVIII, "Cell Culture", pp. 62-72, edited by William B. Jakoby and Ira H. Pastan, published by Academic Press, Inc.

Additional non-limiting examples of media useful in the methods of the invention can contain fetal serum of bovine or other species at a concentration of at least 1% to about 30%, preferably at least about 5% to 15%, mostly preferably about 10%;

Embryonic extract of chicken or other species can be present at a concentration of about 1% to 30%, preferably at least about 5% to 15%, most preferably about 10%.

In a non-limiting embodiment, the MSCs are isolated from the mammal into which the treated MSC are to be introduced; however, the MSCs may also be isolated from an organism of the same or different species as the mammal. The mammal may be any organism having bone tissue. In a non-limiting embodiment, the mammal is a human.

Genetic Modification

The cells of the invention may be transformed stably or transiently with a nucleic acid of interest prior to introduction into the eye of the mammal. Nucleic acid sequences of interest include, but are not limited to those encoding gene products TSG-6 and biologically active fragments and analogs thereof, and STC-1 and biologically active fragments and analogs thereof. Methods of transformation of MSCs are known to those skilled in the art, as are methods for introducing cells into a bone at the site of surgery or fracture.

In cases in which a gene construct is transfected into a cell, the heterologous gene is linked operably to regulatory sequences required to achieve expression of the gene in the cell. Such regulatory sequences typically include a promoter and a polyadenylation signal.

In a non-limiting embodiment, the gene construct is provided as an expression vector that includes the coding sequence for a heterologous protein operably linked to essential regulatory sequences such that when the vector is transfected into the cell, the coding sequence will be expressed by the cell. The coding sequence is linked operably to the regulatory elements necessary for expression of that sequence in the cells. The nucleotide sequence that encodes the protein may be cDNA, genomic DNA, synthesized DNA or a hybrid thereof, or an RNA molecule such as mRNA.

The gene construct includes the nucleotide sequence encoding the beneficial protein is linked operably to the regulatory elements and may remain present in the cell as a functioning cytoplasmic molecule, a functioning episomal molecule, or it may integrate into the cell's chromosomal DNA. Exogenous genetic material may be introduced into cells where it remains as separate genetic material in the form of a plasmid. Alternatively, linear DNA which can integrate into the chromosome may be introduced into the cell. When introducing DNA into the cell, reagents which promote DNA integration into chromosomes may be added. DNA sequences which are useful to promote integration may also be included in the DNA molecule. Alternatively, RNA may be introduced into the cell.

The regulatory elements for gene expression include: a promoter, an initiation codon, a stop codon, and a polyadenylation signal. It is preferred that these elements be operable in the cells of the present invention. Moreover, it is preferred that these elements be linked operably to the nucleotide sequence that encodes the protein such that the nucleotide sequence can be expressed in the cells and thus the protein can be produced. Initiation codons and stop codons are generally considered to be part of a nucleotide sequence that encodes the protein; however, it is preferred that these elements are functional in the cells. Similarly, promoters and polyadenylation signals used must be functional within the cells of the present invention, Examples of promoters useful to practice the present invention include, but are not limited to, promoters that are active in many cells such as the cytomegalovirus promoter, SV40 promoters, and retroviral promoters. Other examples of promoters useful to practice the present invention include, but are not limited to, tissue-specific promoters, i.e. promoters that function in some tissues but not in others; also, promoters of genes normally expressed in the cells with or without specific or general enhancer sequences. In some non-limiting embodiments, promoters are used which express genes in the cells constitutively with or without enhancer sequences. Enhancer sequences are provided in such embodiments when appropriate or desirable.

The cells of the present invention can be transfected using well known techniques readily available to those having ordinary skill in the art. Exogenous genes may be introduced into the cells using standard methods where the cell expresses the protein encoded by the gene. In some embodiments, cells are transfected by calcium phosphate precipitation transfection, DEAE dextran transfection, electroporation, microinjection, liposome-mediated transfer, chemical-mediated transfer, ligand mediated transfer or recombinant viral vector transfer.

In some embodiments, recombinant adenovirus vectors are used to introduce DNA with desired sequences into the cell. In some embodiments, recombinant retrovirus vectors are used to introduce DNA with desired sequences into the cells. In other embodiments, standard $CaPO_4$, DEAE dextran or lipid carrier mediated transfection techniques are employed to incorporate desired DNA into dividing cells. In some embodiments, DNA is introduced directly into cells by microinjection. Similarly, well-known electroporation or particle bombardment techniques can be used to introduce foreign DNA into the cells. A second gene is usually co-transfected or linked to the therapeutic gene. The second gene is frequently a selectable antibiotic-resistance gene. Standard antibiotic resistance selection techniques can be used to identify and select transfected cells. Transfected cells are selected by growing the cells in an antibiotic that will kill cells that do not take up the selectable gene. In most cases where the two genes co-transfected and unlinked, the cells that survive the antibiotic treatment contain and express both genes.

In another embodiment, the cells of the invention can be modified genetically, e.g., to express exogenous genes or to repress the expression of endogenous genes. In accordance with this embodiment, the cell is exposed to a gene transfer vector comprising a nucleic acid including a transgene, such that the nucleic acid is introduced into the cell under conditions appropriate for the transgene to be expressed within the cell. The transgene generally is contained in an expression cassette, including a coding polynucleotide linked operably to a suitable promoter. The coding polynucleotide can encode a protein, or it can encode biologically active RNA, such as antisense RNA or a ribozyme. Thus, the coding polynucleotide can encode a gene conferring, for example, resistance to a toxin, a hormone (such as peptide growth hormones, hormone releasing factor, sex hormones, adrenocorticotrophic hormones, cytokines such as interferons, interleukins, and lymphokines), a cell surface-bound intracellular signaling moiety such as cell-adhesion molecules and hormone receptors, and factors promoting a given lineage of differentiation, or any other transgene with known sequence.

The expression cassette containing the transgene should be incorporated into the genetic vector suitable for delivering the transgene to the cell. Depending on the desired end application, any such vector can be so employed to modify the cells genetically (e.g., plasmids, naked DNA, viruses such as adenovirus, adeno-associated virus, herpesvirus, lentivirus, papillomavirus, retroviruses, etc.). Any method of constructing the desired expression cassette within such vectors can be employed, many of which are well known in the art, such as by direct cloning, homologous recombination, etc. The desired vector will determine largely the method used to introduce the vector into the cells, which are generally known in the art. Suitable techniques include protoplast fusion, calcium-phosphate precipitation, gene gun, electroporation, and infection with viral vectors.

The MSCs, in a non-limiting embodiment, may have one or more genes modified or may be treated such that the modification has the ability to cause the MSCs to self-destruct or "commit suicide" because of such modification, or upon presentation of a second drug (eg., a prodrug) or signaling compound to initiate such destruction of the MSCs.

It should be understood that the methods described herein may be carried out in a number of ways and with various modifications and permutations thereof that are well known in the art. It should also be appreciated that any theories set forth as to modes of action or interactions between cell types should not be construed as limiting this invention in any manner, but are presented such that the methods of the invention can be more fully understood.

Therapy

The present invention includes a method of using MSCs as a therapy to inhibit inflammation in the context of an ocular disease. The invention is based on the discovery that MSCs exhibit high viability and express high levels of anti-inflammatory, anti-apoptotic, immune modulatory, and anti-tumorigenic molecules.

One skilled in the art would appreciate, based upon the disclosure provided herein, that the ability of MSC to suppress inflammation and apoptosis provides a means for treating an ocular disease. In one embodiment, the MSCs themselves can be administered to the desired site of the eye. In another embodiment, the therapeutic proteins secreted from the MSCs are administered to the desired site of the eye. In yet another embodiment, a recombinant version of the desired therapeutic protein secreted from the MSC is administered to the site of the eye.

The invention provides a method of preventing or treating various ocular diseases or conditions, including the following: maculopathies/retinal degeneration: macular degeneration, including age related macular degeneration (ARMD), such as non-exudative age related macular degeneration and exudative age related macular degeneration, choroidal neovascularization, retinopathy, including diabetic retinopathy, acute and chronic macular neuroretinopathy, central serous chorioretinopathy, and macular edema, including cystoid macular edema, and diabetic macular edema. Uveitis/retinitis/choroiditis: acute multifocal placoid pigment epitheliopathy, Behcet's disease, birdshot retinochoroidopathy, infectious (syphilis, Lyme Disease, tuberculosis, toxoplasmosis), uveitis, including intermediate uveitis (pars planitis) and anterior uveitis, multifocal choroiditis, multiple evanescent white dot syndrome (MEWDS), ocular sarcoidosis, posterior scleritis, serpignous choroiditis, subretinal fibrosis, uveitis syndrome, and Vogt-Koyanagi-Harada syndrome. Vascular diseases/exudative diseases: retinal arterial occlusive disease, central retinal vein occlusion, disseminated intravascular coagulopathy, branch retinal vein occlusion, hypertensive fundus changes, ocular ischemic syndrome, retinal arterial microaneurysms, Coat's disease, parafoveal telangiectasis, hemi-retinal vein occlusion, papillophlebitis, central retinal artery occlusion, branch retinal artery occlusion, carotid artery disease (CAD), frosted branch angitis, sickle cell retinopathy and other hemoglobinopathies, angioid streaks, familial exudative vitreoretinopathy, Eales disease, Traumatic/surgical: sympathetic ophthalmia, uveitic retinal disease, retinal detachment, trauma, laser, PDT, photocoagulation, hypoperfusion during surgery, radiation retinopathy, bone marrow transplant retinopathy. Proliferative disorders: proliferative vitreal retinopathy and epiretinal membranes, proliferative diabetic retinopathy. Infectious disorders: ocular histoplasmosis, ocular toxocariasis, presumed ocular histoplasmosis syndrome (PONS), endophthalmitis, toxoplasmosis, retinal diseases associated with HIV infection, choroidal disease associated with HIV infection, uveitic disease associated with HIV Infection, viral retinitis, acute retinal necrosis, progressive outer retinal necrosis, fungal retinal diseases, ocular syphilis, ocular tuberculosis, diffuse unilateral subacute neuroretinitis, and myiasis. Genetic disorders: retinitis pigmentosa, systemic disorders with associated retinal dystrophies, congenital stationary night blindness, cone dystrophies, Stargardt's disease and fundus flavimaculatus, Best's disease, pattern dystrophy of the retinal pigmented epithelium, X-linked retinoschisis, Sorsby's fundus dystrophy, benign concentric maculopathy, Bietti's crystalline dystrophy, pseudoxanthoma elasticum. Retinal tears/holes: retinal detachment, macular hole, giant retinal tear. Tumors: retinal disease associated with tumors, congenital hypertrophy of the RPE, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, intraocular lymphoid tumors. Miscellaneous: punctate inner choroidopathy, acute posterior multifocal placoid pigment epitheliopathy, myopic retinal degeneration, acute retinal pigment epithelitis and the like.

An anterior ocular condition is a disease, ailment or condition which affects or which involves an anterior (i.e. front of the eye) ocular region or site, such as a periocular muscle, an eyelid or an eyeball tissue or fluid which is located anterior to the posterior wall of the lens capsule or ciliary muscles. Thus, an anterior ocular condition primarily affects or involves the conjunctiva, the cornea, the anterior chamber, the iris, the posterior chamber (behind the retina but in front of the posterior wall of the lens capsule), the lens or the lens capsule and blood vessels and nerve which vascularize or innervate an anterior ocular region or site.

Thus, an anterior ocular condition can include a disease, ailment or condition, such as for example, aphakia; pseudophakia; astigmatism; blepharospasm; cataract; conjunctival diseases; conjunctivitis, including, but not limited to, atopic keratoconjunctivitis; corneal injuries, including, but not limited to, injury to the corneal stromal areas; corneal diseases; corneal ulcer; dry eye syndromes; eyelid diseases; lacrimal apparatus diseases; lacrimal duct obstruction; myopia; presbyopia; pupil disorders; refractive disorders and strabismus. Glaucoma can also be considered to be an anterior ocular condition because a clinical goal of glaucoma treatment can be to reduce a hypertension of aqueous fluid in the anterior chamber of the eye (i.e. reduce intraocular pressure).

A posterior ocular condition is a disease, ailment or condition which primarily affects or involves a posterior ocular region or site such as choroid or sclera (in a position posterior to a plane through the posterior wall of the lens capsule), vitreous, vitreous chamber, retina, optic nerve (i.e. the optic disc), and blood vessels and nerves which vascularize or innervate a posterior ocular region or site. Thus, a posterior ocular condition can include a disease, ailment or condition, such as for example, acute macular neuroretinopathy; Behcet's disease; choroidal neovascularization; diabetic uveitis; histoplasmosis; infections, such as fungal or viral-caused infections; macular degeneration, such as acute macular degeneration, non-exudative age related macular degeneration and exudative age related macular degeneration; edema, such as macular edema, cystoid macular edema and diabetic macular edema; multifocal choroiditis; ocular trauma which affects a posterior ocular site or location; ocular tumors; retinal disorders, such as central retinal vein occlusion, diabetic retinopathy (including proliferative diabetic retinopathy), proliferative vitreoretinopathy (PVR), retinal arterial occlusive disease, retinal detachment, uveitic retinal disease; sympathetic opthalmia; Vogt Koyanagi-Harada (VKH) syndrome; uveal diffusion; a posterior ocular condition caused by or influenced by an ocular laser treatment; posterior ocular conditions caused by or influenced by a photodynamic therapy, photocoagulation, radiation retinopathy, epiretinal membrane disorders, branch retinal vein occlusion, anterior ischemic optic neuropathy, non-retinopathy diabetic retinal dysfunction, retinitis pigmentosa, and glaucoma. Glaucoma can be considered a posterior ocular condition because the therapeutic goal is to prevent the loss of or reduce the occurrence of loss of vision due to damage to or loss of retinal cells or optic nerve cells (i.e. neuroprotection).

Other diseases or disorders of the eye which may be treated in accordance with the present invention include, but are not limited to, ocular cicatricial pemphigoid (OCP), and cataracts.

In a non-limiting embodiment, when inflammation of and/or injury to and/or disease or disorder of the eye is associated with an infection, e.g., a bacterial, viral, or fungal infection, the anti-apoptotic or anti-inflammatory proteins or mesenchymal stem cells of the present invention may be administered in combination with at least one anti-infective agent.

In general, at least one anti-infective agent which is administered in combination with the anti-apoptotic or anti-inflammatory proteins or mesenchymal stem cells of the present invention depends upon the type of infection, e.g., bacterial, viral, or fungal, to the eye, the type or species of bacterium, virus, or fungus associated with the infection, and the extent and severity of the infection, and the age, weight, and sex of the patient.

In a non-limiting embodiment, when the infection of the eye is associated with one or more bacteria, at least one anti-infective agent which is administered in combination with the proteins or mesenchymal stem cells of the present invention is at least one anti-bacterial agent. Anti-bacterial agents which may be administered include, but are not limited to, quinolone antibiotics, such as, for example, levofloxacin (Cravit), moxifloxacin (Vigamox), gatifloxacin (Zy-mar), cephalosporin, aminoglycoside antibiotics (e.g., gentamycin), and combinations thereof.

In another non-limiting embodiment, when the infection of the eye is associated with one or more viruses, the anti-infective agent which is administered in combination with the proteins or mesenchymal stem cells of the present invention is at least one anti-viral agent. Anti-viral agents which may be employed include those which are known to those skilled in the art.

In another non-limiting embodiment, when the infection of the eye is associated with one or more fungi, the anti-infective agent which is administered in combination with the proteins or mesenchymal stem cells of the present invention is at least one anti-fungal agent. Anti-fungal agents which may be employed include, but are not limited to, natamycin, amphotericin B, and azoles, including fluconazole and itraconzole.

In yet another non-limiting embodiment, when the infection of the eye is associated with more than one of bacteria, viruses, and fungi, more than one of anti-bacterial, anti-viral, and anti-fungal agents are administered in combination with the proteins or mesenchymal stem cells of the present invention.

In a non-limiting embodiment, the mesenchymal stem cells or the anti-apoptotic or anti-inflammatory proteins are administered to a patient to treat or prevent macular degeneration, including the forms of macular degeneration hereinabove described. In another non-limiting embodiment, the mesenchymal stem cells or the anti-apoptotic or anti-inflammatory proteins may be administered to a patient in combination with other therapeutic agents employed in treating macular degeneration. Such therapeutic agents include, but are not limited to, angiogenesis inhibitors, and anti-vascular endothelial growth factor A (VEGF-A) antibodies (eg., Avastin, Lucentis), agents or drugs which bind angiogenic agents, such as VEGF trap agents, tyrosine kinase inhibitors, which are anti-angiogenic, angiogenic protein receptor antagonists, and antibodies and antibody fragments which recognize heat shock proteins, including, but not limited to antibodies and antibody fragments which recognize the small heat shock protein HSPB4, HSP90, HSP70, HSP65, or HSP27, and heat shock protein antagonists, including, but not limited to, antagonists to HSPB4, HSP90, HSP70, HSP65, and HSP27.

In accordance with another aspect of the present invention, there is provided a method of treating or preventing a disease or disorder of the eye in a patient, comprising administering to the patient at least one antibody or antibody fragment which recognizes a heat shock protein or at least one heat shock protein antagonist. The at least one antibody or antibody fragment or heat shock protein antagonist is administered in an amount effective to treat a disease or disorder of the eye in said patient.

Diseases or disorders of the eye which may be treated include, but are not limited to, those hereinabove described.

Antibodies or antibody fragments which may be administered in accordance with the present invention include, but are not limited to, antibodies or antibody fragments which recognize the small heat shock protein HSPB4, HSP90, HSP70, HSP65, or HSP27. In a non-limiting embodiment, the antibody or antibody fragment is an antibody or antibody fragment which recognizes the small heat shock protein HSPB4.

In another non-limiting embodiment, the mesenchymal stem cells or the anti-apoptotic or anti-inflammatory proteins of the present invention are administered in combination with a heat shock protein antagonist. In a non-limiting embodiment, the heat shock protein antagonist is an HSPB4 antagonist.

The at least one antibody or antibody fragment may be a monoclonal or polyclonal antibody, or a human, non-human, humanized, or chimeric antibody.

The at least one antibody or antibody fragment or heat shock protein antagonist may be administered by methods such as those hereinabove described, and in conjunction with an acceptable pharmaceutical carrier such as those hereinabove described.

Another non-limiting embodiment of the present invention encompasses the route of administering MSCs to the recipient of the transplant. MSCs can be administered by a route which is suitable for the placement of the transplant, i.e. a biocompatible lattice or a donor tissue, organ or cell, to be transplanted. MSCs can be administered systemically, i.e., parenterally, by intravenous injection or can be targeted to a particular tissue or organ, such as bone marrow. MSCs can be administered via a subcutaneous implantation of cells or by injection of the cells into connective tissue, for example, muscle. MSCs can be administered via an intraocular implantation of cell or by injection of cells into the desired ocular region. In a non-limiting embodiment, the MSCs are administered intracamerally, i.e., to the anterior chamber of the eye.

MSCs can be suspended in an appropriate diluent. Suitable excipients for injection solutions are those that are biologically and physiologically compatible with the MSCs and with the recipient, such as buffered saline solution or other suitable excipients. The composition for administration can be formulated, produced and stored according to standard methods complying with proper sterility and stability.

The dosage of the MSCs varies within wide limits and may be adjusted to the individual requirements in each particular case. The number of cells used depends on the weight and condition of the recipient, the number and/or frequency of administrations, and other variables known to those of skill in the art, including, but not limited to, the age and sex of the patient, the disease or disorder being treated, and the extent and severity thereof.

Administration of Therapeutic Protein

The invention provides therapeutic proteins produced by MSCs in response to an injury signal. The therapeutic proteins can protect the corneal surface from damage by increasing the viability and proliferation of corneal epithelial progenitors and by suppressing inflammation in corneal surface.

In one non-limiting embodiment, the invention provides a method for treating or preventing a disease or disorder of the eye, such as, for example, reducing one or more symptoms of inflammation associated with an ocular disease in a mammalian subject, comprising providing a composition comprising purified tumor necrosis factor-alpha stimulated gene 6 (TSG-6) protein or a biologically active fragment or analog thereof, to the mammalian subject, thereby reducing one or more symptoms of inflammation associated with an ocular disease.

In another non-limiting embodiment, the invention provides a method for treating or preventing a disease or disorder of the eye, such as, for example, reducing one or more symptoms of inflammation associated with an ocular disease in a mammalian subject, comprising providing a composition comprising purified stanniocalcin-1 (STC-1) protein or a biologically active fragment or analog thereof, to the mammalian subject, thereby reducing one or more symptoms of inflammation associated with an ocular disease.

The therapeutic proteins of the invention can be obtained by any method. For example, in a non-limiting embodiment, the proteins can be purified from a transgenic cell that (a) comprises a heterologous nucleotide sequence encoding the protein, and (b) expresses the protein.

Any cell that may be transformed to express a heterologous nucleotide sequence may be used to express, for example, TSG-6 protein, or a biologically active fragment or analog thereof, or STC-1 or a biologically active fragment or analog thereof. Such cells include human and non-human eukaryotic animal cells. In another embodiment, the cell is a non-human eukaryotic animal cell.

In another non-limiting embodiment, the therapeutic proteins may be synthesized by an automatic protein or peptide synthesizer by means known to those skilled in the art.

It will also be appreciated that fragments or variants or analogs of the above-mentioned proteins differing in sequence from their naturally occurring counterparts but retaining their biological activity can also be used.

In certain non-limiting embodiments of the invention, a fragment or variant or analog of a naturally occurring polypeptide is at least 70% identical, at least 80% identical, at least 90% identical, at least 95% identical, over an amino acid portion that constitutes at least 10%, at least 20%, at least 30%, at least 40%, at least 50%, at least 60%, at least 70%, at least 80%, or at least 90%, or 100% of the length of the naturally occurring counterpart. For example, variant that exhibits at least 50%, at least 60%, at least 70%, at least 80%, at least 90%, or greater sequence identity, over the relevant portion of the sequence could be used, wherein % identity is determined as described above. The amino acid portion, in a non-limiting embodiment, is at least 20 amino acids in length, and in another non-limiting embodiment, at least 50 amino acids in length. Alternately, a fragment or variant can display significant or, preferably, substantial homology to a naturally occurring counterpart. Generally a fragment or variant of a naturally occurring polypeptide possesses sufficient structural similarity to its naturally occurring counterpart that it is recognized by an antibody (e.g., a polyclonal or monoclonal antibody) that recognizes the naturally occurring counterpart.

Administration of the compositions of this invention is typically parenteral, by intravenous, subcutaneous, intramuscular, or intraperitoneal injection, or by infusion or by any other acceptable systemic method. In a non-limiting embodiment, the compositions of the invention are provided to the mammal by intraocular administration. In a non-limiting embodiment, administration is by intravenous infusion, typically over a time course of about 1 to 5 hours. In addition, there are a variety of oral delivery methods for the administration of therapeutic proteins, and these can be applied to the therapeutic proteins of this invention.

Alternatively, in a non-limiting embodiment, the compositions of the present invention may be administered to the eye topically, such as, for example, in the form of eye drops. In a further non-limiting embodiment, eye drops which include at least one anti-inflammatory protein, such as TSG-6 protein or an analogue or fragment thereof, are administered to the cornea in order to treat or prevent a disease or disorder of the cornea.

In another non-limiting embodiment, the compositions of the present invention may be administered systemically, such as by intravenous administration, or intraocularly, such as by intracameral administration, i.e., to the anterior chamber of the eye.

Often, treatment dosages are titrated upward from a low level to optimize safety and efficacy. Generally, daily dosages will fall within a range of about 0.01 to 20 mg protein per kilogram of body weight. Typically, the dosage range will be from about 0.1 to 5 mg protein per kilogram of body weight.

Various modifications or derivatives of the proteins, such as addition of polyethylene glycol chains (PEGylation), may be made to influence their pharmacokinetic and/or pharmacodynamic properties.

To administer the protein by other than parenteral administration, the protein may be coated or co-administered with a material to prevent its inactivation. For example, the protein may be administered in an incomplete adjuvant, co-administered with enzyme inhibitors or administered in liposomes. Enzyme inhibitors include pancreatic trypsin inhibitor, diso-propylfluorophosphate (DEP) and trasylol. Liposomes include water-in-oil-in-water, CGF emulsions, as well as conventional liposomes (Strejan et al., (1984) J. *Neuroimmunol.* 7:27).

An "effective amount" of a composition of the invention is an amount that will ameliorate one or more of the well known parameters that characterize medical conditions such as inflammation associated with the cornea, as well as the other diseases and disorders of the eye hereinabove described. An effective amount, in the context of inflammatory diseases of the cornea, as well as the other diseases or disorders hereinabove described, is the amount of protein or cell or a combination of both that is sufficient to accomplish one or more of the following: decrease the severity of symptoms; decrease the duration of disease exacerbations; increase the frequency and duration of disease remission/symptom-free periods; prevent fixed impairment and disability; and/or prevent/attenuate chronic progression of the disease.

Although the compositions of this invention can be administered in simple solution, they are more typically used in combination with other materials such as carriers, preferably pharmaceutical carriers. Useful pharmaceutical carriers can be any compatible, non-toxic substance suitable for delivering the compositions of the invention to a patient. Sterile water, alcohol, fats, waxes, and inert solids may be included in a carrier. Pharmaceutically acceptable adjuvants (buffering agents, dispersing agents) may also be incorporated into the pharmaceutical composition. Generally, compositions useful for parenteral administration of such drugs are well known; e.g., Remington's Pharmaceutical Science, 17th Ed. (Mack Publishing Company, Easton, Pa., 1990). Alternatively, compositions of the invention may be introduced into a patient's body by implantable drug delivery systems [Urquhart et al., Ann. Rev. Pharmacol. Toxicol. 24:199 (1984).

Therapeutic formulations may be administered in many conventional dosage formulations. Formulations typically comprise at least one active ingredient, together with one or more pharmaceutically acceptable carriers.

The formulations conveniently may be presented in unit dosage form and may be prepared by any methods well known in the art of pharmacy. See, e.g., Gilman et al. (eds.) (1990), The Pharmacological Bases of Therapeutics, 8th Ed., Pergamon Press; and Remington's Pharmaceutical Sciences, supra, Easton, Pa.; Avis, et al. (eds.) (1993) Pharmaceutical Dosage Forms: Parenteral Medications Dekker, N.Y.; Lieberman et al. (eds.) (1990), Pharmaceutical Dosage Forms: Tablets, Dekker, N.Y.; and Lieberman et al. (eds.) (1990), Pharmaceutical Dosage Forms: Disperse Systems, Dekker, N.Y.

In additional non-limiting embodiments, the present invention contemplates administration of the proteins by gene therapy methods, e.g., administration of an isolated nucleic acid encoding a protein of interest. The proteins of the present invention have been well-characterized, both as to the nucleic acid sequences encoding the proteins and the resultant amino acid sequences of the proteins. Engineering of such isolated nucleic acids by recombinant DNA methods is well within the ability of one skilled in the art. Codon optimization, for purposes of maximizing recombinant protein yields in particular cell backgrounds, also is well within the ability of one skilled in the art. Gene therapy methods are well known in the art. See, e.g., WO96/07321 which discloses the use of gene therapy methods to generate intracellular antibodies.

There are two major approaches for introducing a nucleic acid encoding the protein (optionally contained in a vector) into a patient's cells; in vivo and ex vivo. For in vivo delivery the nucleic acid is injected directly into the patient, usually at the site where the protein is required. For ex vivo treatment, the patient's cells are removed, the nucleic acid is introduced into these isolated cells and the modified cells are administered to the patient either directly or, for example, encapsulated within porous membranes which are implanted into the patient (see, e.g., U.S. Pat. Nos. 4,892,538 and 5,283,187). There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. Commonly used vectors for ex vivo delivery of the gene are retroviral and lentiviral vectors.

Preferred in vivo nucleic acid transfer techniques include transfection with viral vectors such as adenovirus, Herpes Simplex I virus, adeno-associated virus, lipid-based systems (useful lipids for lipid-mediated transfer of the gene are DOTMA, DOPE and DC-Chol, for example), naked DNA, and transposon-based expression systems. For review of the currently known gene marking and gene therapy protocols see Anderson, et al., Science 256:808-8 13 (1992). See also WO 93/25673 and the references cited therein.

Therapeutic compositions and formulations thereof of the invention can be used, for example, for reducing inflammation due to seasonal or bacterial conjunctivitis, for reducing post-surgical pain and inflammation, to prevent or treat fungal or bacterial infections of the eye, to treat herpes ophthalmicus, to reduce intraocular pressure, or to treat endophthalmitis.

More particularly, in one non-limiting embodiment, the present invention provides a method for treating an ophthalmic disorder in a mammal (e.g., including human and non-human primates), the method comprising administering to the eye of the mammal a therapeutically effect amount of a formulation of the present invention comprising a lipid phase, an aqueous phase and a therapeutic agent as hereinabove described, wherein the therapeutic agent is useful for treating the ophthalmic disorder. In one embodiment, the ophthalmic disorder is post-operative pain. In another embodiment, the ophthalmic disorder is ocular inflammation resulting from, e.g., iritis, conjunctivitis, seasonal allergic conjunctivitis, acute and chronic endophthalmitis, anterior uveitis, uveitis associated with systemic diseases, posterior segment uveitis, chorioretinitis, pars planitis, masquerade syndromes including ocular lymphoma, pemphigoid, scleritis, keratitis, severe ocular allergy, corneal abrasion and blood-aqueous barrier disruption. In yet another embodiment, the ophthalmic disorder is post-operative ocular inflammation resulting from, for example, photorefractive keratectomy, cataract removal surgery, intraocular lens implantation and radial keratotomy.

In employing the liposome formulations of the present invention, in a non-limiting embodiment, administration is ocularly, which term is used to mean delivery of therapeutic agents through the surface of the eye, including the sclera, the cornea, the conjunctiva and the limbus, or into the anterior chamber of the eye. Ocular delivery can be accomplished by numerous means, for example, by topical application of a formulation such as an eye drop, by injection, or by means of an electrotransport drug delivery system.

In another non-limiting embodiment, the mesenchymal stem cells or therapeutic proteins employed for treating a disease or disorder of the eye may be contained in a nanoparticle. Such nanoparticles may be formed by methods known to those skilled in the art.

Such nanoparticles may be administered ocularly, i.e., through the surface of the eye, including the sclera, cornea, conjunctiva, and the limbus, or into the anterior chamber of the eye. Such ocular administration may be accomplished by any of a variety of means, including, in a non-limiting embodiment, by topical application of a formulation such as an eye drop, by injection, or by means of an electotransport drug delivery system.

EXAMPLES

The invention is now described with reference to the following Examples. These Examples are provided for the purpose of illustration only, and the invention is not limited to these Examples, but rather encompasses all variations which are evident as a result of the teachings provided herein.

Example 1

MSCs and MSC-derived Factors Suppressed Inflammation and Neovascularization, and Promoted Wound Healing in Chemically-injured Rat Cornea Beneficial effects of MSCs and MSC-derived factors have been observed in suppressing corneal inflammation/neovascularization and promoting wound healing (Oh et al., 2008). Corneal inflammation, neovascularization, and delayed wound healing were induced in rats by applying 100% ethanol for 30 sec and scraping both the epithelium in the limbus and the whole cornea. The reliability and reproducibility of this model was previously confirmed and repetitively used by other researchers (Cho et al., 1998; Avila et al., 2001; Ti et al., 2002; Espana et al., 2003; Homma et al, 2004; Oh et al., 2009b). Massive infiltration of inflammatory cells and growth of new vessels in cornea were induced in this model (FIG. 1).

Figure 2:
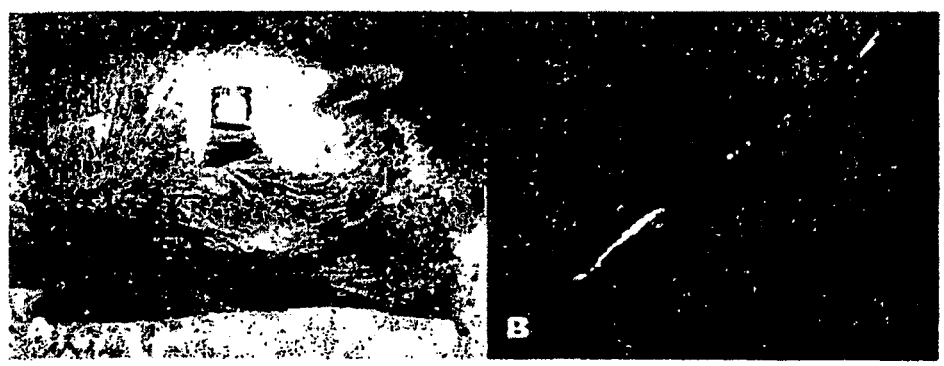
FIG. 2, comprising

Immediately after injury, rat MSCs or conditioned media (CM) derived from MSC cultures were put into an applicator and allowed to remain in the damaged cornea for two hours. A 6-mm-diameter hollow tube was used as an applicator (FIG. 2). This method of application has previously been proven effective for applying stem cells to cornea (Homma et al., 2004; Ueno et al., 2007). The following were the four groups that were studied and subjected to different treatments: (1) 200 µL of fresh media (control group, n=10), (2) 200 µL of supernatants collected from the MSCs culture (MSC-CM I group, n=10), (3) 200 µL MSC-CM applied for two hours a day over three consecutive days (MSC-CM II group, n=10), (4) 200 µL of media containing $2\times10^6$ MSCs (MSC group, n=10).

Figure 3:
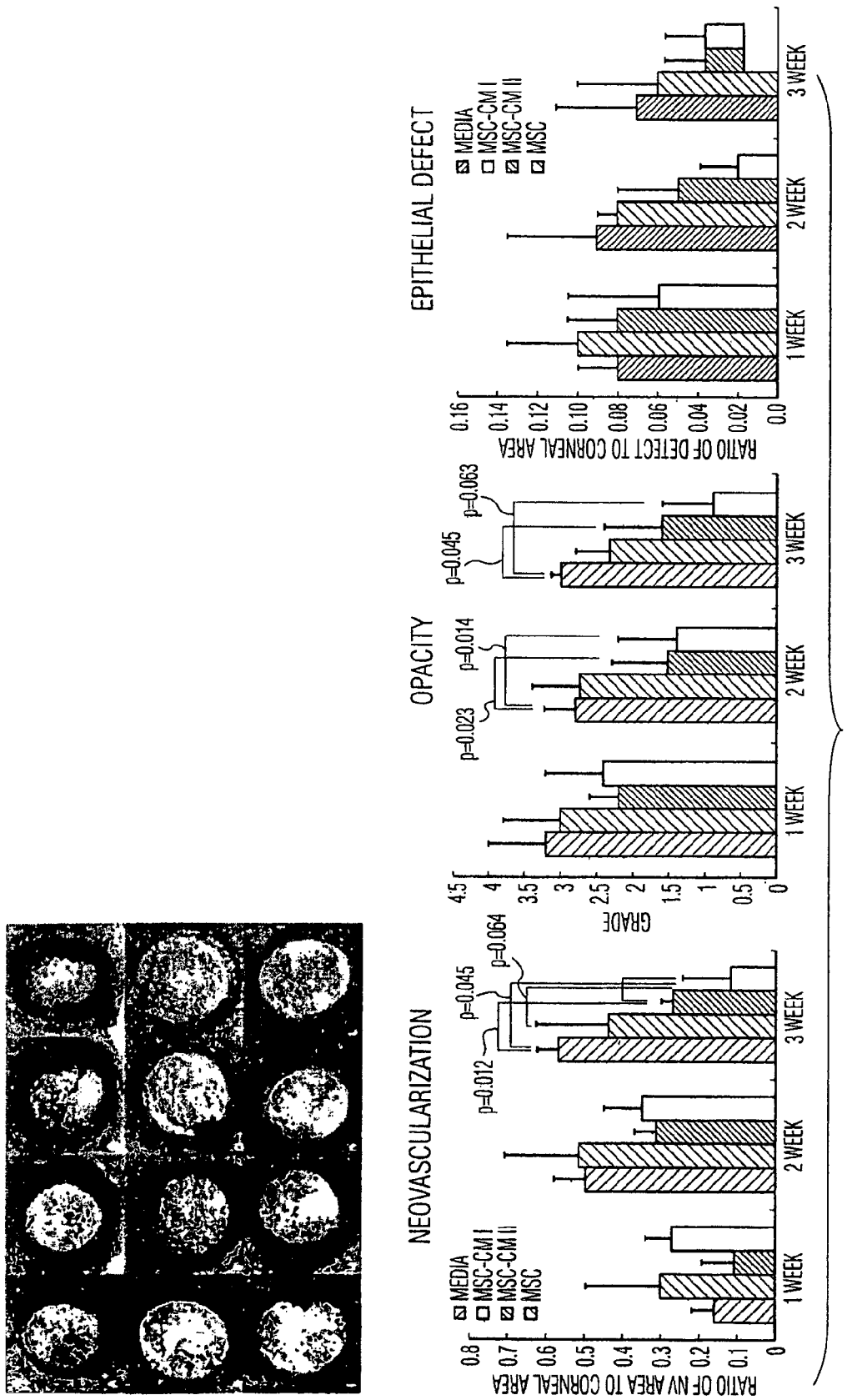
FIG. 3, comprising

Effects of MSCs or MSC-CM on the cornea were determined in three ways: (I) gross examination by slit-lamp biomicroscopy based on the findings of transparency, neovascularization (NV), and epithelial defects, (2) histological analysis for infiltration of inflammatory cells (hematoxylin-eosin staining) or CD4+ T cells (immunofluorescent staining), and (3) ELISA and real time PCR assays for inflammation- and angiogenesis-related cytokines. As a result, it was found that corneal inflammation and NV rapidly decreased in MSC-treated corneas over time after injury, while they gradually increased in the vehicle-treated controls (FIG. 3). The degree of corneal inflammation and NV was the lowest in the MSC group and the highest in the control group. Notably, it was observed that MSC-CM was also effective in reducing corneal inflammation and NV in proportion to the number of MSC-CM applications. More specifically, corneas treated three times with MSC-CM (MSC-CM II group) were more transparent compared to both the controls and the corneas that were treated only once with MSC-CM (MSC-CM I group). Re-epithelialization was faster in the corneas treated with MSCs and MSC-CM.

Figure 4:
FIG. 4, comprising
Figure 5A:
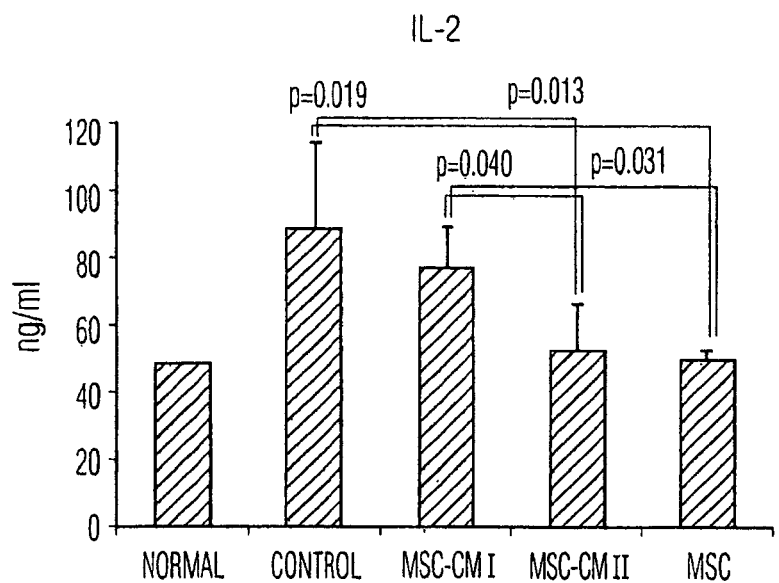
FIGS. 5A through 5D, is a series of images demonstrating inflammation-related cytokine expression evaluated by ELISA. IL-2 and IFN-$\gamma$ were repressed in the corneas treated with MSCs or MSCs-conditioned media three times (MSC-CM II) compared to the control.
Figure 5B:
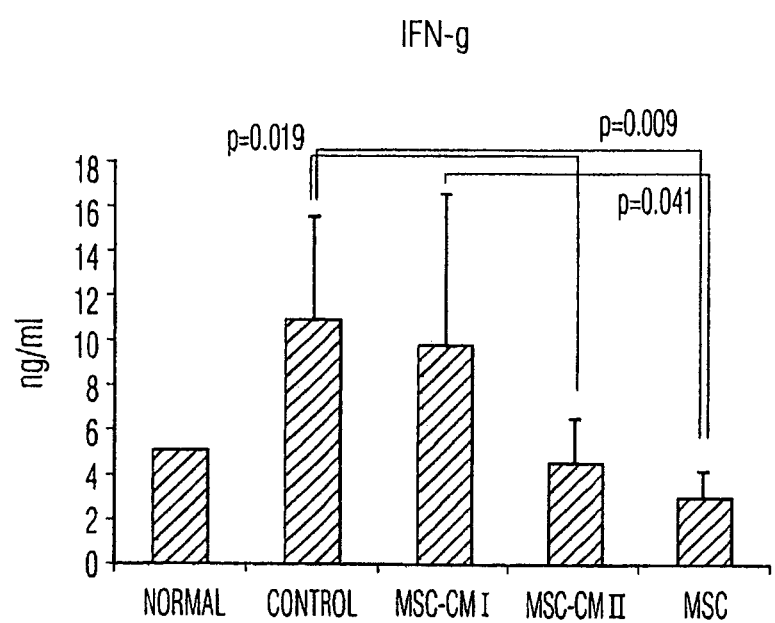
Figure 5C:
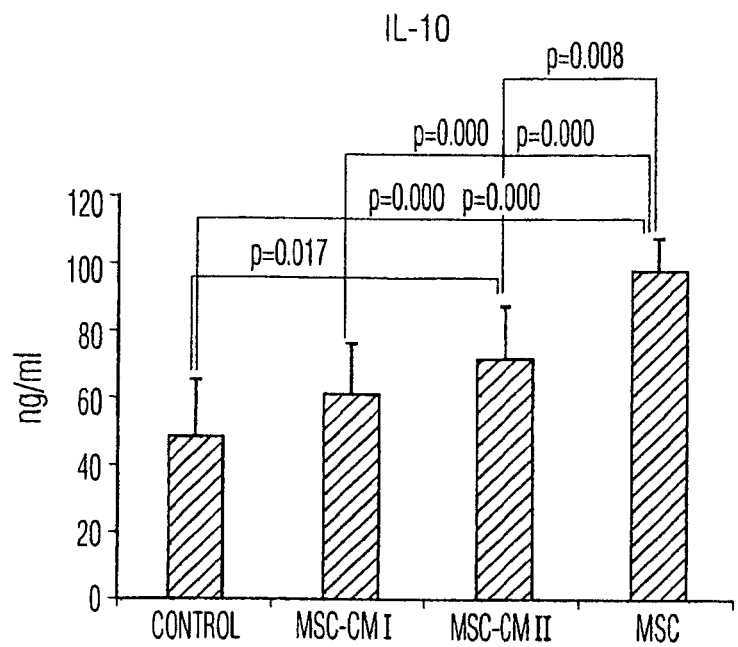
Figure 5D:
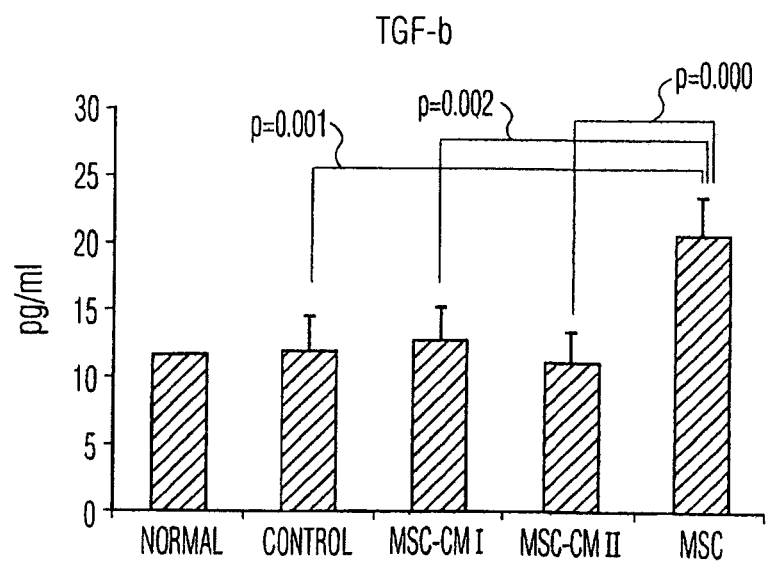
Figure 6A:
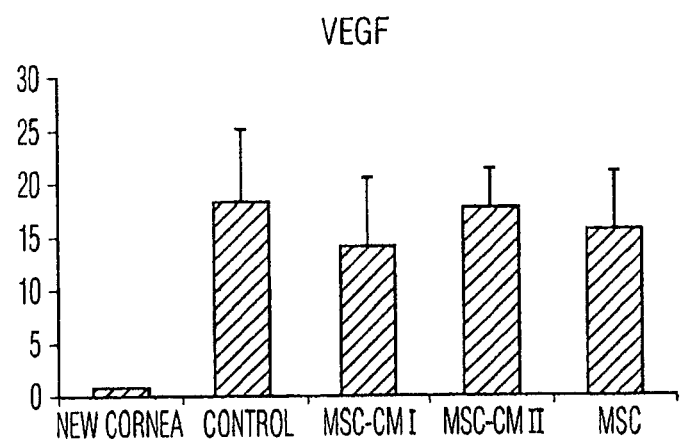
FIGS. 6A through 6D, is a series of images depicting real-time PCR for angiogenesis-related cytokines. Upregulation of TSP-1 was observed in the corneas treated with MSC or MSC-conditioned media three times (MSCCM II), compared to the control. MMP-2 and MMP-9 were downregulated in the MSC group. There were no differences in the expression of VEGF. Values were expressed as folds relative to fresh corneas without an injury.
Figure 6B:
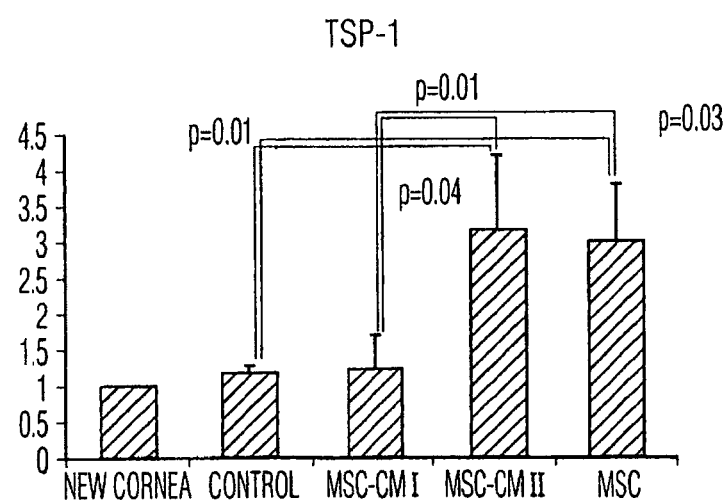
Figure 6C:
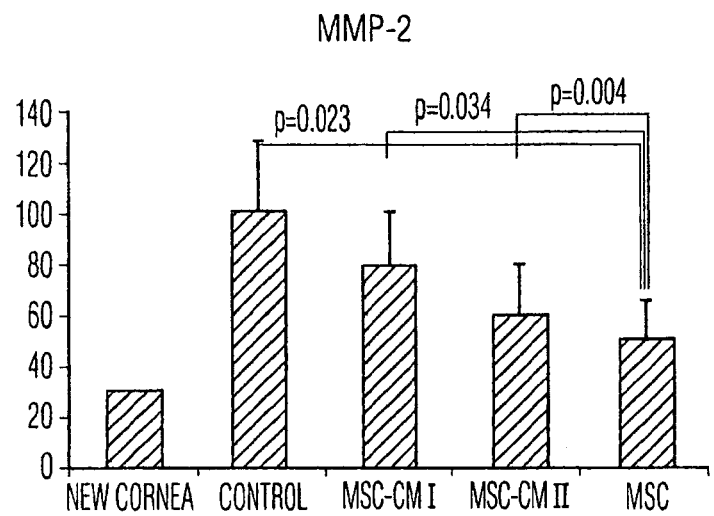
Figure 6D:
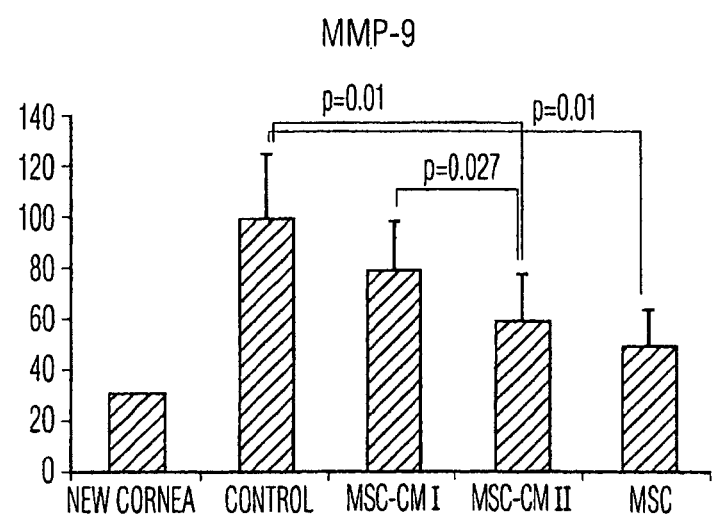

Similar to clinical findings, histological analysis (FIG. 4) revealed that MSCs and MSC-CM II groups had fewer inflammatory cell infiltrates than the control and MSC-CM I groups. Comparisons between MSCs and MSC-CM II groups showed that corneas treated with MSCs had significantly fewer inflammatory cells than those treated with MSC-CM three times.

ELISA showed that production of proinflammatory cytokines IL-2 and IFN-µ was decreased in MSC- and MSC-CM-treated corneas (FIG. 5 A, B). In contrast, large quantities of anti-inflammatory cytokines IL-10 and TGF-B were detected in MSC-treated corneas (FIGS. 5 C, D)

In order to determine the mechanisms associated with regression of new vessels by MSCs, the expression of angiogenesis-related cytokines, TSP-1, MMP-2, MMP-9, and VEGF was evaluated. Real time PCR revealed that the level of an anti-angiogenic factor, TSP-1, was significantly upregulated in MSC and MSC-CM II groups (FIG. 6). The expression of pro-angiogenic factors, MMP-2 and MMP-9, was significantly repressed in MSC-treated corneas, compared to control corneas.

Example 2

Figure 7:
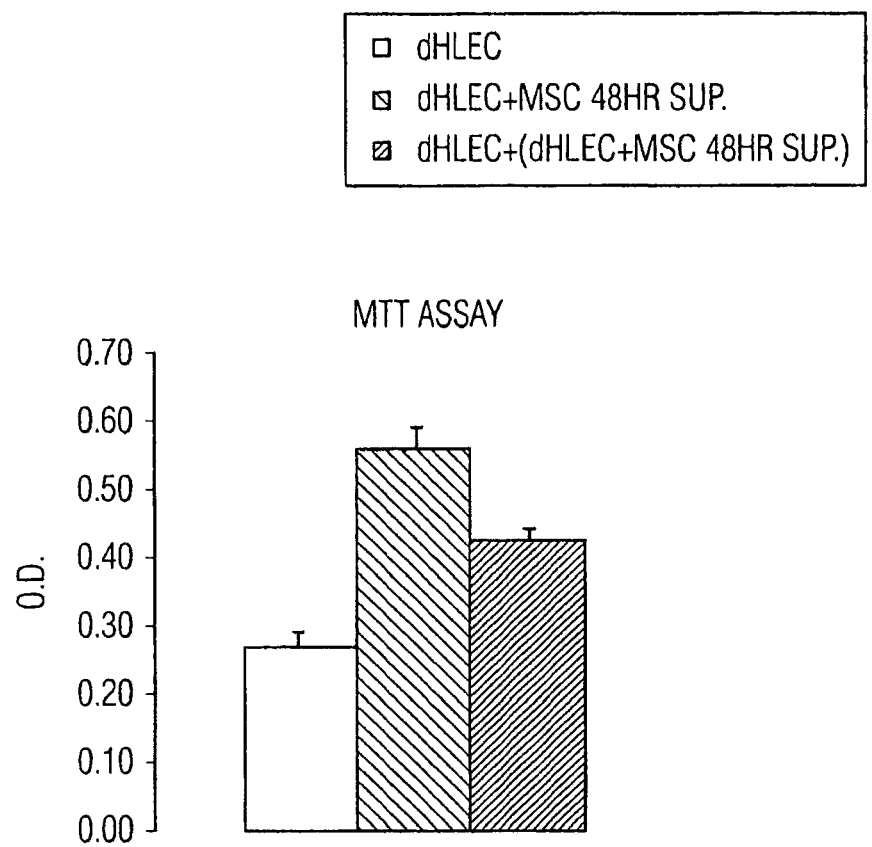
FIG. 7 is an image depicting cytotoxicity test of human corneal epithelial cells (HLECs) after chemical damage. When cultured with hMSCs-derived medium for 48 hours, damaged HLECs were significantly decreased compared to HLECs without hMSCs-conditioned medium.

Human MSCs-conditioned Media Rescued Human Corneal Epithelial Cells from Chemically-induced Apoptosis Human corneal epithelial cells (hCECs) were chemically damaged by incubation in 15% ethanol for 30 seconds. Damaged hCECs were cultured with one of the following: (1) hMSCs-conditioned media, (2) conditioned media from hMSCs-damaged hCECs coculture, or (3) fresh media. Then, survival of hCECs was evaluated with MTT assay. The result showed that the proportion of damaged hCECs was significantly decreased when cultured with hMSCs-conditioned media (FIG. 7).

Example 3

Figure 8:
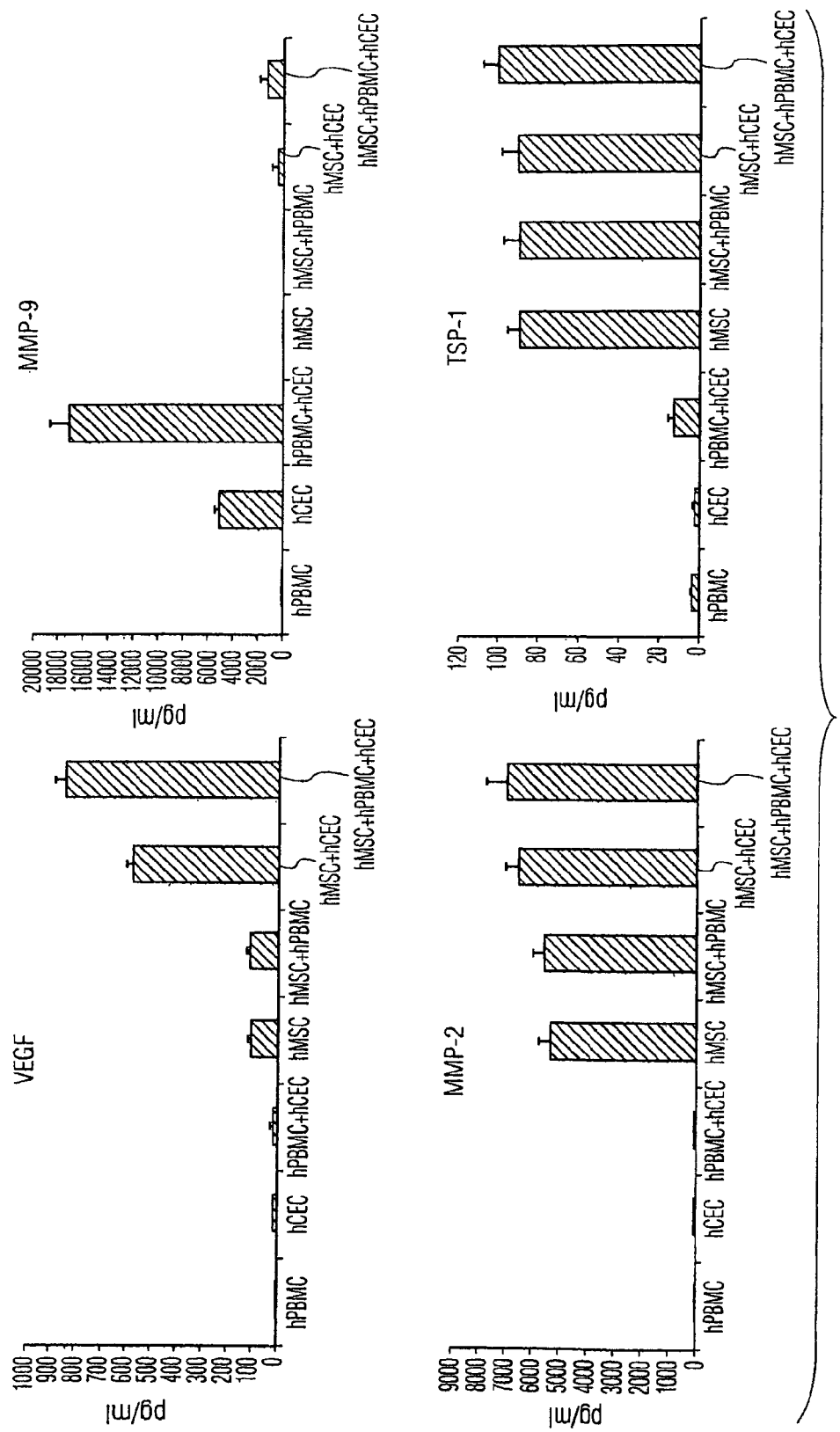
FIG. 8 is an image depicting cytokine secretion evaluated by ELISA. The expression of VEGF, MMP-9, MMP-2, and TSP-I were quantified in various cocultures of hMSCs/hCECs/hPBMCs. The hCECs were prepared after treatment with 15% ethanol for 30 sec. Data represent at least three experiments.

Production of MMP-9 is Significantly Suppressed in Chemically-damaged Human Corneal Epithelial Cells by hMSCs The following experiments were performed to evaluate how MSCs affected corneal epithelial cells in terms of inflammatory and angiogenic cytokine secretion. The hCECs were chemically damaged, then they were cocultured with hMSCs for 24 hours, and finally the cell-free supernatant was analyzed for cytokine concentration by ELISA. The coculture groups were as follows: (I) hPBMCs (human peripheral blood mononuclear cells), (2) hCECs, (3) hPBMCs/hCECs, (4) hMSCs, (5) hMSCs/hPBMCs, (6) hMSCs/hCECs, and (7) hMSCs/hPBMCs/hCECs. As a result, it was observed that MSCs constitutively secreted VEGF, MMP-2, and TSP-1 (FIG. 8). It is important to note that MMP-9, which is highly secreted by damaged hCECs, was significantly suppressed by hMSCs (FIG. 8, upper right). In fact, as a consequence of hMSC suppression the level of MMP-9 was reduced from 100% to 8%. Based on these results, it was believed that the suppression of MMP-9, a key player in corneal inflammation, angiogenesis, and wound healing would be one of the mechanisms responsible for MSC action during corneal regeneration. MMP-9 is one of the pro-inflammatory proteases that has its activation significantly inhibited by TSG-6 (Milner and Day, 2003; Milner et al., 2006).

The results presented herein demonstrate that application of either MSCs or conditioned medium from the MSCs decreased inflammation and neovascularization in a rat model for noninfectious inflammation of the cornea. Without wishing to be bound by any particular theory, the beneficial effects of the MSCs are at least in part explained by the effects of decreasing the levels of inflammatory cytokines and inflammation-related proteases both in the rat model of corneal damage and in cocultures with conical epithelial cells. Therefore the data are consistent with the hypothesis that the beneficial effects of MSCs are explained by the production by the cells of the anti-inflammatory protein TSG-6 and/or the anti-apoptotic protein STC-1.

Example 4

Use of Pre-Activated MSCs for the Treatment of Cornea

The following experiments were designed to test whether MSCs preactivated in culture to express therapeutic proteins would be more effective in reducing inflammation and neovascularization following chemically-induced injury to the cornea than standard cultures of MSCs. The experiments were set up to compare standard preparations of MSCs with MSCs pre-activated in culture with TNFα (FIGS. 10 C and D) in the rat model in terms of the minimum number of cells required to produce (a) significant improvements in neovascularization, opacity, epithelial defects, and infiltration of inflammatory cells as in FIGS. 3 and 4; (b) significant decreases in the inflammatory cytokine IFN-µ (FIG. 5); and (c) significant decreases in the inflammation related proteases MMP-2 and MMP-9 (FIG. 6). In parallel standard preparations and pre-activated MSCs by intracameral injection (IC; into anterior chamber) in the model are compared using the same measures of effectiveness.

As summarized in Table 1, the initial experiments are carried out with both rat MSCs and human MSCs (hMSCs), since the hMSCs are more relevant to the potential clinical applications of the results, and human and rodent MSCs have proven to be equally effective in other rodent models (Lee et al., 2009; Block et al.; 2009; Ohtaki et al., 2008; Iso et al., 2007; Ortiz et al., 2007; Lee et al., 2006; Munoz et al., 2006).

TABLE 1

|   | MSCs | Delivery | Dose | # Rats |
|---|---|---|---|---|
| 1. Species | hMSCs | Topical | $2 \times 10^4$ | 10 |
|   |   |   | $2 \times 10^5$ | 10 |
|   |   |   | $2 \times 10^6$ | 10 |
|   | rMSCs | Topical | $2 \times 10^4$ | 10 |
|   |   |   | $2 \times 10^5$ | 10 |
|   |   |   | $2 \times 10^6$ | 10 |
| 2. Route | hMSCs | IC | $2 \times 10^3$ | 10 |
|   |   |   | $2 \times 10^4$ | 10 |
|   |   |   | $2 \times 10^5$ | 10 |
|   | rMSCs | IC | $2 \times 10^3$ | 10 |
|   |   |   | $2 \times 10^4$ | 10 |
|   |   |   | $2 \times 10^5$ | 10 |
| 3. acMSCs | Ac h/rMSCs | Topical | $2 \times 10^4$ | 10 |
|   |   |   | $2 \times 10^5$ | 10 |
|   |   |   | $2 \times 10^6$ | 10 |
|   | Ac h/rMSCs | IC | $2 \times 10^3$ | 10 |
|   |   |   | $2 \times 10^4$ | 10 |
|   |   |   | $2 \times 10^5$ | 10 |
|   |   |   | Total | 180 |

The materials and methods employed in the experiments disclosed herein are now described.
Corneal Surface Inflammation Model Corneal surface inflammation can be created in rats by application of 100% ethanol and mechanical debridement of corneal and limbal epithelium using the protocol described in Oh et al. (2008). This model induces the infiltration of neutrophils, macrophages, neovascularization, and delayed wound healing in cornea (Figure. 1).
MSC's—Human MSCs (hMSC5) and rat MSCs (rMSCs) can be acquired from standardized preparations currently being distributed by our NIH/NCRR funded center (P40 RR 17447). For hMSCs, the standardized cells can be further screened to select preparations that are over 90% positive for PODXL. PODXL serves as a marker for MSCs that are likely to express other epitopes (c-MET, CXCR4, and CXC3CR1) for early progenitors in vivo. For rMSCs, MSCs can be isolated from the bone marrow of Lewis rats (Javazon et al., 2001).
Route of Treatment Delivery Topical application (FIG. 2) and IC injection are compared. This comparison allows for the determination of whether IC injection is effective at lower doses than topical application. For topical delivery, a hollow tube can be applied to the cornea, the cells (200 µL) can be put into the tube, and allowed to remain in the cornea for two hours (FIG. 2). The dose of cells can be varied from $2 \times 10^4$ to $2 \times 10^6$, the dose previously found to be effective (FIGS. 3 to 6). Topical application can be repeated on consecutive days for a total of three treatments. For IC injection, the media (5 µL) can be injected once into the anterior chamber of the rat eye. The dose of cells can be varied from $2 \times 10^3$ to $2 \times 10^5$, i. e. to the maximal concentration that can be employed without aggregation of the cells (Lee et al., 2009).
Assays for Corneal Surface Regeneration The eyes are examined with slit-lamp biomicroscopy and recorded with photography once a week. The clinical outcome is graded by a blinded investigator who is an ophthalmologist under the following criteria; (1) corneal epithelial integrity, (2) transparency, and (3) neovascularization (NV). A 1% fluorescein sodium solution can be used to evaluate the degree of corneal epithelial defects. Subsequently, defects are quantified by the ratio of epithelial defect area to total corneal area, using an image analyzer. The corneal clarity are graded from 0 to 4 using the method in Fantes et al., (1990) and Oh et al., (2008). The corneal NV are quantified by calculating the area of vessel growth with the method used in D'Amato et al. (1994), Oh et al. (2008), and Oh et al. (2009b). After three weeks, corneas are excised, and examined using appropriate assays discussed elsewhere herein.
Assays for Corneal Inflammation Corneas are either stained with hematoxylin-eosin or subjected to immunostaining with neutrophil- and macrophage-specific markers. The numbers of inflammatory cells are counted on the H&E-stained slides, The numbers of positively-stained cells are counted on the immunostained slides. Also, the infiltration and accumulation of neutrophils in the cornea are quantitated by measuring myeloperoxidase (MPO) activity with the MPO sandwich ELISA assay (Armstrong et al., 1998).
Assays for Modulation of Inflammation-, Angiogenesis-, and Apoptosis-related Molecules The expression of proteins for inflammation-related factors (IL-1B, IL-2, IFN-µ, IL-6, IL-10, TGF-B1), angiogenesis-related factors (TSP-1, VEGF), apoptosis-related factors (Fas/Fas ligand), and gelatinases (MMP-2, MMP-9) are measured in corneas using ELISA assay.

The results of these experiments are now described. Without wishing to be bound by any particular theory, it is believed that (1) hMSCs are as effective in a rat model of corneal inflammation as rMSCs; (2) the pre-activated MSCs are more effective than the standard preparations of MSCs; (3) one-time IC injection of MSCs are effective at lower doses than topical application.

It is possible that human proteins from hMSCs may not be as effective in the rat model as rMSCs. However, it is believed that hMSCs are as effective as rMSCs, because proteins are highly conserved across species, and it has been previously found that hMSCs worked in various murine models of inflammation (Lee et al., 2009; Block et al.; 2009; Ohtaki et al., 2008; Iso et al., 2007; Ortiz et al., 2007; Lee et al., 2006; Munoz et al., 2006). However, if it is observed that hMSCs are ineffective in rats, rMSCs can be used instead of hMSCs.

MSCs activated with TNF-α may either be ineffective or may produce toxic effects in cornea. It has been observed in preliminary experiments that the activation of hMSCs with TNF-α significantly upregulated some factors to modulate inflammation and other factors to increase cell survival (Lee et al., 2009). However, if TNF-α activation is found ineffective, MSCs can be pre-activate with IFN-μ, IL-1B, or their combinations as reported previously (Ren, et al., 2008). If ineffective, unmodified MSCs can be used for further experiments.

Example 5

Inflammation and Neovascularization of the Cornea can be Reduced by Application of Two of the Therapeutic Proteins Produced by Activated MSCs: The Anti-inflammatory Protein TSG-6 and the Anti-apoptotic Protein STC-1

The following experiments were designed to assess the effectiveness of using TSG-6 and STC-1 for treating inflammation and neovascularization of the cornea. Administration of recombinant proteins is an alternative to administering MSCs to the mammal in need thereof. The experiments are carried out as summarized in Table 2.

TABLE 2

| Expt. | Protein | Delivery | Dose | # Rats |
|---|---|---|---|---|
| 1. | TSG-6 | Topical | 1 μg | 10 |
| | | | 10 μg | 10 |
| | | | 100 μg | 10 |
| 2. | STC-1 | Topical | 1 μg | 10 |
| | | | 10 μg | 10 |
| | | | 100 μg | 10 |
| 3. | TSG-6 + STC-1 (1:1) | Topical | 1 μg | 10 |
| | | | 10 μg | 10 |
| | | | 100 μg | 10 |
| 4. | TSG-6 | IC | 0.1 μg | 10 |
| | | | 1 μg | 10 |
| | | | 10 μg | 10 |
| 5. | STC-1 | IC | 0.1 μg | 10 |
| | | | 1 μg | 10 |
| 6. | TSG-6 + STC-1 (1:1) | IC | 0.1 μg | 10 |
| | | | 1 μg | 10 |
| | | | 10 μg | 10 |
| | | | Total | 180 |

Briefly, recombinant TSG-6 (R & D Systems, Minneapolis, Minn.), recombinant STC-1 (BioVendor Laboratory Medicine, Inc.; Czech Republic), and their combinations are applied, respectively, to rat eyes using an appropriate delivery method. If topical application is used, the doses of TSG-6 can be varied from 1 to 100 μg (Lee et al., 2009). Alternatively, if IC injection is used, dosage from 0.1 to 10 μg can be used. The same range of doses are also tested with recombinant STC-1. The maximally effective dose of each protein are determined. Then the proteins are prepared in 1:1 mixtures and the maximally effective dose again are determined.

Without wishing to be bound by any particular theory (I) administration of either TSG-6 or STC-1 is effective in suppressing corneal inflammation and promoting epithelial wound healing in a dosage-dependent manner; (2) alternatively, administration of 1:1 mixtures may be effective at lower doses because of synergistic effects of the proteins; (3) intracameral administration of either or both proteins may be effective in lower doses than topical application.

Example 6

Novel Therapeutic Factors Produced by hMSCs in Response to Corneal Injury

The invention is not limited to only TSG-6 and STC-1. That is, the currently available data do not exclude the hypothesis that MSCs produce their beneficial effects on tissue repair by expression of other therapeutic genes. Therefore, experiments can be designed to test for additional therapeutic genes expressed by MSCs in the rat model for corneal injury. As indicated in the accompanying scheme set forth in FIG. 14, the experiments can be carried out in three complementary phases: Phase I: use hMSCs in the rat model for corneal injury, isolate the total RNA from the treated corneas and assay the total RNA on species-specific microarrays followed by filtering the data from cross-hybridization of the probes. Phase II: repeat the in vivo experiments using rat MSCs that express GFP (available from our NCRR/NIH center for distribution of MSCs), enzymatically digest the samples of cornea, isolate the GFP-expressing rMSCs by FACS sorting, and analyze the RNA with a rat-specific microarray. Phase III: carry out co-culture experiments in transwells with injured corneal epithelial cells (FIGS. 7 and 8) so that the RNA from the MSCs and the target cells can be isolated separately. The microarray data from the three phases of the experiments can be used to identify candidate therapeutic genes using the following criteria: (i) genes upregulated by hMSCs or rMSCs by incubation with injured cornea or corneal epithelial cells, (ii) genes for secretory proteins, and (iii) genes whose functions suggest that they may have anti-inflammatory or immunosuppressive effects. Verifying the roles of the candidate genes can be done using real-time RT-PCR, ELISAs or Western blots, knock down of the specific genes in MSCs with siRNAs or lentiviruses, blocking antibodies, and replacement of the MSCs by the recombinant proteins (FIGS. 10 through 13).

The materials and methods employed in the experiments disclosed herein are now described.

Assays for hMSCs in the Rat Model for Corneal Injury

Figure 9A:
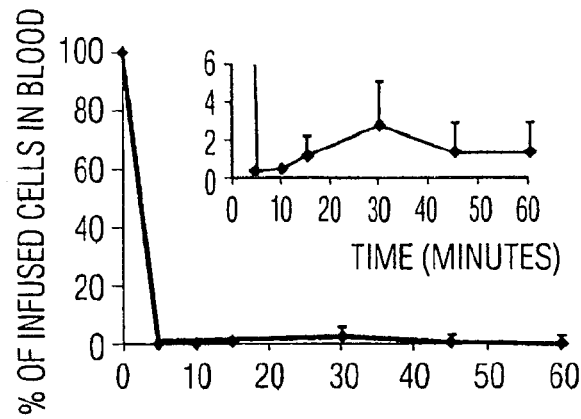
FIGS. 9A through 9F, is a series of imaged depicting assays for fate of hMSCs infused into mice.
Figure 9B:
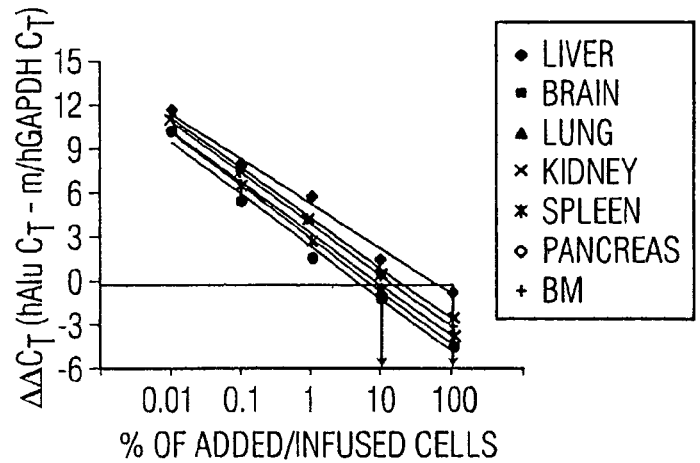
Figure 9C:
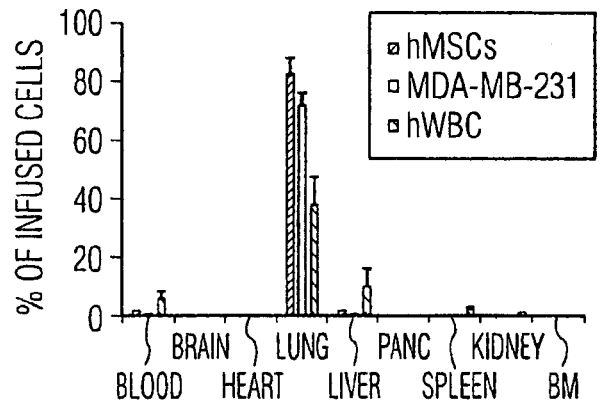
Figure 9D:
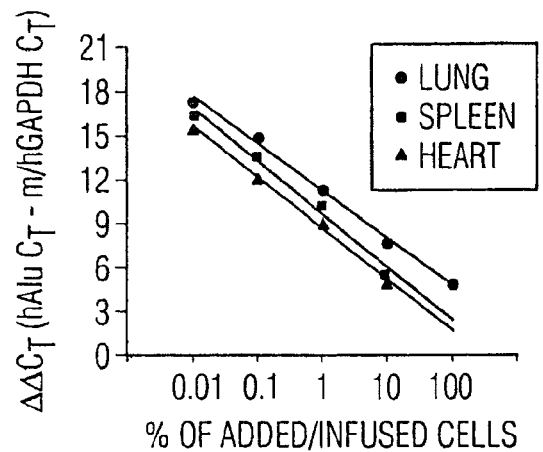
Figure 9E:
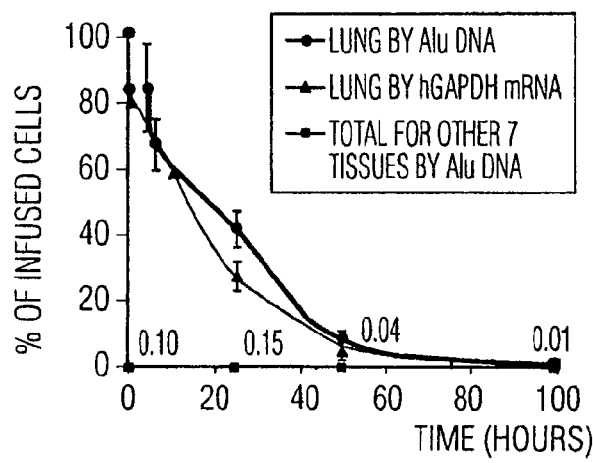
Figure 9F:
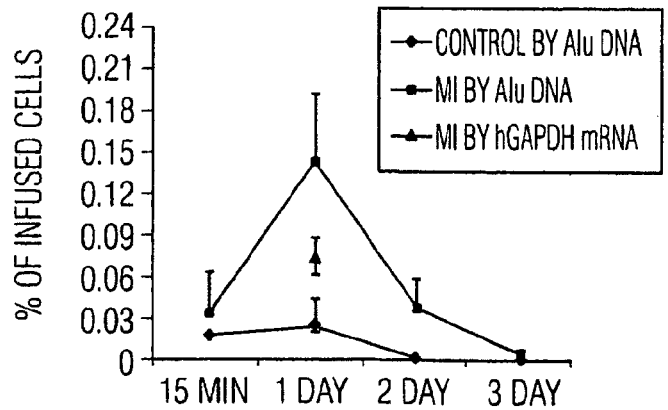
Figure 10A:
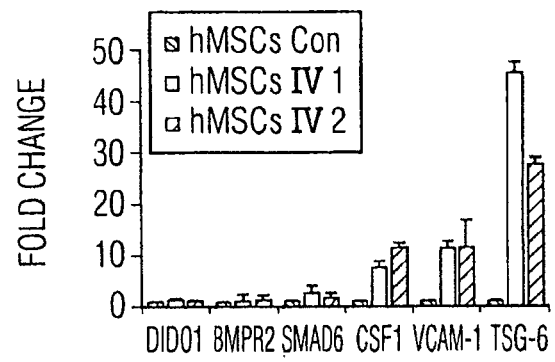
FIGS. 10A through 10F, is a series of images depicting activation of hMSCs to Express TSG-6.
Figure 10B:
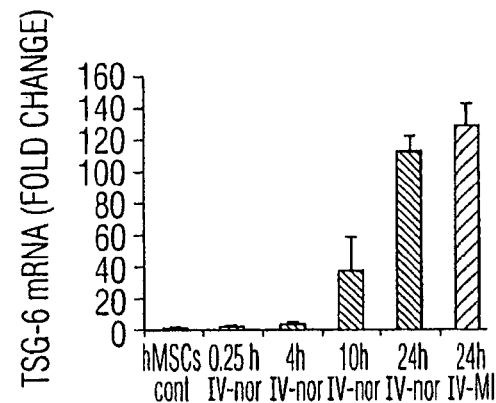
Figure 10C:
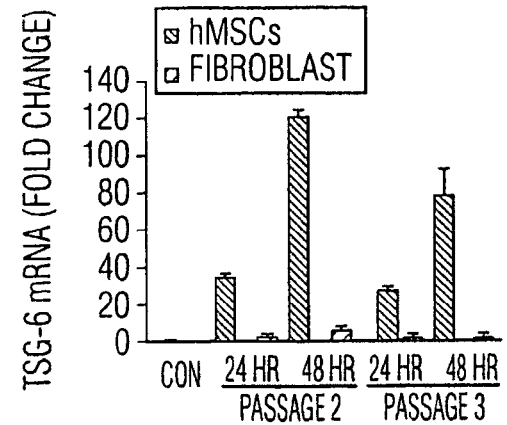
Figure 10D:
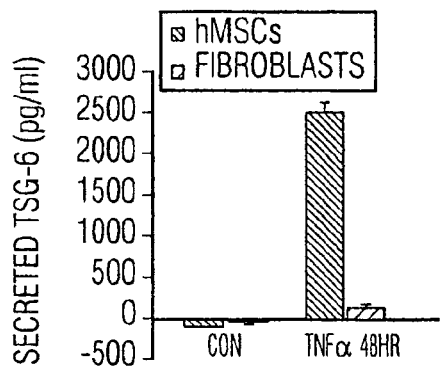
Figure 10E:
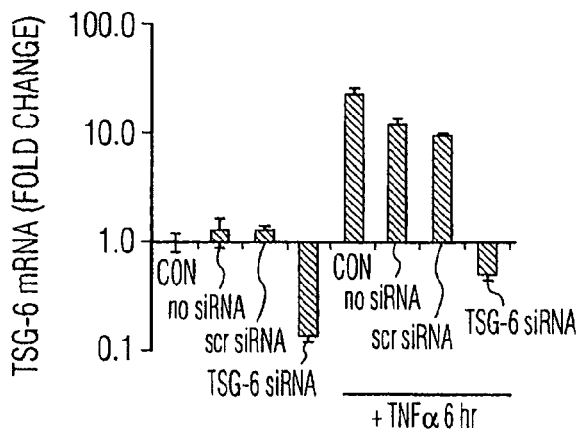
Figure 10F:
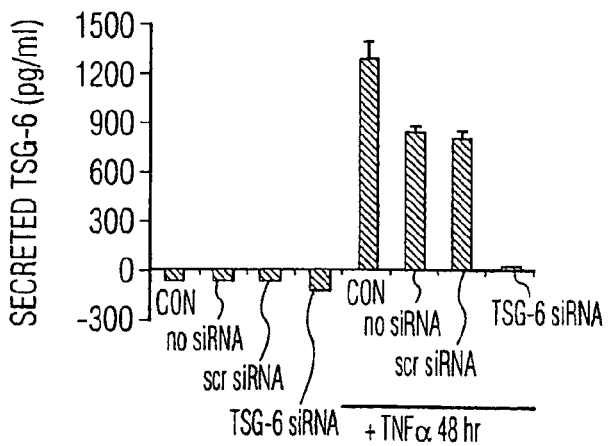
Figure 11A:
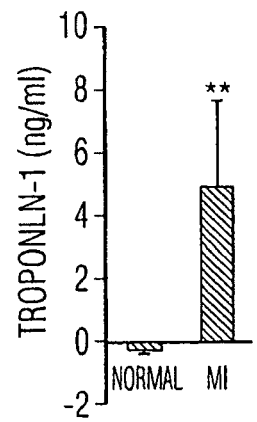
FIGS. 11A through 11E, is a series of images depicting assays of serum and heart.
Figure 11B:
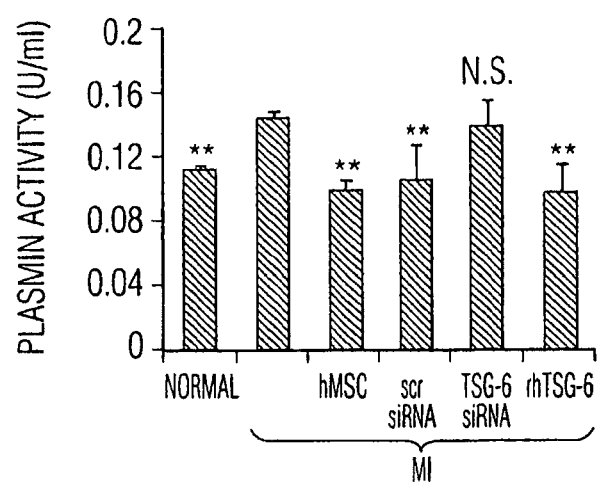
Figure 11C:
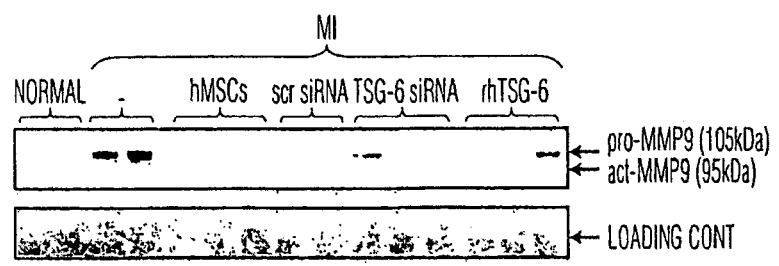
Figure 11D:
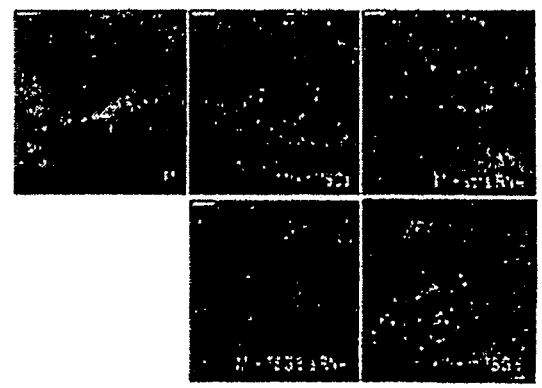
Figure 11E:
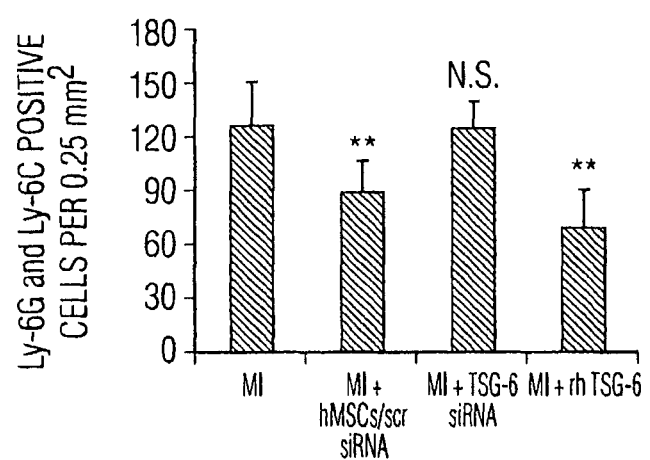
Figure 12F:
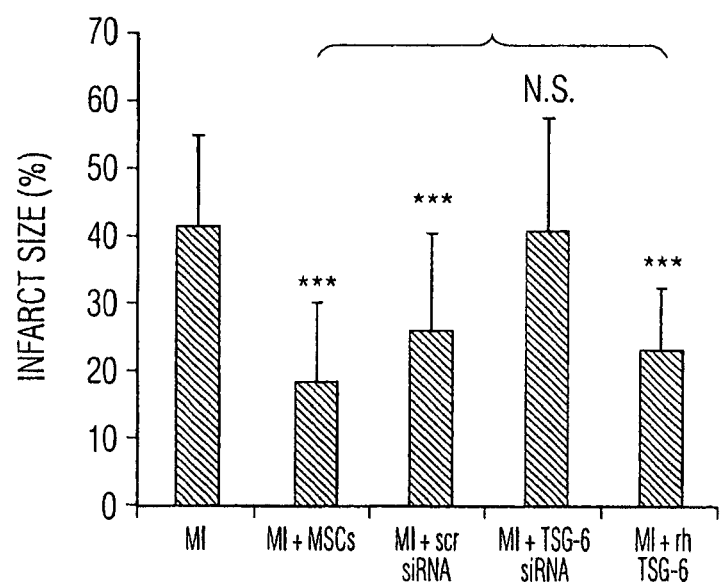

Immediately after injury, the hMSCs ($2 \times 10^6$ cells/200 μl) are placed into an applicator and allowed to remain in the damaged cornea for two hours (FIG. 2A). Eyelids are sutured for rats not to blink in order to prevent the shedding of transplanted cells. One day, one week, two weeks, and three weeks later, the corneas are excised, homogenized (PowerGen; Fisher Scientific), extraction of DNA (Phase Lock Gel; Eppendor/Brinkmann Instruments) and the DNA assayed for the highly repetitive Alu sequences, unique to the human genome, to follow the fate of hMSCs in rat eyes (FIG. 9B). The use of Alu sequences provides a highly sensitive assay since there are about 500,000 copies per cell. However, preliminary experiments indicated that use of conventional procedures greatly overestimated the content of human cells. Therefore, an improved protocol based on the chemical assay for extracted DNA and standard curves for real-time PCR of each tissue is used, The assay for Alu sequences is complemented with a less sensitive assay extracted RNA (Trizol reagent, Invitrogen) human mRNA for GAPDH in order to assay live human cells in the rat tissues (FIG. 9D). The results provide quantitative data on the engraftment of the hMSCs.

Assays of Human and Rat mRNAs in Cornea by Microarrays

To examine the changes occurring in hMSCs applied in injured rat cornea and the changes in rat cornea caused by hMSCs, RNA will be isolated from cornea (Trizol; Invitrogen), and assayed on both rat and human microarrays (Affymetrix, Santa Clara, Calif.). Data will be filtered for cross-hybridization (Ohtaki et al., 2008; Lee et al., 2009), analyzed with the dChip program, and normalized to a variance of 2 SD. For cross-hybridization, we need three control groups: (i) uninjured rat cornea treated with vehicle, (ii) injured rat cornea treated with vehicle, and (iii) uninjured rat cornea treated with hMSCs. After an analysis of human genes upregulated 2 fold or more in hMSCs, we will select candidate genes to confirm the data by human-specific real-time RT-PCR assays.

Real-time PCR and ELISA Analysis

To determine whether the candidate genes are upregulated in cultured hMSCs, real-time PCR is performed in cultured hMSCs. Double stranded cDNA is synthesized (SuperScript III; Invitrogen) and analyzed by real time PCR (ABI 7900, Sequence Detector; Applied Biosystems). Human-specific primers are obtained from commercial sources or designed from gene sequences. The data is further verified by human-specific ELISA assays either from commercial sources or with kits developed from commercial antibodies. Alternatively, expression of the proteins are verified by Western blots where antibodies are available.

Figure 13:
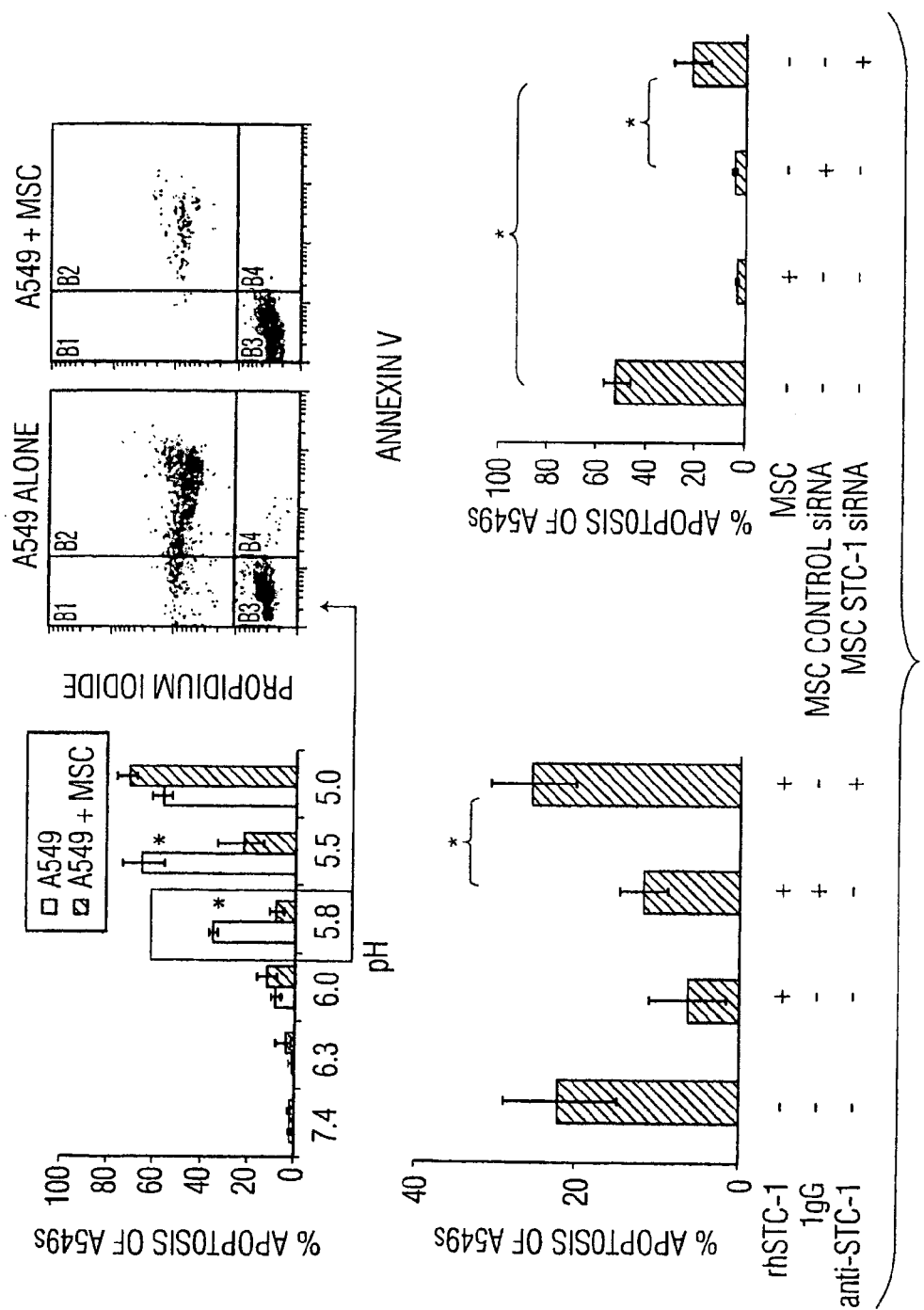
FIG. 13 is an image demonstrating that STC-1 was required and sufficient for reduction of apoptosis of lung epithelial cell line made apoptotic by incubation at low pH in hypoxia. Upper left and right: Cultures of A549 cells became apoptotic when incubated for 24 hours in 1% oxygen at pH 5.8 or 5.5. However, coculture of A549 cells in transwells with MSCs reduced the apoptosis. Lower left: Apoptosis of A549 cells was inhibited by rhSTC-1, and the effects were reversed by anti-STC-1 antibodies. Lower right: MSCs transduced with siRNA for STC-1 were less effective than control MSCs in decreasing apoptosis of A549 cells in the transwell experiment.
Figure 14:
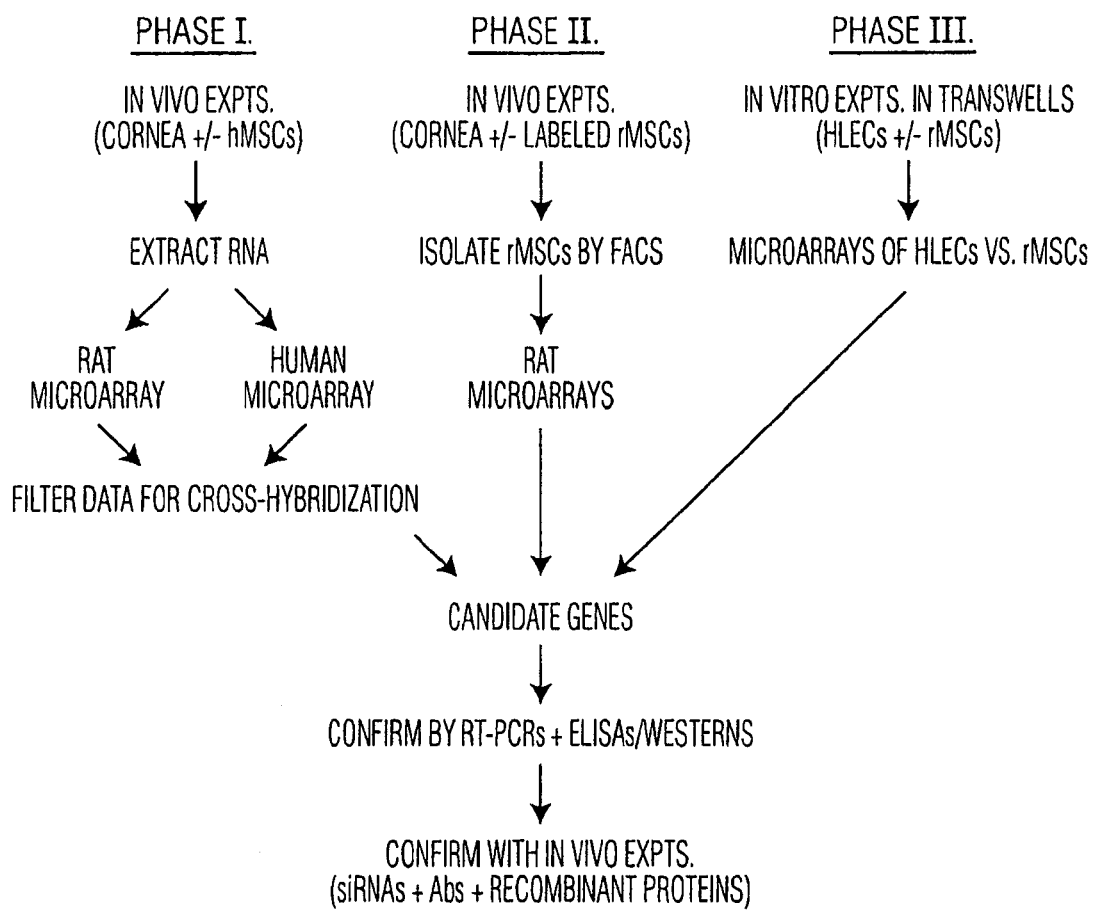
FIG. 14 is a schematic of a strategy to search for additional, novel therapeutic factors produced by hMSCs in response to corneal injury.

Confirmation with Recombinant Protein, siRNA, and Blocking Antibodies

Where recombinant protein is available for the candidate gene selected above, the protein is applied in a rat model to assess whether the protein mimics the effects of MSCs. In addition, MSCs with a knock down of the selected gene either with an siRNA or lentivirus is tested (FIGS. 11 E and F). Also, where blocking antibodies are available, they can be tested in the rat model (FIG. 13).

Assays from Co-culture in Transwells

The experiments are performed with both hMSCs and rMSCs as described in FIGS. 7 and 8. The separate cell fractions are first assayed with microarrays and the roles of candidate genes confirmed as above.

The results of these experiments are now described. Without wishing to be bound by any particular theory, it is believed that: (1) one or more of the additional cornea-protective genes can be identified from the microarray data; (2) the protein from the candidate gene(s) can be expressed at increased levels in the rat model and the co-cultures with injured lens epithelium; (3) the application of the candidate protein(s) is as effective in suppressing corneal inflammation as hMSCs; (4) both hMSCs not expressing the gene and hMSCs combined with blocking antibody fail to produce beneficial effects on rat model.

Example 7

The Anti-inflammatory and Anti-apoptotic Proteins from Adult Stem/Progenitor Cells (MSCs) Protect the Cornea from Injury by Preventing Apoptosis and Suppressing Inflammation The following experiments were designed to determine whether inflammation of the cornea can be reduced by application of two of the therapeutic proteins produced by activated MSCs: the anti-inflammatory protein TSG-6 and/or the anti-apoptotic protein STC-1.

Figure 15:
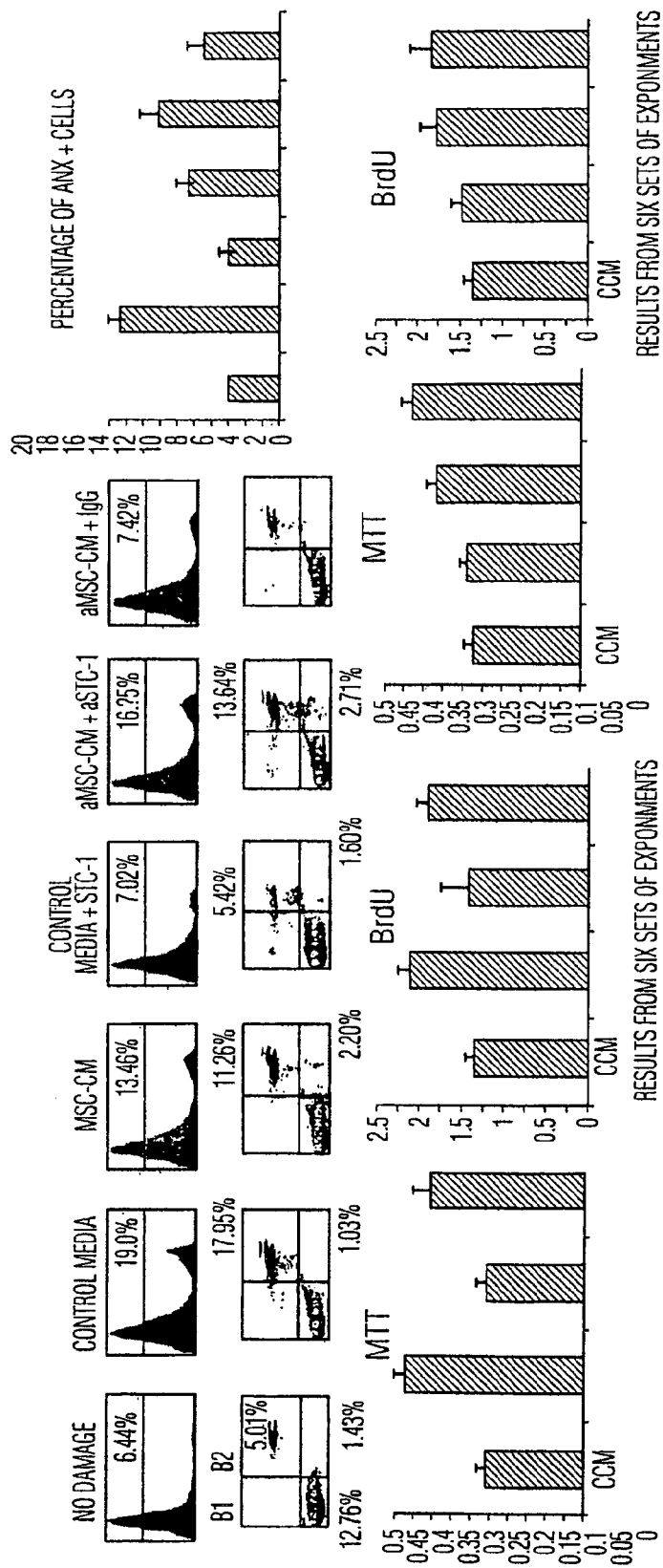
FIG. 15 is a series of imaged demonstrating that conditioned medium from pre-activated MSCs and rhSTC-1 had the greatest effects in hMSCs improving the viability, increasing the proliferation, and inhibiting the apoptosis of damaged hCEPs.
Figure 18:
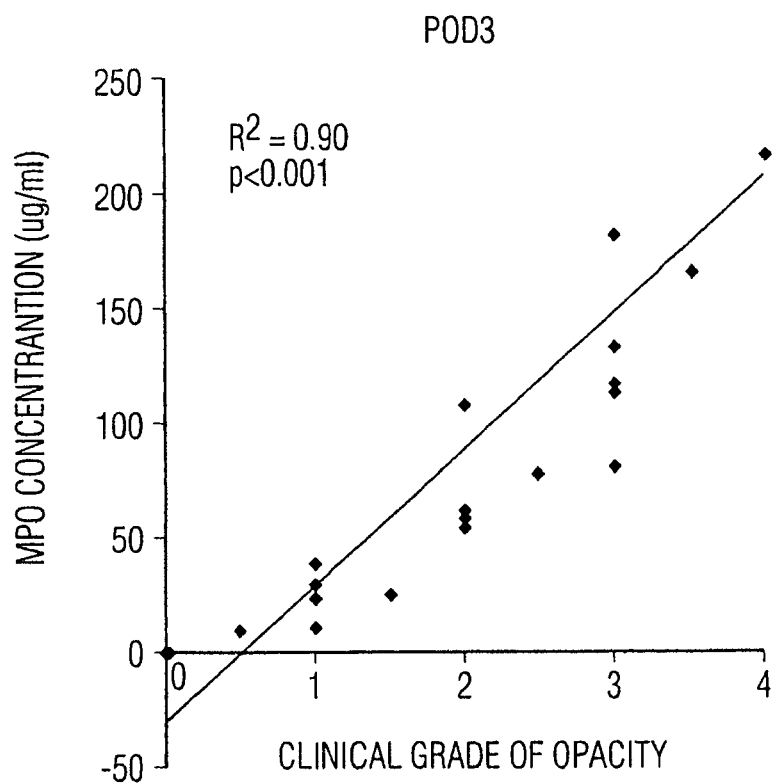
FIG. 18 is a graph depicting correlation between clinical opacity and MPO amount in cornea at post-injury 3 days.
Figure 19A:
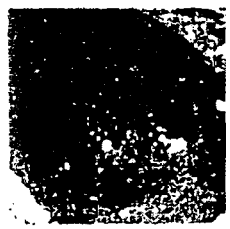
FIGS. 19A through 19D, is a series of images demonstrating that TSG-6 up to the concentration of 2 ug is effective in reducing corneal opacity, inflammation, and MMP-9 production.
Figure 19B:
Figure 19C:
Figure 19D:
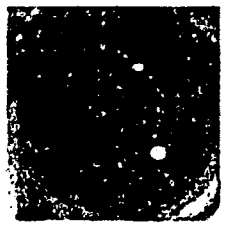
Figure 19E:
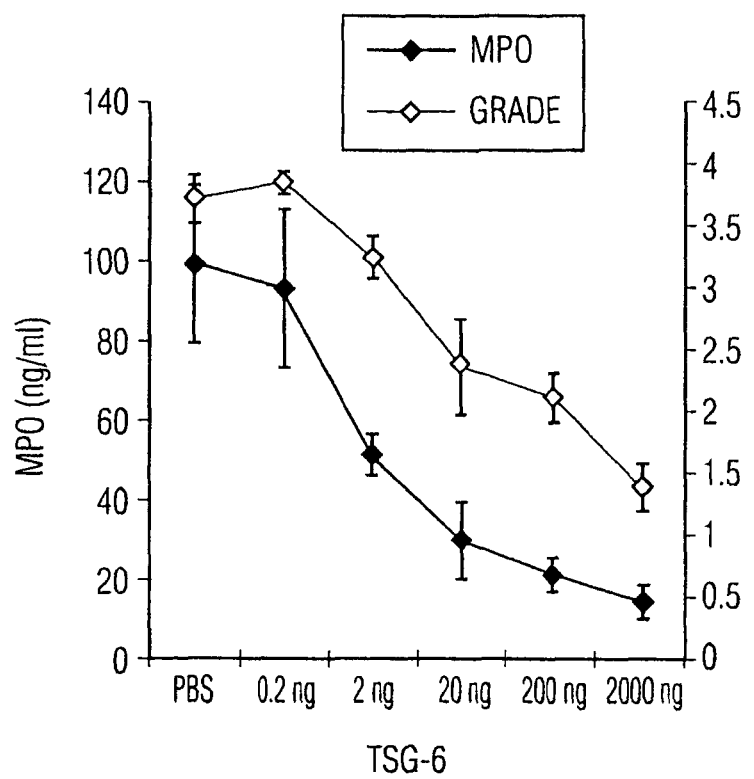
(FIG. 19E)
Figure 19F:
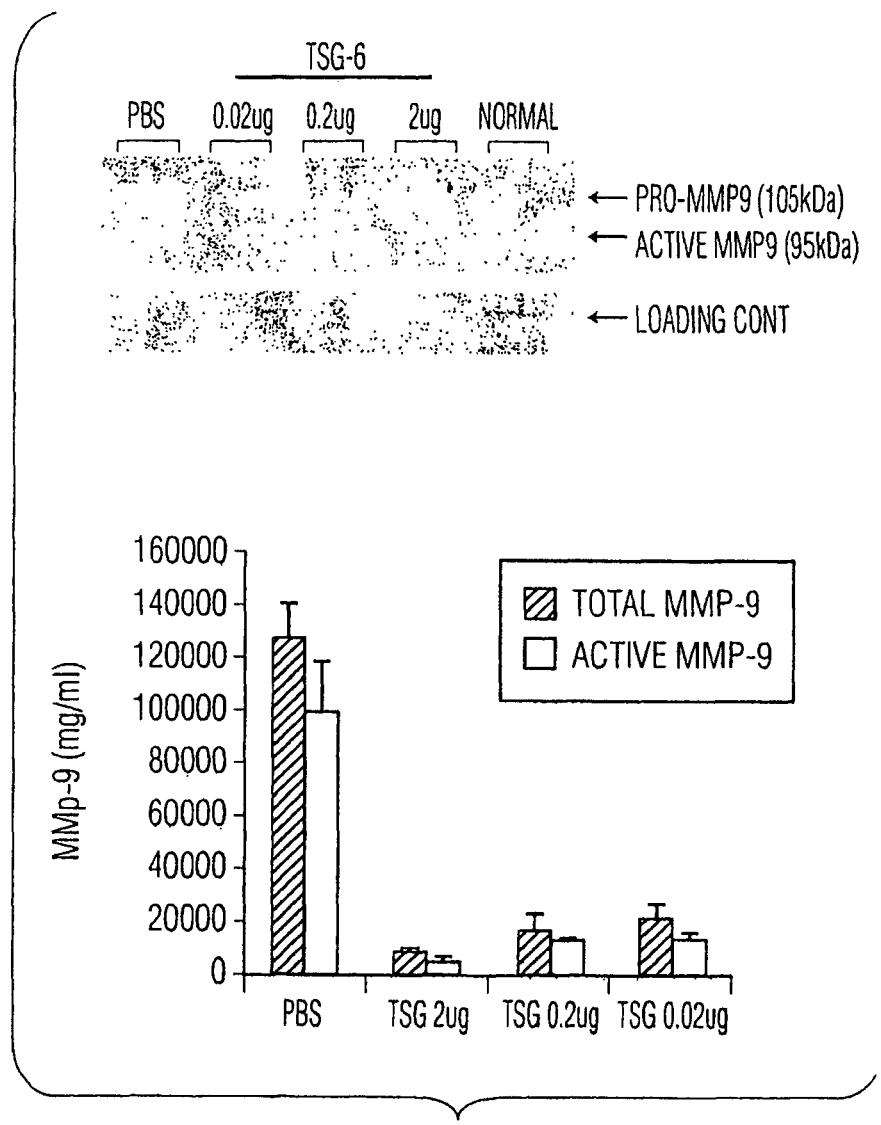
(FIG. 19F) Gel zymography and ELISA for MMP-9.

To test the anti-apoptotic effect of STC-1 in vitro, human corneal epithelial progenitor cells (hCEPs) after exposure to ethanol were cultured for 24 hours with one of the following: (a) conditioned medium from standard cultures of human MSCs (hMSCs), (b) conditioned medium from hMSCs pre-activated to express therapeutic factors by incubation with TNF-α for 24 hr, (c) rhSTC-1, (d) conditioned medium and blocking Ab against rhSTC-1, or (e) IgG. Both fresh medium and the medium conditioned from cultures of human dermal fibroblasts were used as controls. After incubation, the cell viability, proliferation and apoptosis were evaluated using MTT assay, BrdU uptake, and PI/annexin flow cytometry. It was observed that conditioned medium from pre-activated MSCs and rhSTC-1 had the greatest effects in hMSCs improving the viability, increasing the proliferation, and inhibiting the apoptosis of damaged hCEPs (FIG. 15).

Figure 20:
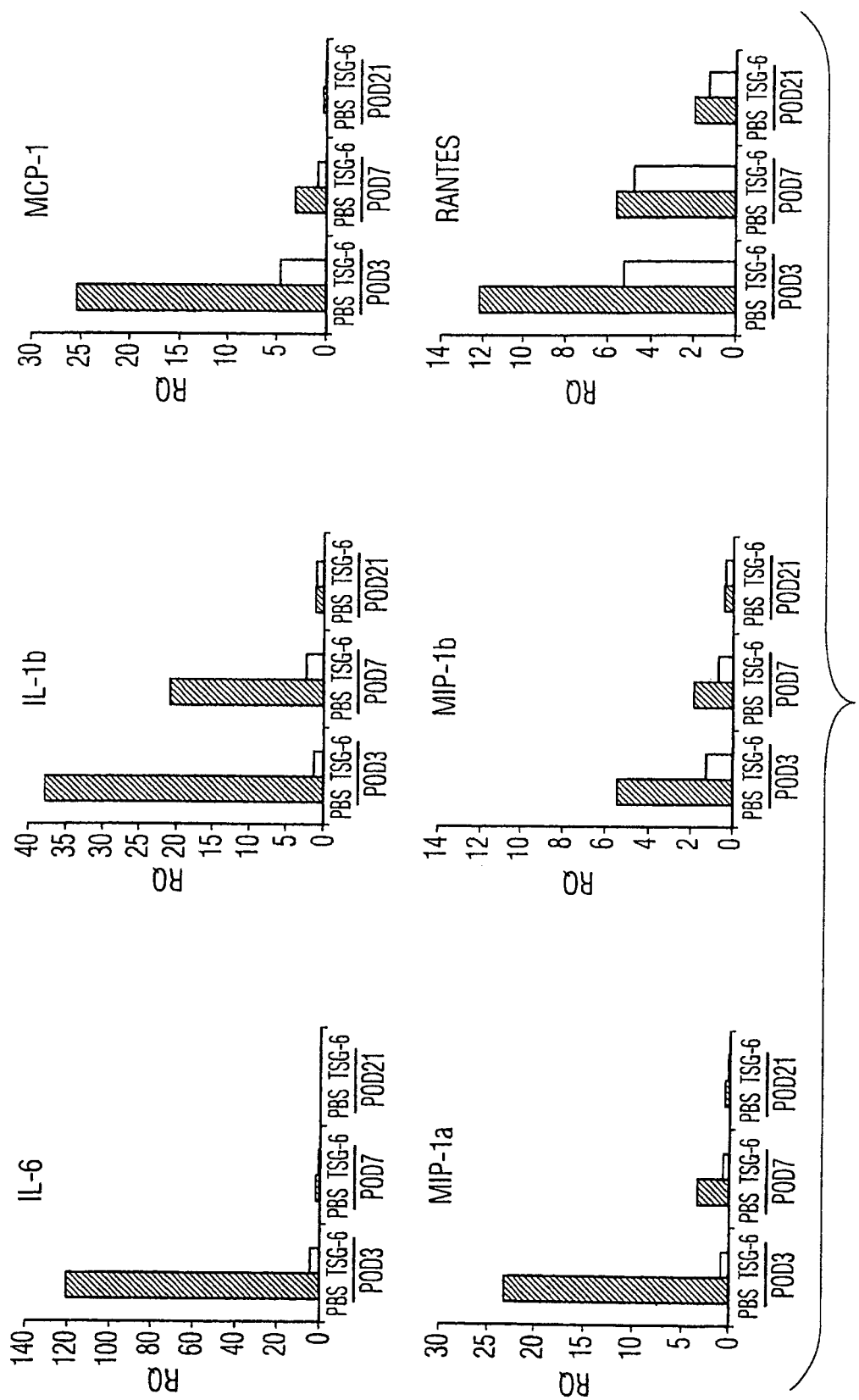
FIG. 20 is an image depicting real time PCR for inflammatory cytokines and chemokines. RQ: relative gene expression. Comparisons are between vehicle treatment (PBS) and TSG-6 treatment (2 micrograms) on post-operative days (POD) 3, 7, and 21.
Figure 21:
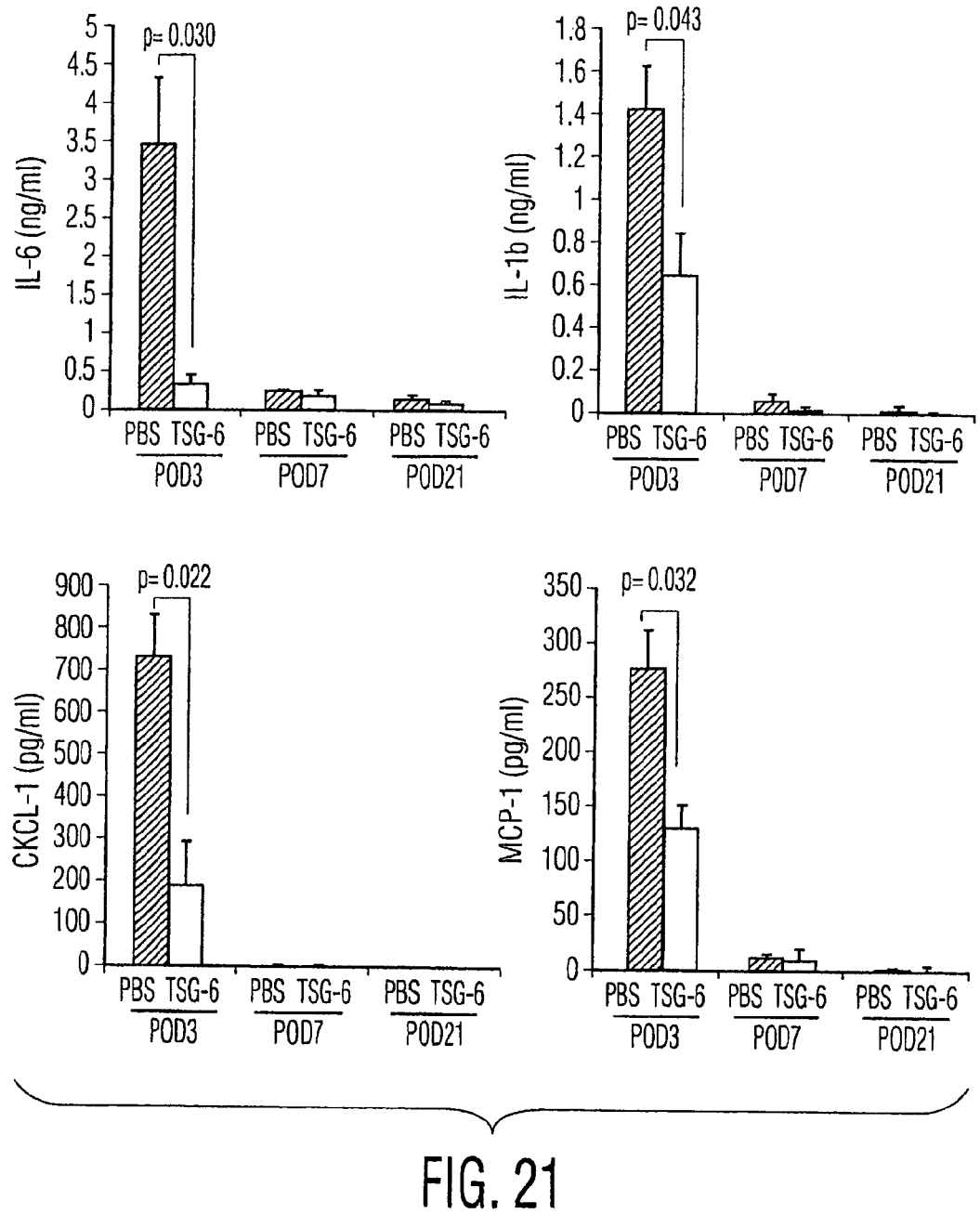
FIG. 21 is an image depicting ELISA for cytokines and chemokines. Conditions as in FIG. 20.
Figure 22:
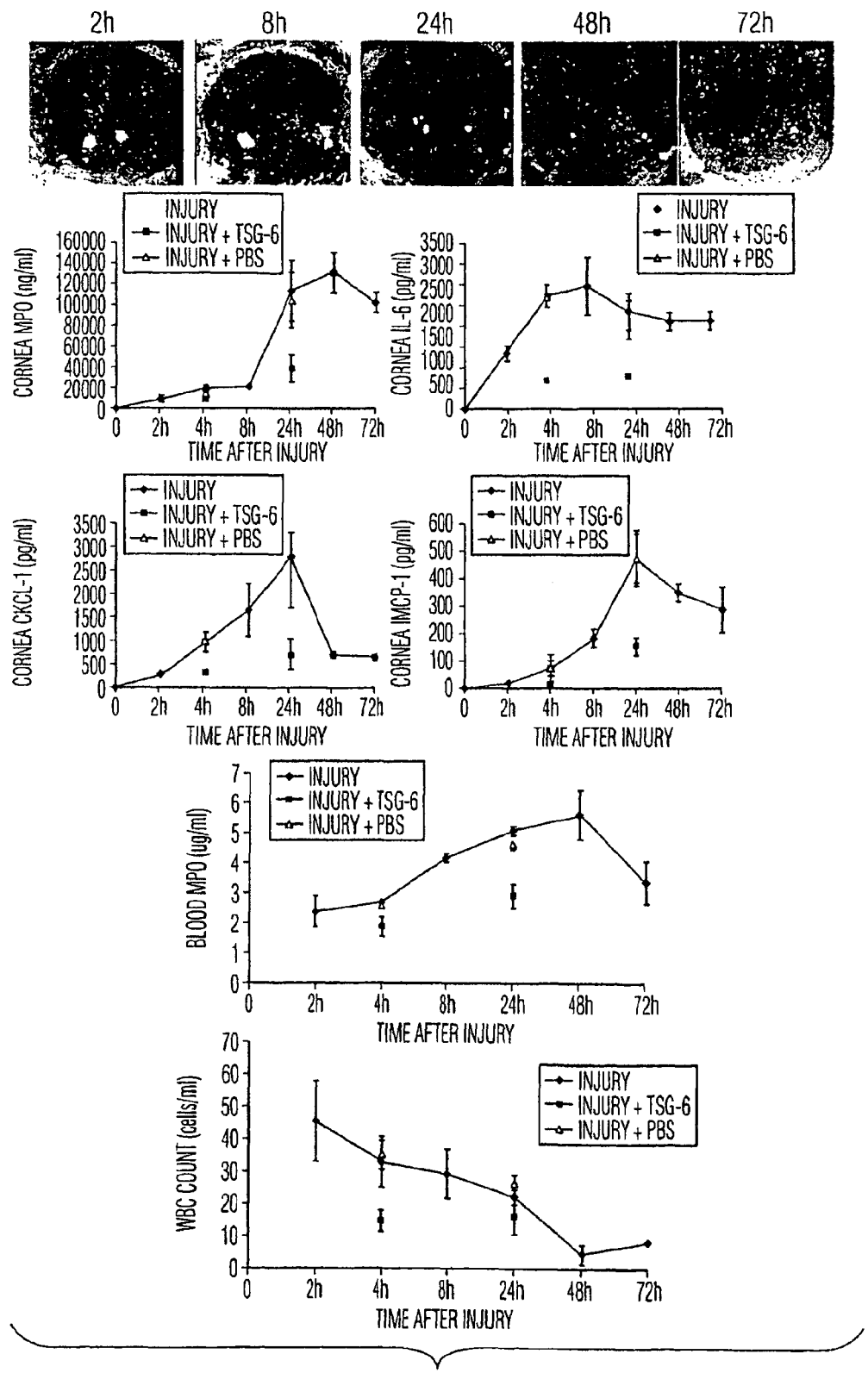
FIG. 22 is an image demonstrating that TSG-6 delayed the time neutrophils started to infiltrate and arrived at its peak as well as decreased the amount of infiltrated neutrophils. The expression pattern of chemokines and cytokines showed similar kinetics. Lower two frames: Blood levels of MPO and leukocytes (WBC).

To test the anti-inflammatory effect of TSG-6 in vivo, corneal surface inflammation was created in Lewis rats by ethanol application and mechanical debridement of corneal and limbal epithelium. Immediately after injury, rhTSG-6 (2 ng-2 ug) or the same volume of PBS was injected into the anterior chamber. Effects on the cornea were determined in three ways: (1) gross examination by slit-lamp biomicroscopy based on the findings of transparency and neovascularization (NV), (2) histological analysis for infiltration of inflammatory cell (hematoxylin-eosin staining), (3) myeloperoxidase (MPO) assay for infiltration of neutrophils, (4) ELISA and real time PCR for inflammation-related chemokines and cytokines, (5) Gel zymography and ELISA for total and active MMP-9. Changes in inflammatory markers in systemic circulation were also determined by WBC counting and serum MPG evaluation. It was observed that corneal opacity and neovascularization were significantly decreased in TSG-6-treated corneas compared to PBS-treated controls. (FIG. 16). The infiltration of inflammatory cells and expression of MMP-9 were significantly decreased in TSG-6-treated corneas compared to PBS-treated controls. (FIG. 17). It was also observed that TSG-6 up to the concentration of 0.002 ug/ml was effective in reducing corneal opacity, inflammation, and MMP-9 production (FIG. 19). Furthermore, it was observed that administration of TSG-6 decreased the expression of inflammatory cytokines and chemokines (FIGS. 20, 21, 22).

The results presented herein demonstrate that therapeutic proteins produced by MSCs in response to an injury signal can protect the corneal surface from damage by increasing the viability and proliferation of corneal epithelial progenitors and by suppressing inflammation in corneal surface.

Example 8

1. Potential of Adult Stem/Progenitor Cells (MSCs) and STC-1 as Anti-apoptotic Therapies in Degenerative Diseases of the Retina 1.1. MSCs Rescue Degenerative Diseases of the Retina. Bone marrow-derived rodent MSCs have been transplanted via subretinal injection in mouse and rat models of inherited retinal degenerations (Pan, et al., *Acta Biochem. Biophys. Sin* (Shanghai), Vol. 40, No. 3, pgs. 202-208 (2008); Inoue, et al, *Exp. Eye Res.*, Vol. 85, No. 2, pgs. 234-241 (2007); Arnhold, et al., *Graefe's Arch. Clin. Exp. Ophthalmol.*, Vol. 245, No. 3, pgs. 414-422 (2007); Kicic, et al., *J. Neurosci*, Vol. 23, No. 21, pgs. 7742-7749 (2003)). Anatomic preservation of the ONL was demonstrated by histologic analysis (Pan, 2008; Inoue, 2007; Arnhold, 2007). In addition, electroretinography (Inoue, 2007) demonstrated preservation of retinal function with MSC therapy. These published results using subretinally delivered rodent MSCs suggest a positive therapeutic effect for MSCs in the rescue of retinal degeneration. Although some studies emphasized the production of secreted factors (Inoue, 2007), the mechanism of action or secreted factors were not defined. Additionally, subretinal delivery of cell therapy has important drawbacks: retinal detachment following subretinal cell therapy (Pan, 2008) and the potential for only local rescue of photoreceptors at the injection site (Arnhold, 2007).

1.2. MSCs can Rescue Tissues by Secretion of the Anti-apoptotic Protein STC-1. The therapeutic benefit of adult stem/progenitors from bone marrow (mesenchymal stem cells, marrow stromal cells, MSCs) in various disease models has been known for some time (Prockop, *Science*, Vol. 276, pgs. 71-74 (1997); Prockop, et al; *Proc. Nat. Acad Sci.*, Vol. 100, Supp. 1, pgs. 11917-11923 (2003)). The cells can engraft and differentiate to replace injured cells but more frequently they produce functional improvements by being activated by signals from injured tissues to express therapeutic factors (Lee, *Cell Stem Cell* (2009)). Among the therapeutic factors produced by MSCs is the anti-apoptotic protein stanniocalcin-1 (STC-1). STC-1 was identified by our lab in experiments that tested the hypothesis that soluble factors secreted by MSCs could reduce apoptosis in an in vitro model of UV-irradiated skin fibroblasts. It was found that fibroblast apoptosis was reduced by transwell co-culture of MSCs. Microarray analysis detected increased expression of the anti-apoptotic protein Stanniocalcin-1 (STC-1) by MSCs, a finding that was later confirmed by Western Blot analysis. The results additionally were demonstrated when addition of an antibody against STC-1 inhibited the ability of MSCs to reduce apoptosis of UV-irradiated fibroblasts (Block, et al., *Stem Cells*, Vol. 27, No. 3, pgs. 670-681 (2009)). Additionally, recombinant human STC-1 was able to reduce hypoxia induced apoptosis in A549 cells (Block, 2009). One reported action of STC-1 that explains the anti-apoptotic and anti-necrotic effects of STC-1 is the uncoupling of oxidative phosphorylation that leads to a decrease in ROS production via induction of mitochondrial uncoupling protein 2 (UCP2) (Wang, et al., *J. Leukoc. Biol.*, Vol. 86, No. 4, pgs. 981-988 (2009)). Our collaborators also have confirmed recently that the anti-apoptotic effects of STC-1 seen in a lung cancer cell line are due to a UCP2 dependent ROS reduction (Ohkouchi et al, *Proc. Nat. Acad. Sci.*, in press). STC-1 also has been shown to be upregulated in neurons in response to cerebral ischemia in both rats and humans (Zhang, et al., *Proc. Nat. Acad. Sci.*, Vol. 97, No. 7, pgs. 3637-3642 (2000)) and to protect neuronal cells from hypoxia in vitro (Zhang, 2000). Other actions of STC-1 have been described, which include its ability to inhibit inflammation (Sheik-Hamad, et al., *Am. J. Physiol. Renal. Physiol.*, Vol. 298, No. 2, pgs. 248-254 (2010)) by inhibiting macrophage chemotaxis (Kanallis, et al., *Am. J. Physiol. Renal Physiol*. Vol. 286, No. 2, pgs. 356-362 (2004)), modulating transendothelial migration of leukocytes (Chakraborty, et al., *Am. J. Physiol. Renal Physiol.*, Vol. 292, No. 2, pgs. 895-904 (2007)), and reducing T-cell infiltration (Huang, et al., *Am. J. Pathol.*, Vol. 174, No. 4, pgs. 1368-1378 (2009)). These observations suggested that the therapeutic benefits of MSCs observed previously in models of retinal degeneration (Pan, 2008; Inoue, 2007; Arnhold, 2007) were explained by the cells' secreting STC-1 to decrease the apoptosis that is a prominent feature of the pathology in both animal models and patients (Dunaief, 2002; Xu, 1996; Cottet, 2009; Doonan, 2004, Yu, 2004; Katai, 1999; Katai, 2006).

This experiment employs (a) intravitreal administration of the anti-apoptotic protein STC-1 and human adult stem/progenitor cells that can be obtained readily from bone marrow to reduce photoreceptor death in the degenerating retina; and (b) a battery of highly sensitive assays and experimental protocols that have been used previously in order to elucidate the molecular and cellular mechanisms whereby MSCs produce their therapeutic benefits in other animal models of human diseases.

Approach

Aim 1. Test the Hypothesis that we can Improve Our Preliminary Results Using Intravitreal Administration of STC-1 in the Royal College of Surgeons (RCS) Rat Model of Retinal Degeneration by Optimizing the Dose, Time, and Frequency of Administration of STC-1.

Figure 23:
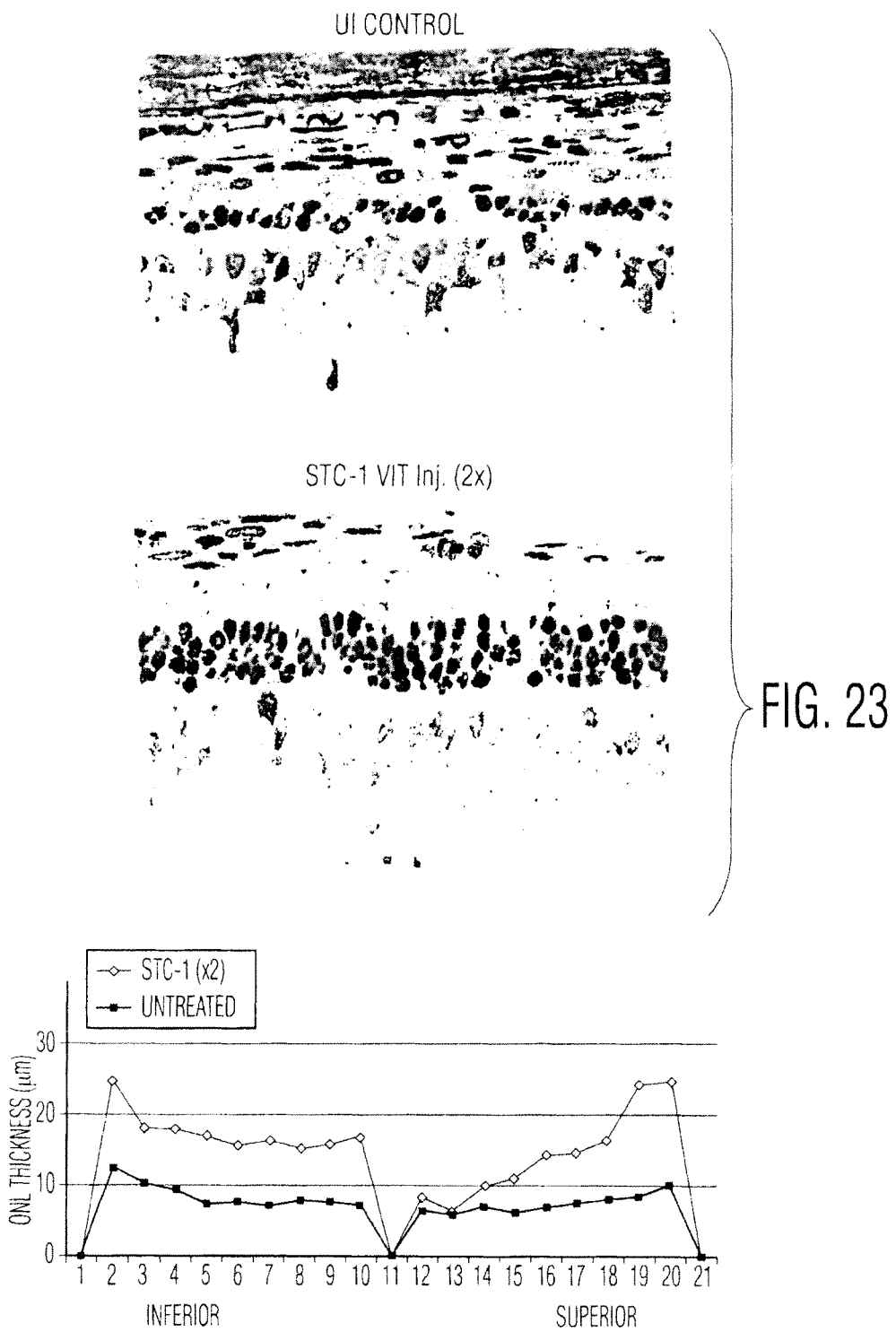
FIG. 23. Two injections of STC-1 rescued retinal degeneration in the rhodopsin mutant transgenic rat. Upper frame: representative posterior segment histology showed thickened ONL in STC-1 treated eyes compared to UI controls. The ONL is the outer nuclear layer of the retina that contains the nuclei of the rods and cones. Lower frame: representative plot of ONL layer thickness taken from a total of 54 measurements (27 superior retina and 27 inferior retina) demonstrated STC-1 significantly improved ONL thickness compared to UI controls.

1.1. Rationale. To determine whether intravitreal administration of STC-1 delays photoreceptor degeneration in vivo, two rodent models of retinal degeneration were used. S334ter-3 rhodopsin transgenic rats were treated at post natal day 9 (P9) and again at P12 with intravitreal injections of 1 µg STC-1. The rats were sacrificed at P19. Histologic analysis revealed increased outer nuclear (ONL) thickness compared to uninjected (UI) controls. Mean ONL thicknesses of inferior (inf), superior (sup), and total retina were quantified as described previously in Lewin, et al., *Nat. Med*. Vol. 4, No. 8, pgs. 967-971 (1998). Total retina ONL thickness was increased significantly in STC-1 treated rats (n=4, p=0.018) (FIG. 23).

Figure 24:
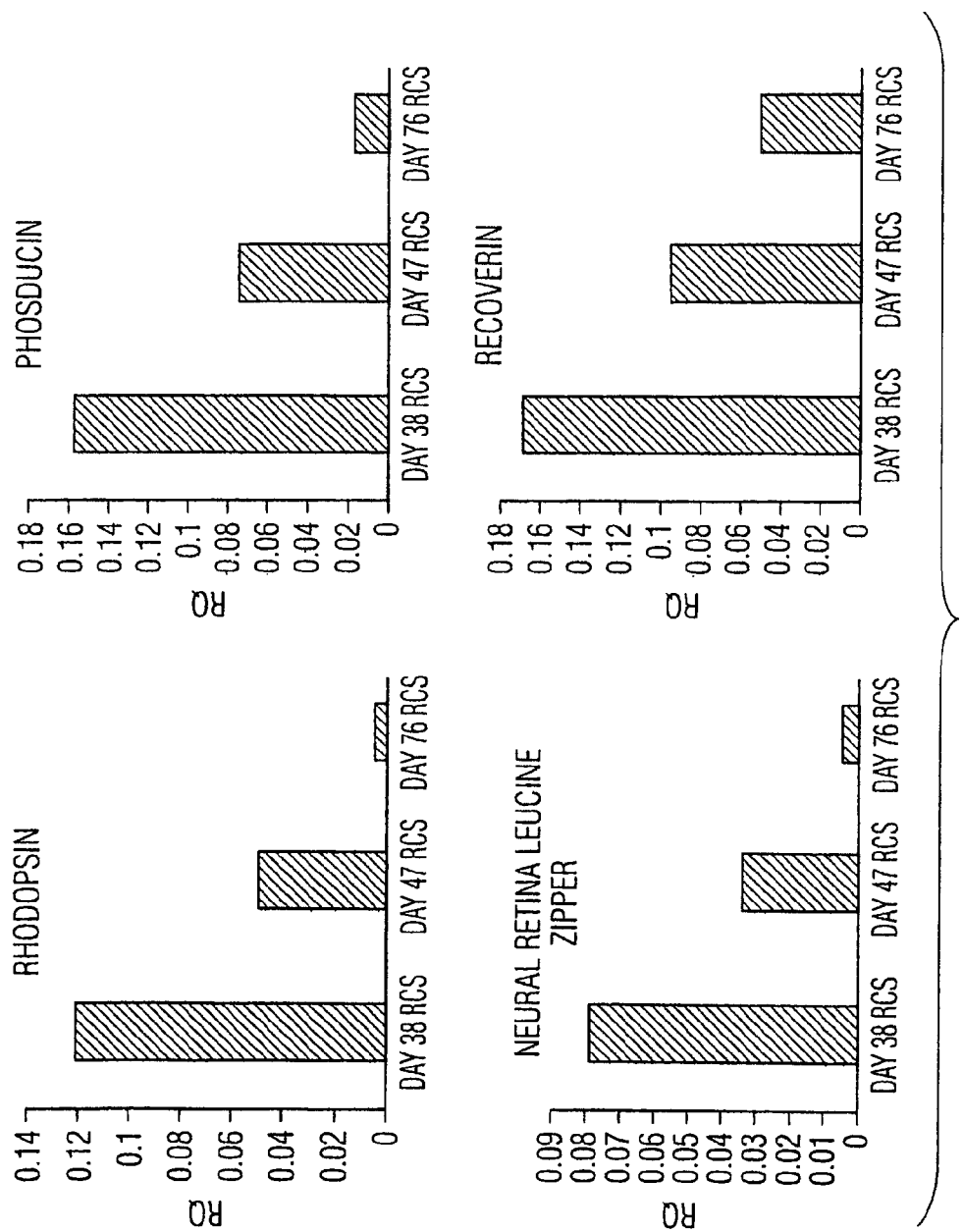
FIG. 24. Age related loss of mRNAs for photoreceptors in RCS rat. qRT-PCR analysis for the photoreceptor genes: rhodopsin, phosducin, neural retina leucine zipper, and recoverin. Expression of these genes decreases over time in the RCS rat. For qPCR methods see Lee, 2008.

Additionally, the Royal College of Surgeons (RCS) rat model of retinal degeneration was tested. As part of these studies, a gene expression assay was developed that could be used in conjunction with histologic and functional analysis to detect photoreceptor rescue. Expression of photoreceptor specific genes was tested by quantitative real-time PCR (qRT-PCR) in retinas isolated from RCS rats at varying timepoints. Photoreceptor gene expression was shown to decrease over-time in the RCS rat in rates comparable with the previously described decline of the ONL in LaVail, et al., *Exp. Eye Res.*, Vol. 21, No. 2, pgs. 167-192 (1975) (FIG. 24).

Figure 25:
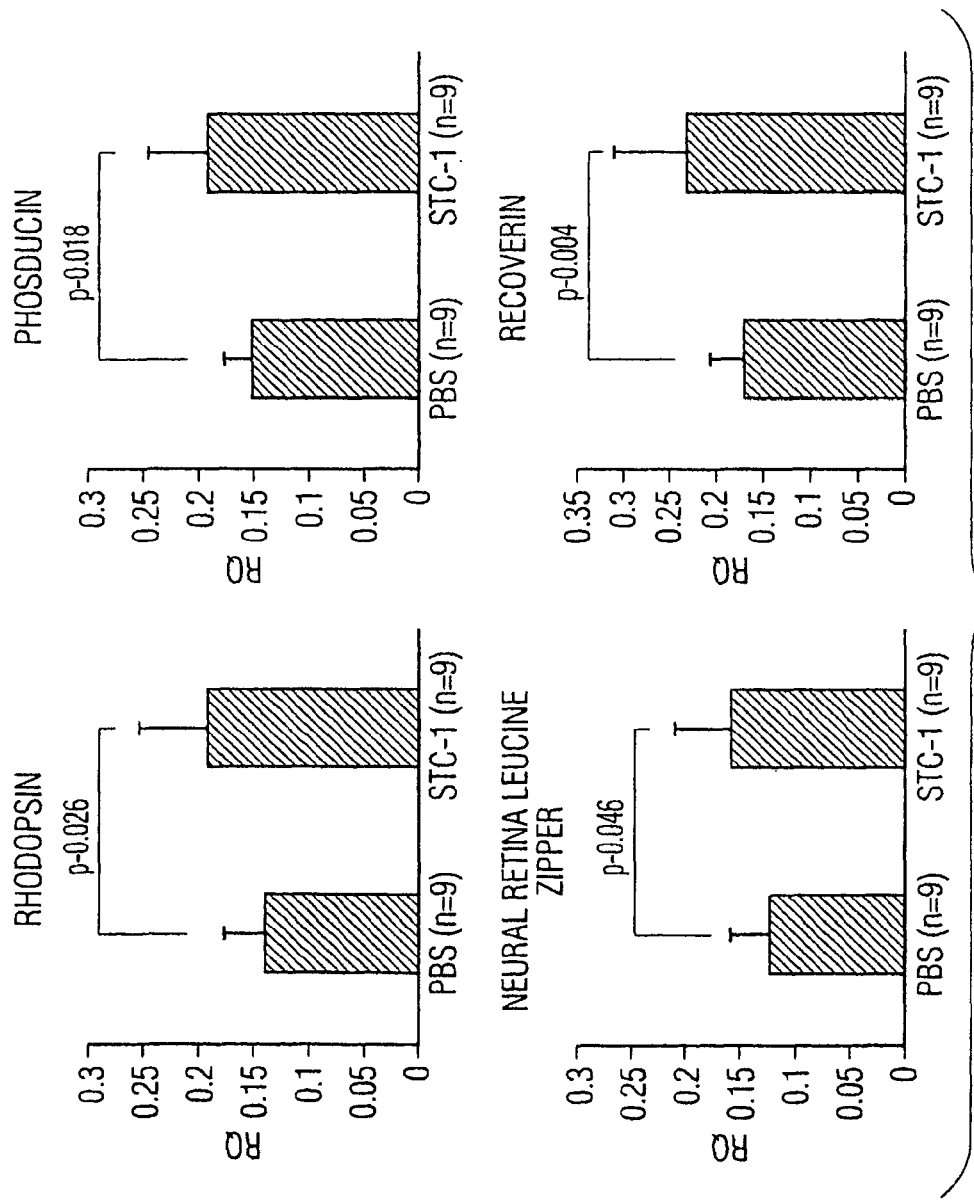
FIG. 25. Rescue of mRNAs for photoreceptors by intravitreal injection of STC-1 in RCS rat. qRT-PCR analysis for photoreceptor genes was conducted as described with respect to FIG. 24.

Utilizing this assay as a basis for quantification of photo-receptor viability, the hypothesis that intravitreal administration of STC-1 would improve photoreceptor viability was tested. Rats received an intravitreal administration of 2.5 µg STC-1. Injections occurred at P21, the approximate time of initiation of ONL decline (LaVail, 1975). The rats were sacrificed, and tissue was collected at P40. Total RNA from the retinas of the rats was extracted using the RNeasy mini kit. (Qiagen). cDNA was generated by reverse transcription (Super Script III; Invitrogen) using 1 µg total RNA. Real time amplification was performed using the Taq Man Universal PCR Master Mix (Applied Biosystems). An 18S rRNA probe (Taq Man) was used for normalization of gene expression. Gene expression analysis showed significant increases in photoreceptor gene expression in STC-1 treated animals compared to PBS injected controls. (FIG. 25).

1.2. Design. Intravitreal administration of STC-1 reduced photoreceptor degeneration in two rodent models of retinal degeneration. As described hereinbelow, the next set of experiments are directed to optimizing the dose, time of administration, and frequency of administration of STC-1 in the RCS rat.

1.2.1. Optimization of dose of STC-1. First, the dose of STC-1 which preserves photoreceptor viability most effectively (STC-1$^{OptD}$) is determined. The experiments are carried out as summarized in Table 3. For this experiment, STC-1 is injected at P21 and tissues are harvested at P40. The results are assessed on the basis of photoreceptor gene expression (see FIG. 24).

TABLE 3

Dose of STC-1. P21, postnatal day 21; P40, post-natal day 40. qRT-PCR, for photoreceptor genes as described in FIG. 24.; fellow eye, indicates the fellow (contralateral) eye is injected as an internal control.

| Therapy | Dose (μg) | Injection | Termination | Evaluations | No. (RCS Rat) |
|---|---|---|---|---|---|
| STC-1 | 2.5 | P21 | P40 | qRT-PCR | 6 |
| | 1.0 | P21 | P40 | qRT-PCR | 6 |
| | 0.5 | P21 | P40 | qRT-PCR | 6 |
| | 0.1 | P21 | P40 | qRT-PCR | 6 |
| | 0.05 | P21 | P40 | qRT-PCR | 6 |
| PBS | 0 | P21 | P40 | qRT-PCR | fellow eye |

Milestone: Optimal dose of STC-1 = STC-1$^{OptD}$.

In parallel Experiments, as outlined in Table 4 below, the optimal time of administration will be defined and whether two injections are more effective than one will be determined.

TABLE 4

Day of injection and number of treatments.

| Therapy | Dose | 1$^{st}$ inj. | 2$^{nd}$ inj. | Termination | Evaluations | No. (RCS Rat) |
|---|---|---|---|---|---|---|
| STC-1 | STC-1$^{OptD}$ | P14 | none | P40 | qRT-PCR | 6 |
| | STC-1$^{OptD}$ | P14 | P21 | P40 | qRT-PCR | 6 |
| | STC-1$^{OptD}$ | P21 | P28 | P40 | qRT-PCR | 6 |
| | STC-1$^{OptD}$ | P28 | none | P40 | qRT-PCR | 6 |
| | STC-1$^{OptD}$ | P28 | P35 | P40 | qRT-PCR | 6 |
| PBS | 0 | fellow eye | | P40 | qRT-PCR | fellow eye |

Milestone: Optimal time of administration of STC-1 = STC-1$^{OptT}$.

1.2.2. Histological and functional therapeutic rescue by STC-1$^{OptD}$ and STC-1-$^{OptT}$. Histologic and functional tests are used to test the ability of STC-1$^{OptD}$ and STC-1$^{OptT}$ to rescue retinal degeneration compared to PBS injected controls. Fixed eyes are sent for quantification of ONL thickness as described in Lewin, et al., 1998. Electroretinogram (ERG) analysis is performed as described previously in Ren, et al., *Exp. Eye Res.*; Vol. 70, No. 4, pgs. 467-473 (2000).

TABLE 5

Histologic and functional tests of photoreceptor rescue.

| Therapy | Dose | Injection(s) | | Termination | Evaluations | No. (RCS Rat) |
|---|---|---|---|---|---|---|
| STC-1 | STC-1$^{OptD}$ | STC-1$^{OptT}$ | | P40 | Histology | 6 |
| STC-1 | STC-1$^{OptD}$ | STC-1$^{OptT}$ | | P40 | ERG | 6 |
| PBS | 0 | | | P40 | | fellow eye |

Milestone: Anatomic and functional measurements of the ability of STC-1 to rescue retinal degeneration.

Aim 2. Test the Hypothesis that Intravitreal Administration of MSCs Pre-Activated in Culture to Secrete Large Amounts STC-1 Will Provide Improvement of Photoreceptor Viability on the Basis that Sustained Secretion of STC-1 Will be More Effective than Protein Administration Alone.

2.1. Rationale. In order to determine whether cell therapy may provide greater rescue of photoreceptor viability than protein therapy alone, the hypothesis that intravitreally administered human MSCs can survive in the rat vitreous cavity was tested. Vials of frozen passage one human mesenchymal stem cells (hMSCs) were obtained from the Center for the Preparation and Distribution of Adult Stem Cells (http://medicine.tamhsc.edu/irm/msc-distribution.html). Following 24 hour recovery, the hMSCs were plated at a density of 100 cells/cm$^2$ and incubated at 37° C. in complete culture medium (CCM) with 16% fetal bovine serum (FBS) for 8 days until approximately 70% confluence was reached. Passage three cells were used for all experiments.

Figure 26:
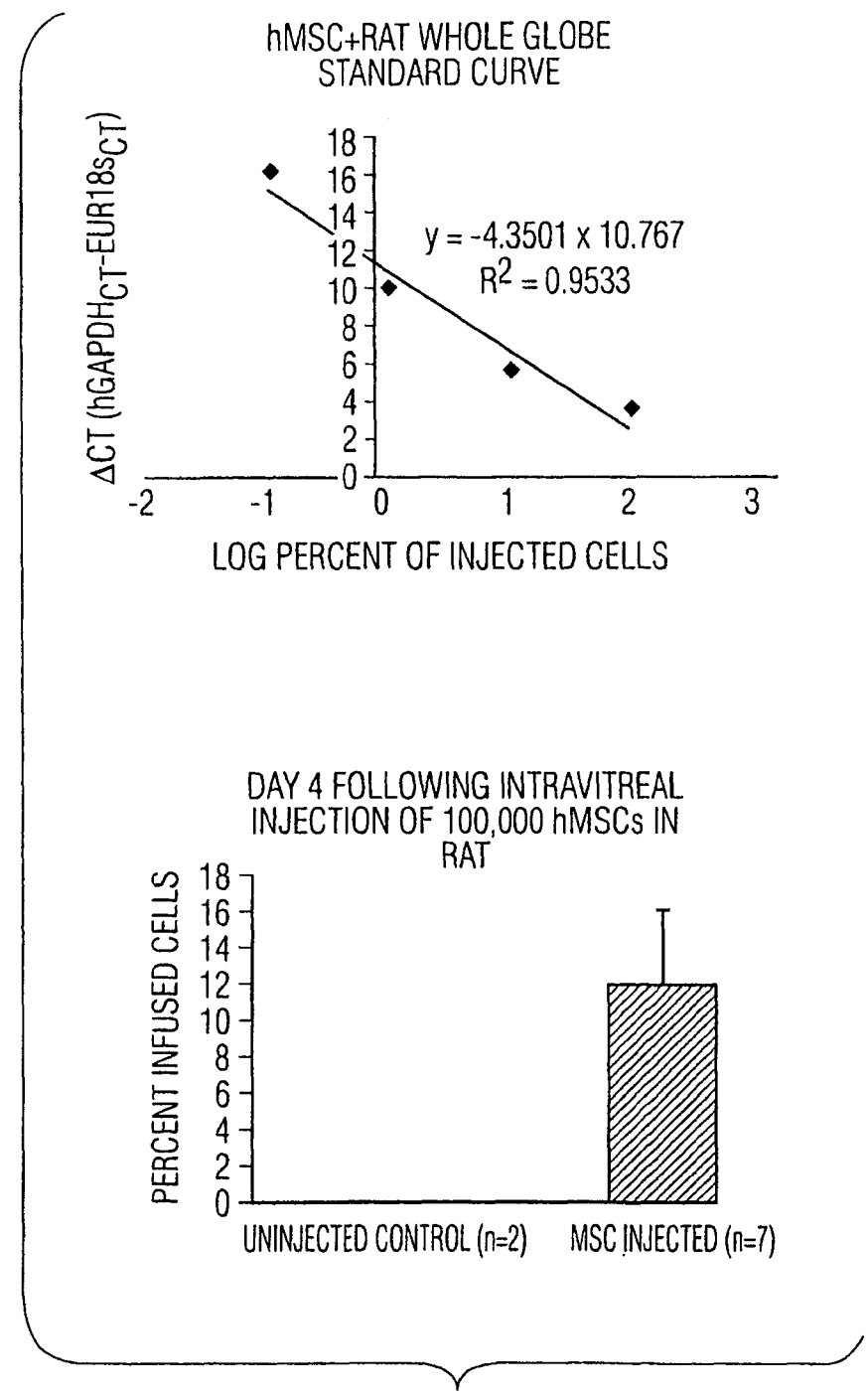
FIG. 26 MSCs survive in the vitreous cavity following injection. Left Panel: standard curve with human specific qRT-PCR for human GAPDH mRNA as a reflection of viable MSCs (see Lee, 2009 for Methods). Varying numbers of human MSCs added to whole globe just before RNA was extracted. Right Panel: Recovery of viable human cells 4 days after intravitreal injection of 100,000 human MSCs.

An intravitreal injection of 1×10$^5$ human MSCs was performed at post-natal day 21. Four days following injection the eye was enucleated and RNA was extracted from the whole globe to evaluate how many human cells remained in the eye cavity. Expression of human GAPDH (hGAPDH) was measured by qRT-PCR as hereinabove described, thereby providing an indication of any surviving human cells in the rat eye. Based on the standard curve generated (FIG. 26, Left Panel), an estimated 10-20% of injected cells remained viable for four days following injection (FIG. 26, Right Panel). This data provides the basis to test the hypothesis that sustained secretion of STC-1 by MSCs pre-activated in culture to secrete large amounts of STC-1 would have a greater therapeutic benefit than administration of protein alone. Additionally, other secreted factors from MSCs including the anti-inflammatory protein TSG-6 (Lee, 2009), neurotrophic factors (Li, et al., *Graefe's Arch. Clin. Exp. Ophthalmal.*, Vol. 247, No. 4, pgs. 503-514 (2009)) such as CNTF, bDNF, or bFGF, or the retinal-protective protein LIF (Bartosh, et al., *Proc. Nat. Acad. Sci.*, Vol. 107, No. 31, pgs. 13724-13729 (2010); Joly, et al; *J. Neurosci.*, Vol. 28, No. 51, pgs. 13765-13774 (2008)) may act in conjunction with STC-1 to preserve photoreceptor viability.

Figure 27:
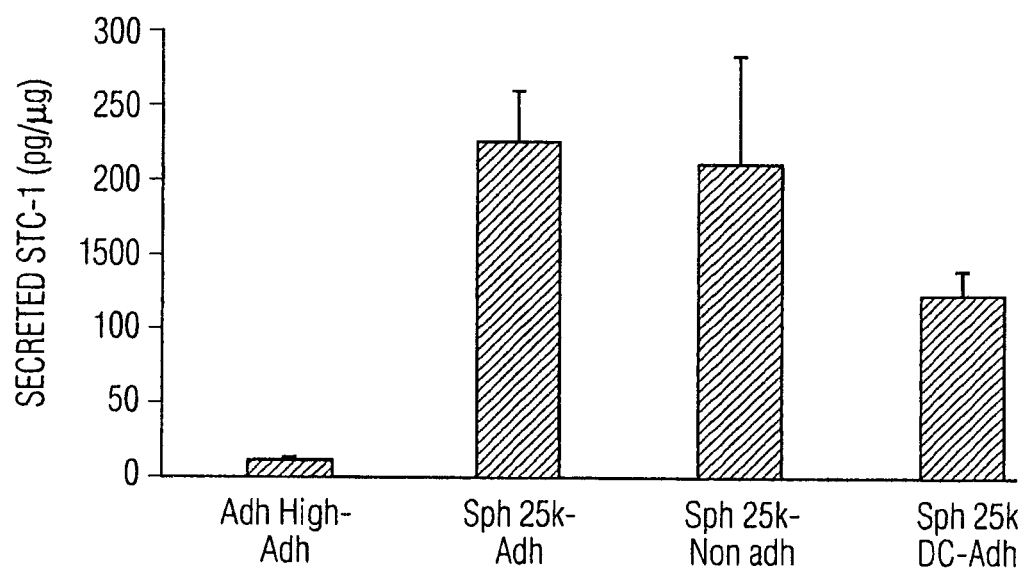
FIG. 27. Activation of expression of STC-1 by culture of human MSCs in hanging drops so that the cells coalesced into spheroids. High density monolayer (Adh High), spheroids (Sph 25k), and spheroid derived MSCs (Sph 25k DC) were transferred to 6 well plates containing 1.5 ml complete culture medium (CCM) and either 200,000 MCSs from high density cultures, eight 25k spheroids, or 200,000 MSCs. After 24 hours, medium was recovered for ELISAs and cells were lysed for protein assays. Figure adapted from (Bartosh, 2010). The results demonstrated an over 20-fold increase in secretion of STC-1 by spheroid MSCs (Sph 25k-Adh, Sph 25k-Non adh, or Sph 25k DC-Adh) compared to standard monolayer cultures of MSCs (Adh High-Adh).

MSCs in standard culture conditions express relatively low levels of therapeutic proteins unless stimulated in culture or activated in vivo by injury signals from the host (Lee, 2009; Bartosh, 2010). A recent report from our laboratory demonstrated that culturing MSCs as 3D spheroids activates the cells to produce large amounts of therapeutic molecules including STC-1 (Bartosh, 2010). Compared to standard culture preparations of MSCs, culture of the cells as 3D spheroids of 25,000 cells (Sph 25K) enhanced secretion of STC-1 about 20-fold. Spheroids can be dissociated into MSC spheroid dissociated cells (Sph 25k DC) which retain the ability to secrete high levels of STC-1 compared to monolayer MSCs (Adh High). (FIG. 27).

2.1.1. Optimization of the Dose of Sph 25k DCs. First, the dose of Sph 25k DCs which preserves photoreceptor viability (Sph 25k DC$^{OptD}$) most effectively is determined. The experiments are carried out as summarized in Table 6. For this experiment, Sph 25k based on photoreceptor gene expression (see FIG. 24) are injected.

TABLE 6

Dose of Sph 25k DCs. qRT-PCR analysis for. photoreceptor genes as described in FIG. 24.

| Therapy | Dose (×10³ cells) | Injection | Termination | Evaluations | No. (RCS Rat) |
|---|---|---|---|---|---|
| Sph 25k | 100 | P21 | P40 | qRT-PCR | 6 |
| DCs | 50 | P21 | P40 | qRT-PCR | 6 |
|  | 10 | P21 | P40 | qRT-PCR | 6 |
| MSCs | 100 | P21 | P40 | qRT-PCR | 6 |
|  | 50 | P21 | P40 | qRT-PCR | 6 |
|  | 10 | P21 | P40 | qRT-PCR | 6 |
| Fbs | 100 | P21 | P40 | qRT-PCR | 6 |
|  | 50 | P21 | P40 | qRT-PCR | 6 |
|  | 10 | P21 | P40 | qRT-PCR | 6 |
| PBS | 0 | P21 | P40 | qRT-PCR | fellow eye |

Milestone: Optimal dose of Sph 25k DCs = Sph 25k DC$^{OptD}$.

Potential pitfalls and alternative strategies. If MSCs provide greater rescue than Sph 25k DCs, then MSCs are used in subsequent experiments.

2.1.2. Optimization of the administration time and frequency of Sph 25k DCs. In parallel experiments, carried out as summarized in Table 7 below, the optimal time of administration is defined and whether two injections are more effective than one is determined.

TABLE 7

Time and frequency of administration of Sph 25k DCs.

| Therapy | Dose | 1$^{st}$ inj. | 2$^{nd}$ inj. | Termination | Evaluations | No. (RCS Rat) |
|---|---|---|---|---|---|---|
| Sph 25k | SPH 25k DC$^{OptD}$ | P14 | none | P40 | qRT-PCR | 6 |
| DCs | SPH 25k DC$^{OptD}$ | P14 | P21 | P40 | qRT-PCR | 6 |
|  | SPH 25k DC$^{OptD}$ | P21 | P28 | P40 | qRT-PCR | 6 |
|  | SPH 25k DC$^{OptD}$ | P28 | none | P40 | qRT-PCR | 6 |
|  | SPH 25k DC$^{OptD}$ | P28 | P35 | P40 | qRT-PCR | 6 |
| PBS | 0 | fellow eye |  | P40 | qRT-PCR | fellow eye |

Milestone: Optimal time of administration of Sph 25k DCs = Sph 25k DC$^{OptT}$.

2.1.3. Histological and functional therapeutic effects of Sph 25k DC$^{OptD}$ and Sph 25k DC$^{OptT}$. Histologic and functional tests carried out as described in Table 8 below, are used to test the ability of Sph 25k DC$^{OptD}$ and Sph 25k DC$^{OptT}$ to rescue retinal degeneration compared to PBS control.

TABLE 8

Histologic and functional tests of photoreceptor rescue.

| Therapy | Dose | Injection | Termination | Evaluations | No. (RCS Rat) |
|---|---|---|---|---|---|
| Sph 25k DCs | Sph 25k DC$^{OptD}$ | Sph 25k DC$^{OptT}$ | P40 | Histology | 6 |
|  | Sph 25k DC$^{OptD}$ | Sph 25k DC$^{OptT}$ | P40 | ERG | 6 |
| PBS | 0 |  | P40 | Histo/ERG | fellow eye |

Milestone: Anatomic and functional evidence of the rescue effects of Sph 25k DCs.

Aim 3. Test the Hypothesis that Our Preliminary Results Demonstrating Rescue of Photoreceptors in the RCS Rat are Explained by Previous Observations that STC-1 Inhibits Apoptosis and Reduces Reactive Oxygen Species by Uncoupling Oxidative Phosphorylation.

3.1 Rationale. It has been proposed that patients with RP undergo cone photoreceptor death due to oxidative damage following rod photoreceptor death (Shen, 2005; Usui, *Mol. Ther.*, Vol. 17, No. 5, pgs. 778-786 (2009)). Increased levels of oxygen have been observed in rodent models of RP including the RCS rat as photoreceptor degeneration occurs (Yu, 2004; Yu, et al., *Invest. Ophthalmol. Vis. Sci.*, Vol. 41, No. 12 pgs. 3999-4006 (2000)). As a result of increased levels of oxygen, oxidative damage to photoreceptors has been observed both in small (Komeima, 2006) and large (Shen, 2005) animal models of RP. Further evidence includes studies that demonstrate antioxidant therapy slows photoreceptor death in animal models of RP (Komeima, 2007). The hypothesis was tested initially in an in vitro model of oxidative RPE injury. Human RPE cells from cell line ARPE-19 (ATCC Catalog No. CRL-2302), were damaged with 450 μM hydrogen peroxide as described previously in Kim, et al., *Korean J. Ophthalmol.*, Vol. 17, No. 1, pgs. 19-28 (2003). As summarized in Table 9 below, one hour after injury, the cells were treated with 250 ng/ml STC-1, or with a vehicle (control).

TABLE 9

In vitro study using STC-1 treatment of hydrogen peroxide-damaged ARPE-19.

| Therapy | Dose | Assays |
|---|---|---|
| STC-1 | 250 ng/ml | TUNEL, mito. potential, lactate production, qRT-PCR |

TABLE 9-continued

In vitro study using STC-1 treatment of hydrogen peroxide-damaged ARPE-19.

| Therapy | Dose | Assays |
|---------|------|--------|
| Vehicle |      | TUNEL, mito. potential, lactate production, qRT-PCR |

The cells, following treatment, were evaluated for expression of a pro-apoptotic gene (caspase 3/7), cell death (Annexin V & PI staining of cells) and improved cell viability (increased activity of the mitochondrial enzyme MTT). Detection of caspase activity was performed as described in Sharma, et al., *Invest. Ophthalmol. Vis. Sci.*, Vol. 49, No. 11, pgs. 5111-5117 (2008), annexin/PI quantification as described in Bartosh, et al., *Proc. Nat. Acad. Sci.*, Vol. 107, No. 31, pgs. 13724-13729 (2010), and MTT conversion was measured as described previously in Mester, et al., *J. Mol. Neurosci.* (2010).

Figure 28:
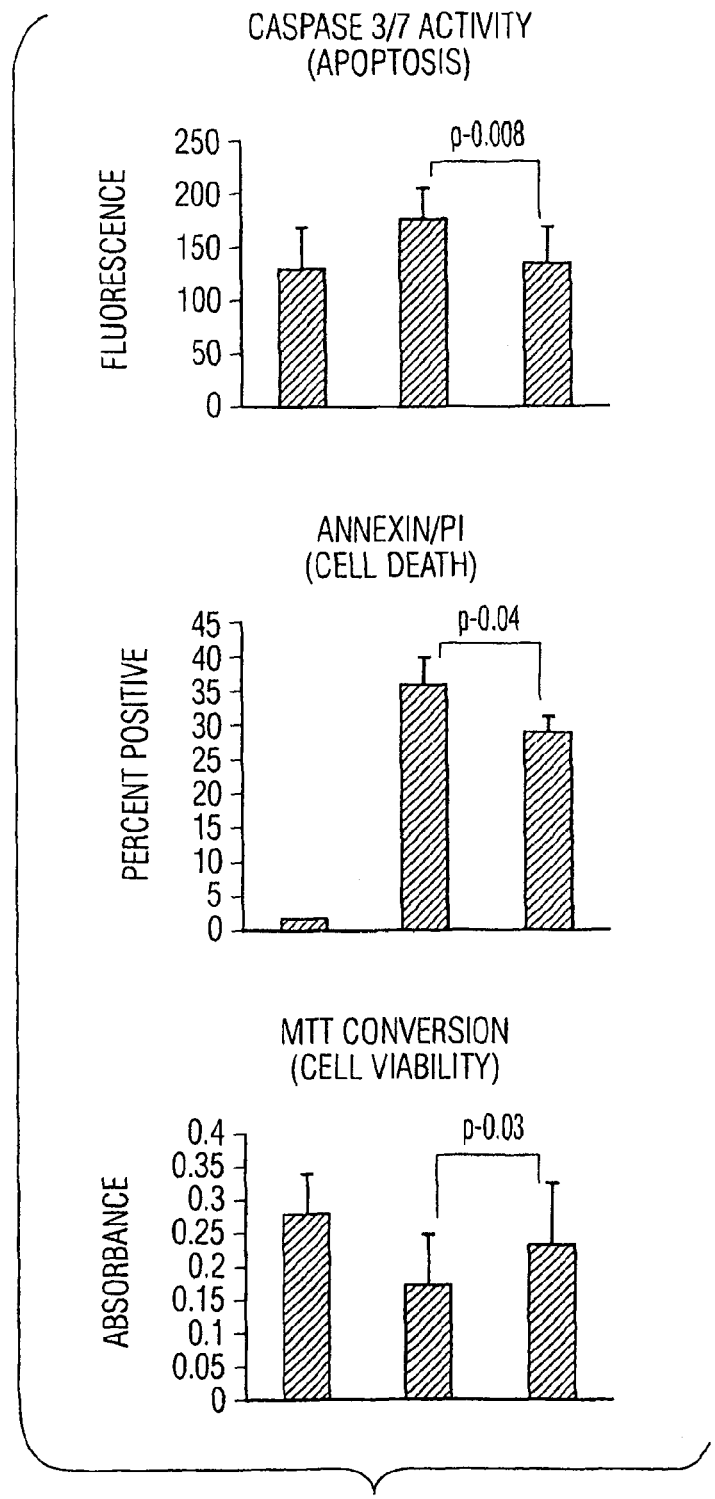
FIG. 28. Anti-apoptotic effects of STC-1 in cultures of RPE cells. Treatment with STC-1 (250 ng/mL) one hour following injury of ARPE-19 with 450 μM $H_2O_2$ reduced expression of a pro-apoptotic gene (caspase 3/7), cell death (Annexin V & PI staining cells) and improved cell viability (increased activity of the mitochondrial enzyme MTT). Detection of caspase activity was performed as described previously in Sharma, et al., *Invest. Ophthalmol. Vis. Sci.*, Vol. 49, No. 11, pgs, 5111-5117 (2008), annexin/PI quantification as described previously in Bartosh, 2010, and MTT conversion was measured as described previously in Mester, et al., *J. Mol. Neurosci.*, (2010).

Following injury, it was observed that treatment with STC-1 reduced apoptosis and improved cell viability compared to vehicle controls. (FIG. 28).

Figure 29:
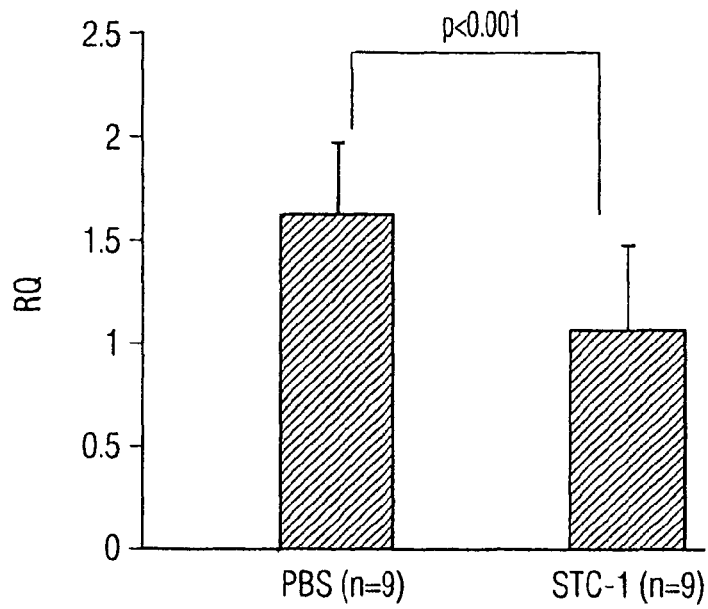
FIG. 29. Anti-apoptotic effect of STC-1 with intravitreal injection in RCS rats. Gene expression of BAX, a transcript that encodes a pro-apoptotic protein, was reduced significantly by STC-1 as quantified by qRT-PCR.

Additionally, the hypothesis was tested in the RCS rat. Following an intravitreal injection of 2.5 µg STC-1 in the RCS rat at P21, gene expression of BAX, a transcript that encodes a pro-apoptotic protein, is reduced significantly in the RCS retina at P40 (FIG. 29) as assessed by qRT-PCR. Therefore, these results are consistent with the idea that STC-1 inhibits the RCS Retina apoptosis. The hypothesis that the results are because of the ability of STC-1 to reduce reactive oxygen species by uncoupling oxidative phosphorylation then is tested.

3.2. Design. In vitro experiments are carried out as summarized in Table 9. In vivo experiments are carried out as summarized in Table 10. First, the in vitro model of hydrogen peroxide induced ARPE-19 injury (Kim, 2003) is used. Apoptosis in vitro is evaluated using TUNEL stain, lactate production (Tanito, *Invest. Ophthalmol. Vis. Sci.*, Vol. 46, No. 3, pgs. 979-987 (2005)), and qRT-PCR. The level of reactive oxygen species, or ROS, is evaluated using measurements of mitochondrial potential. Changes in UCP2 with qRT-PCR also is evaluated.

For in vivo studies, apoptosis in the retina of RCS rats is evaluated using TUNEL stain (Mizukoshi, *Exp. Eye Res.*, Vol. 91, No. 3, pgs. 353-361 (2010)) and qRT-PCR. In addition, levels of ROS are evaluated by measuring tissue aconitase activity as described previously in Tarpey, et al., *Am. J. Physiol. Regul. Integr. Comp. Physiol.*, Vol. 286, No. 3, pgs. 431-444 (2004).

TABLE 10

In vivo study using intravitreal administration of STC-1 in the RCS rat.

| Therapy | Dose | Injection(s) | Termination | Assays | No. (RCS Rats) |
|---------|------|--------------|-------------|--------|----------------|
| STC-1   | STC-1$^{OptD}$ | STC-1$^{Opt1}$ | P40 | TUNEL, aconitase, qRT-PCR | 6 |
| Vehicle |      |              | P40         | TUNEL, aconitase, qRT-PCR | 6 |

Example 9

Fifteen mice were anesthetized by isoflurane inhalation. In order to create a chemical burn to the cornea, 100% ethanol was applied to the whole cornea including the limbus for 30 seconds, followed by rinsing with 10 ml of balanced salt solution. The whole cornea and limbal epithelium then were scraped mechanically using a surgical blade. (See Oh, et al., *Proc. Nat. Acad. of Sci.*, Vol. 107, No. 39, pgs. 16875-16880 (Sep. 28, 2010)). Two mice served as controls. Immediately thereafter, 5 µl of PBS were administered intravenously or intraperitoneally to 10 mice, and 2 µg/5 µl of TSG-6 were applied topically to the corneal surfaces of 5 mice. The eyelids of the mice then were closed with one 8-0 silk suture at the lateral third of the lid margin.

Three days later, the mice were killed and the corneas were excised. The corneas then were sectioned into small pieces and lysed in 150 µl of tissue extraction reagent containing protease inhibitors (Invitrogen). The samples then were sonicated on ice and centrifuged twice (15,000×g at 4° C. for 20 minutes). The supernatants were assayed with commercial ELISA kits for myeloperoxidase (MPO) (MPO ELISA kit, Hy Cult Biotech).

Figure 30:
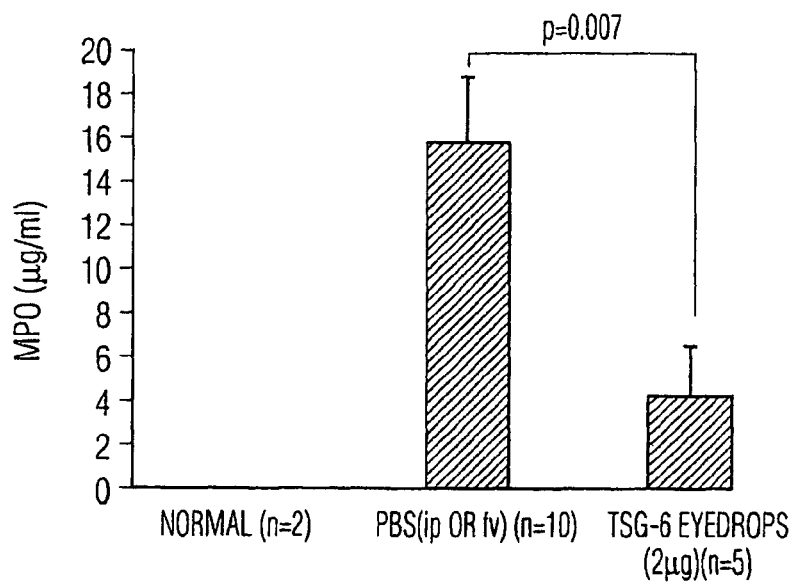
FIG. 30. Immediately after chemical and mechanical injury to mouse corneas, either PBS was administered to the mice intravenously or intraperitoneally, or TSG-6 (2 mg/5 ml) was applied to the surface of the mouse corneas. Lateral tarsorrhaphies then were performed on the eyes of the mice. Three days later, the corneas were extracted and myeloperoxidase (MPO) ELISA assays were performed.

As shown in FIG. 30, topical administration of TSG-6 suppressed corneal inflammation more effectively than the controls.

Example 10

Sterile inflammation now is recognized to play a key role in many diseases that include myocardial infarction, stroke, Alzheimer's disease, and atherosclerosis (Chen, et al., *Nat. Rev. Immunol.*, Vol. 10, No. 12, pgs. 826-837 (2010); Rock, et al., *Ann. Rev. Immunol.*, Vol. 28, pgs. 321-342 (2010); Spite, et al., *Circ. Res.*, Vol. 107, No. 10, pgs. 1170-1184 (2010)). The molecular and cellular responses of sterile inflammation include over 20 nonmicrobial endogenous stimuli referred to as damage-associated molecular patterns (DAMPs) which signal through pattern recognition receptors (PRRs) on resident macrophages that activate at least three intracellular pathways to upregulate the expression of pro-inflammatory cytokines. In spite of the intense interest in the field, a series of important questions remain unanswered, including whether some DAMPs identified from roles in vitro play important roles in vivo, whether some DAMPS play redundant roles, and whether different tissues used different DAMPs (Matzinger, *Nat. Immunol.*, Vol. 8, No. 1, pgs. 11-13 (2007)).

The cornea is an attractive model system to investigate sterile inflammation because it is accessible readily to experimental manipulations in vivo and in vitro. Moreover, sterile inflammation occurs in diseases of the cornea that include limbal stem cell deficiency, chemical burns, and allergic or autoimmune keratitis (Wagner, *Surv. Ophthalmol.*, Vol. 41, No. 4, pgs. 275-313 (1997); Krachmer, *Cornea*, 2$^{nd}$. Ed., Vol. 1, pgs 1179-1308). To examine the temporal sequence and stimuli for sterile inflammation, a model was used in which the cornea was injured by exposure to alcohol followed by scraping to remove the epithelium of the cornea and limbus that contains stem cells. It was observed that the injury provoked two distinct phases of neutrophil infiltration: A small initial Phase I that began in 15 mm and reached a plateau between 4 to 8 hours and a much larger second Phase II that peaked at 24 hours to 48 hours. Analysis of the two phases demonstrated that Phase I was stimulated by the neuropeptide secretoneurin and perhaps other signals. The second, more massive Phase II of neutrophil infiltration was simulated by a small heat shock protein, HSPB4, that was synthesized and released in injured keratocytes of the corneal stroma and that acted as a DAMP to activate resident macrophages.

Methods

Animals

Lewis rats (LEW/Crl) were purchased from Charles River Laboratory (Wilmington, Mass.). HSPB4 knockout mice (Cryaa$^{-1-}$) were generated originally at the National Eye Institute by targeted gene disruption and were maintained in the 129 S6/SvEvTac background (Brady, et al. *Proc. Nat. Acad. Sci.*, Vol. 94, No. 3, pgs. 884-889 (1997). 129S6/SvEvTac, C57BL/6 (C57BL/6J) and CD44 knockout mice (CD44h$^{-1-}$; B6.Cg-Cd44tm1Hbg/J) were purchased from the Jackson Laboratory (Bar Harbor, Me.). All animals were used under a protocol approved by the Institutional Animal Care and Use Committee of Texas A&M Health Science Center College of Medicine.

Animal Models of Injury and Treatment

Injury was created by applying 100% ethanol to the whole cornea including the limbus for 30 seconds followed by rinsing with 10 ml of balanced salt solution. Then, the whole corneal and limbal epithelium was scraped mechanically using a surgical blade.

For injection of the recombinant human SN (PolyPeptide Laboratories, Hillerød, Denmark) or HSPB4 (Enzo Life Sciences, Plymouth Meeting, Pa.), 2 µl of the proteins in PBS (0.2 ng SN in 2 µl PBS or 100 ng HSPB4 in 2 µl PBS; the amount of SN or HSPB4 detected in the cornea at 15 min after injury) were injected using a 32 gauge needle into the corneal stroma near the temporal limbus. The proteins were purified by endotoxin binding columns and sterilized prior to use according to the manufacturer's instructions (EndoClear, blue; Hycult Biotech Inc. Plymouth Meeting, Pa.), and tested to be free of detectable levels of Gram-negative bacterial endotoxins (<0.01 EU/ml) or proteins (1 ng/ml) using the Limulus amoebocyte lysate kit (Hycult Biotech Inc.) and *E. coli* HCP ELISA kit (Cygnus Technologies, Southport, N.C.).

For macrophage depletion, either 100 µl of clodronate-encapsulated liposome (5 mg clodronate per ml suspension; Encapsula Nano Sciences, Nashville, Tenn.) or the same volume of PBS-encapsulated liposomes were injected subconjunctivally near the limbus on day −2 (2 days before injury) and on day 0 (day of injury). The injection was dispensed over four quadrants (25 µl each) so that a circular bleb around the cornea was formed.

For blocking the release of SN from nerve endings, 20 µl of 2 mM diltiazem solution in isotonic saline (Sigma-Aldrich, St. Louis, Mo.) was applied topically to the cornea 15 min prior to injury (Gonzalez, et al., *Invest. Ophthalmol. Vis. Sci.*, Vol. 34, No. 12, pgs. 3329-3335 (1993). For blocking HSPB4 in the cornea, either mouse monoclonal or rabbit polyclonal antibodies to rat HSPB4 (10 µg or 50 µg in 100 µl PBS; Abcam, Cambridge, Mass.) were injected subconjunctivally near the limbus right before the injury. The same concentration of isotype IgG also was injected as control.

To evaluate the effect of TLR2 inhibition in the injured cornea, rhTSG-6 (2 µg in 5 µL of PBS; R&D Systems, Minneapolis, Minn.) or the same volume of PBS was injected into the anterior chamber of the rat eye immediately after injury.

Cells and Cell Lines

Murine macrophages (RAW 264.7) were obtained from ATCC (Rockville, Md.). Human embryonic kidney (HEK) 293 cells transfected with vectors expressing human TLR2 or TLR4 plus a vector expressing an alkaline phosphatase reporter gene under the control of an inducible NF-kB promoter were purchased from InvivoGen (HEK-Blue™-hTLR2 and HEK-Blue™-hTLR4; San Diego, Calif.). A control cell line not expressing either TLR2 or TLR4 also was obtained and used (HEK-Blue™-Null1). The stable cell line expressing human CD44 (Origene, Rockville, Md.) or PCDNA 3.1 control vector (Invitrogen) was generated. The primary human keratocytes were obtained from ScienCell (Carlsbad, Calif.), and used at passage 5.

Cell Injury Induction

To see the effects of injured cells in vitro, necrotic corneal tissue extracts were prepared. Rat corneas were homogenized in PBS (100 µl per one cornea) using a motor-driven homogenizer followed by five freeze-thaw cycles and 37° C. for 5 hours (Chen, et al., *Nat. Med.*, Vol. 13, No. 7, pgs. 851-856 (2007). After centrifugation at 12000 rpm for 5 min, the supernatants were prepared as necrotic extracts. Some of necrotic extracts were heat-treated (100° C., 20 min). Necrotic extracts were incubated with the cells in culture at a 1:10 dilution for 2 hours. To evaluate the effect of HSPB4, either antibodies to HSPB4 (10 µg or 50 µg) or isotype IgG antibodies also were added to the cultures.

To evaluate the effects of sHSPs and SN, either crystallins (HSPB4, HSPB5, βB crystallin; 0.001 to 10 µg/ml) or SN (0.1 to 10 ng/ml) were added to cultures and the cultures were incubated for 2 hours. To see the effect of TSG-6, 100 ng/ml or 500 ng/ml of rhTSG-6 were added to the cultures. To rule out the possibility of bacterial or LPS contamination of sHSPs, all in vitro experiments were done in the presence of polymyxin B (10 µg/ml) for neutralization of LPS. Moreover, for additional control experiments. sHSPs denatured by heat (100° C., 20 min) were used in parallel sets of experiments. To see whether keratocytes express sHSPs in response to injury, either necrotic extracts or $H_2O_2$ (100 to 500 nM) were added to the cultures of keratocytes.

Measurement of the Myeloperoxidase Amount in the Cornea

For a quantitative measure of neutrophil infiltration, the corneas were assayed for the myeloperoxidase (MPO) concentration (Rat MPO ELISA kit; HyCult biotech) as reported previously (Oh, et al., *Proc. Nat. Acad. Sci.*, Vol 101, No. 39, pgs. 16875-16880 (2010). For protein extraction, the cornea was cut into small pieces and lysed in 150 µl of tissue extraction reagent (Invitrogen, Carlsbad, Calif.) containing protease inhibitor cocktail (Roche, Indianapolis, Ind.). The samples were sonicated on ice using an ultrasound sonicator. After centrifugation at 12,000 rpm at 4° C. for 20 min, the cleared supernatant was collected and assayed for levels of MPO.

Microarrays

RNA target for microarrays was prepared using the 3' IVT Express Kit (Affymetrix) according to manufacturer's instructions. Briefly, 200 ng of total RNA was used to synthesize first strand cDNA. The cDNA then was converted into double-stranded cDNA and used in in vitro transcription to synthesize biotinylated cRNA. The cRNA was purified with magnetic beads, fragmented, and 12.5 µg were used in the hybridization onto RG-230 2.0 arrays. The arrays were stained, washed, and scanned for fluorescence. Microarray data was normalized and analyzed using the Partek Genomics Suite 6.4 (Partek) and dChip software. For comparative analysis, data were filtered based on fold changes of 2 or more (either up- or down-regulated). For the hierarchical clustering analysis data were filtered using a coefficient of variation higher than 0.6 and a presence call of at least 33%. The expression levels of the filtered genes were standardized and used in hierarchical clustering. A total 6 clusters were selected in each hierarchical clustering on the similar level of hierarchy and studied for enriched Gene Ontology tags based on hypergeometric distribution.

Real-time RT-PCR

Total RNA from the cornea or the cells was extracted (RNeasy Mini kit; Qiagen, Valencia, Calif.) and used to synthesize double-stranded cDNA by reverse transcription (SuperScript III; Invitrogen). Real-time amplification was performed (Taqman Universal PCR Master Mix Applied Biosystems, Carlsbad, Calif.) and analyzed on an automated instrument (7900HT Fast Real-Time PCR System; Applied Biosystems). PCR probe sets were purchased commercially (Taqman Gene Expression Assay Kits, Applied Biosystems). For assays, reactions were incubated at 50° C. for 2 min, 95° C. for 10 min, and then 40 cycles at 95° C. for 15 sec followed by 60° C. for 1 min. For normalization of gene expression, 18S rRNA probe (Taqman Gene Expression Assays ID, Hs03003631_g1) was used as internal control. The threshold cycle (Ct) was used to detect the increase in the signal associated with an exponential growth of PCR products during the log-linear phase. The expression of molecules was calculated using the algorithm $2^{-\Delta\Delta Ct}$.

Western Blot

Clear lysates prepared as described above were measured for protein concentration, and a total of 10 μg protein was fractionated by SDS-PAGE on 10% bis-tris gel (Invitrogen), transferred to nitrocellulose membrane (Invitrogen), and blotted with antibodies against SN (Phoenix Pharmaceuticals, Burlingame, Calif.) or HSPB4 (Abcam).

ELISAs

Protein was extracted from the cornea as described above, and was assayed for levels of pro-inflammatory cytokines and chemokines with commercial ELISA kits for IL-6, IL-1β, and CXCL1/CINC-1 (Quantikine kit; R&D Systems), and for CCL2/MCP-1 (Immunoassay Kit; Invitrogen). For HSPB4 measurement, mouse monoclonal anti-rat antibody to HSPB4 (Abeam) was used as a capture antibody (4 μg/ml) and rabbit polyclonal anti-rat antibody to HSPB4 (Abeam) as a secondary antibody (400 ng/ml).

Release of HSPB4 in Injured Cornea

To measure the amount of HSPB4 released from the cornea after injury, the corneas of rats were harvested immediately after the injury and cultured at 37° C. with 5% $CO_2$ for 12 hours. Every two hours, the culture medium was changed and the concentration of HSPB4 in conditioned medium during each time frame was measured by ELISA.

Histopathology

The cornea was excised after the rat was sacrificed and fixed in 10% paraformaldehyde. The cornea was cut into 4 μm sections and stained with the hematoxylin-eosin (H&E) or subjected to immunohistochemistry. The formalin-fixed corneal section was deparaffinized with ethanol and antigen was retrieved using an epitope retrieval solution (IHC WORLD, Woodstock, Md.). The rabbit polyclonal anti-rat antibody to neutrophil elastase (1:200, Abcam), the mouse monoclonal anti-rat antibody to secretogranin II (1:200, Abcam), or the mouse monoclonal anti-rat antibody to HSPB4 (1:200, Abcam) were used as primary antibodies, and the anti-rabbit IgG (1:5000, Abcam) or the anti-mouse IgG (1:5000, Abcam) as secondary antibodies. The DAPI solution (VECTASHIELD Mounting Medium; Burlingame, Calif.) was used as counterstaining.

Aconitase Activity Assay

To evaluate the oxidative damage in the cornea by injury (Ma, et al., *Biochem, Biophys. Acta*, Vol. 1790, No. 10. pgs. 1021-1029 (2009), loss of aconitase activity in the corneal lysates was measured using an aconitase assay kit according to the manufacturer's protocol (Cayman Chemical Company, Ann Arbor, Mich.)

NF-kB Translocation Assays

About $1\times10^5$ mouse macrophages were plated in 8 well chamber slides (Lab-Tek II Chamber Slide; Nalge Nunc, Rochester, N.Y.) and incubated for 1 hour in 0.2 mL of 2% FBS in α-MEM with or without 10 μg/mL HSPB4. The cells were washed twice with PBS by centrifugation and were fixed with 100% methanol for 5 min. The cells were washed with PBS and blocked with Image-iT™ FX Signal Enhancer (Invitrogen) The cells then were incubated with 1 μg/mL of anti NF-kB p65 antibody (Abcam) in blocking buffer (5% BSA in PBS) overnight at 4° C. The samples were incubated for 1 hour with a 1:2000 dilution of the secondary antibody of anti-rabbit IgG (Alexa Fluor® 488 goat; Invitrogen). The DAPI solution was used to stain the cell nuclei. The slides were visualized with fluorescent microscopy using an upright microscope (Eclipse 80i, Nikon, Melville, N.Y.)

Statistical Analysis

Comparisons of parameters among the groups were made by the Student's t test, non-parametric Mann-Whitney test or Pearson's correlation test using SPSS software (SPSS 12.0). Differences were considered significant at $p<0.05$.

Results

Two Phases of Neutrophil Infiltration after Sterile Injury to the Cornea

Figure 31A:
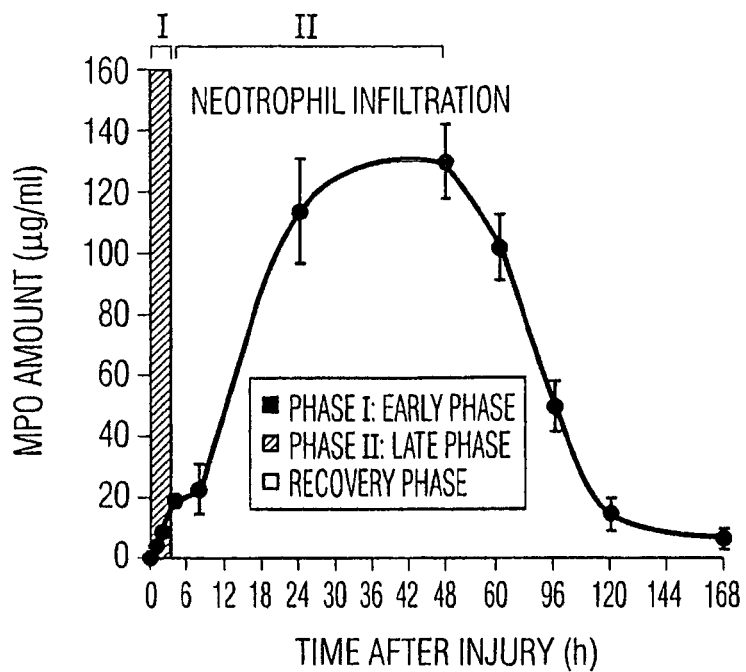
FIG. 31. Early events in the cornea after injury. A. The neutrophil infiltration occurred in the two phases: 1) a small initial phase that began within about 15 min, and reached a plateau level at 4 h (Phase I) and 2) a much larger infiltration of neutrophils with a peak at 24 to 48 h (Phase II). B. Based on the temporal pattern of expression in microarrays, the up-regulated genes in the injured cornea were divided into three groups. C. Real time PCR analysis of representative genes in each group. The group A genes preceded Group B and C genes in mRNA expression. D. Microarray heat map of genes from the corneas 4 h and 24 h after injury. Gene ontology categories and the number of genes up-regulated (red) or down-regulated (blue)>2-fold are indicated. Based on the expression pattern, genes were categorized into three groups: genes whose expression increased rapidly early after injury and thereafter decreased (Group A), genes that were expressed at steady levels (Group B), and genes increased gradually after injury (Group C).

The corneas of Lewis rats, were injured by exposing them to 100% ethanol for 30 seconds and scraping of the cornea and limbus to remove both the epithehum and stem cells found in the limbus. As described previously (Oh, et. al, *Proc. Nat. Acad. Sci.*, Vol. 107, No. 34, pgs. 16875-16880 (2010), neutrophil infiltration was monitored by assays for myeloperoxidase (MPO) that is stored within neutrophil granules and released by activation of the cells (Borregard, et al., *Blood*, Vol. 89, pgs. 3503-3521 (1997). The neutrophil infiltration occurred in the two phases. There was a small initial phase that began within about 15 min, and reached a plateau level at 4 to 8 hours (Phase I in FIG. 31A). After the plateau, a much larger infiltration of neutrophils followed and reached a maximum at 24 to 48 hours (Phase II in FIG. 31A). The neutrophils then gradually disappeared in a recovery phase over 48 hours to 7 days.

Search for Candidate Signals for Phase I and Phase II

Figure 31B:
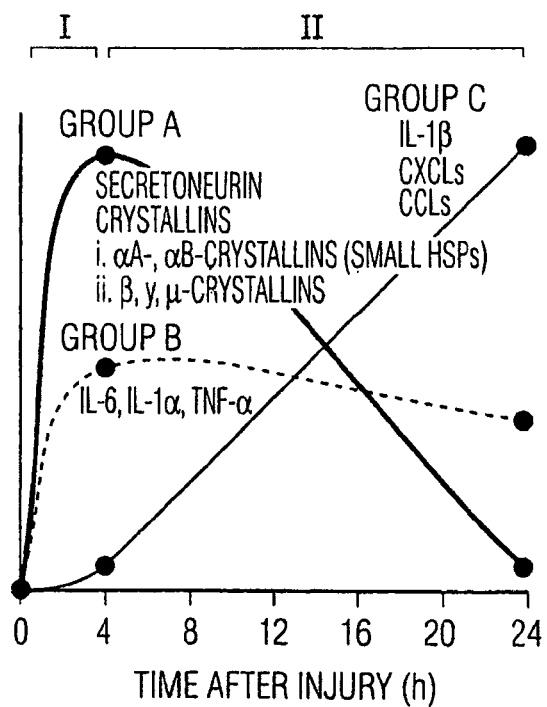
Figure 31C:
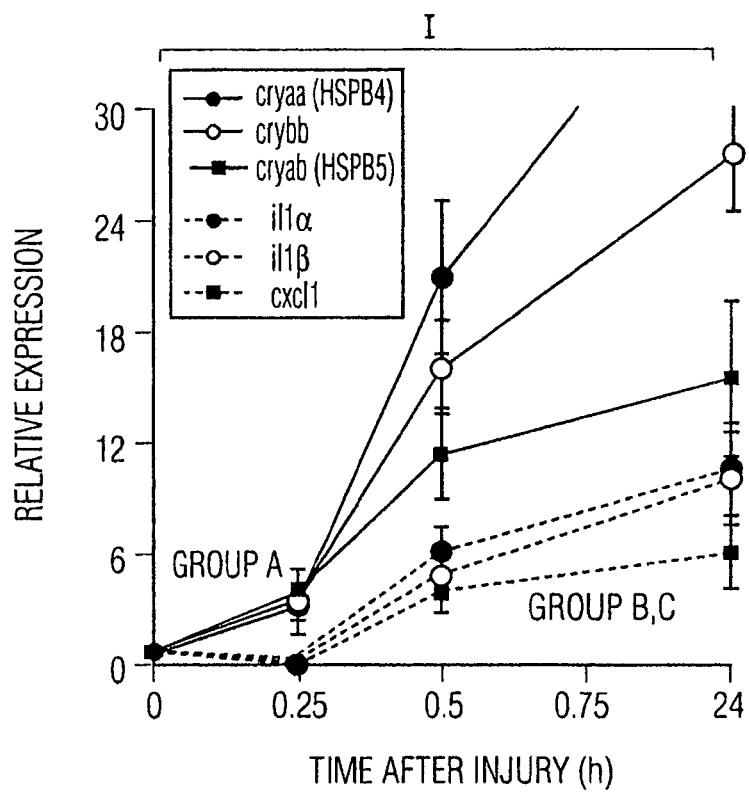

As a strategy to identify candidate signals that initiated the two phases, microarrays were used to survey the response of the cornea to injury. Based on the temporal pattern of gene expression, the genes were classified into three groups (FIG. 31B, FIG. 31D). About 842 Group A genes were up-regulated, about 108 Group B genes were up-regulated, and about 307 Group C genes were up-regulated (FIG. 31D). Focus was directed to the Group A genes, because they were expressed earlier and therefore more likely to include stimuli for Phase I and II (FIGS. 31 B and C). Most of the Group B genes were the molecules related to apoptosis/death and defense response (See Table 11 below, FIG. 31D). Most of the Group C molecules were pro-inflammatory chemokines and cytokines (See Table 11 below, FIG. 31D, FIG. 32M), and therefore were likely to be the genes that peaked late in the inflammatory responses. Most of the Group A genes were genes for nerve/neurotransmission-related and structural proteins of the eye (See Table 11 below.) From the category of Group A genes, the following were selected as attractive candidates for inflammatory signals: The neuropeptide secretoneurin (SN) because it was shown previously to activate chemotaxic migration and transendothelial extravasation of blood cells (Helle, *Regul Pept.*, Vol. 165, No. 1, pgs. 45-51 (2010); Taupenot, et al., *N. Engl. J. Med.*, Vol. 348, No. 12, pgs. 1134-1149 (2003), and two small heat shock proteins (HSPB4 and HSPB5) because some heat shock proteins were previously shown to act as DAMPs (Joly, et al., *J. Innate Immun.*, Vol. 2, No. 3, pgs. 238-247 (2010); Van Wijk, et al., *J. Leukoc. Biol.*, Vol. 88, No. 3, pgs. 431-434 (2010); Quintana, et al., *J. Immunol.*, Vol. 175, No. 5, pgs. 2777-2782 (2005); Asea, et al., *Nat. Med.*, Vol. 6, No. 4, pgs. 435-442 (2000).

TABLE 11

Microarray analysis of gene expression profiles in the cornea at 4 hours and 24 hours after injury. The top 20 transcripts upregulated by injury were shown in each group (Group A, B, and C).

| Gene Title | Gene symbol | Probe set | Change (x-Fold) Injured (4 h)/con | Change (x-Fold) Injured (24 h)/con |
|---|---|---|---|---|
| Group A | | | | |
| crystallin, alpha A | Cryaa | 1370279_at | 19.468 | 1.620 |
| crystallin, beta B1 | Crybb1 | 1369985_at | 18.541 | 1.062 |
| crystallin, gamma C | Crygc | 1370292_a_at | 17.911 | 1.112 |
| secretogranin II | ScgII | 1368044_at | 15.847 | 1.033 |
| claudin 2 | Cldn2 | 1375933_at | 15.246 | 1.033 |
| crystallin, beta A1 | Cryba1 | 1371408_at | 14.628 | −3.593 |
| crystallin, gamma B | Crygb | 1371413_x_at | 14.311 | 1.025 |
| crystallin, gamma D | Crygd | 136770._at | 13.957 | 1.054 |
| synaptosomal-associated protein 25 | Snap25 | 1387073_t | 13.199 | 1.580 |
| Galectin-related inter-fiber protein | Grifin | 1386936_at | 12.710 | −1.129 |
| solute carrier family 6 (neurotransmitter transporter, GABA), member 1 | Slc6a1 | 1368170_at | 12.359 | −1.704 |
| crystallin, gamma S | Crygs | 1388435_at | 11.969 | −1.096 |
| Calbindin | Calb1 | 1370201_at | 11.542 | −1.184 |
| crystallin, beta A2 | Cryba2 | 1388385_at | 10.349 | −1.497 |
| crystallin, beta B2 | Crybb2 | 1367684_at | 9.918 | −1.738 |
| retinol binding protein 3, interstitial | Rbp3 | 1376777_at | 9.789 | −1.434 |
| collagen, type II, alpha 1 | Col2a1 | 1387767_a_at | 8.615 | −1.224 |
| phosphodiesterase 6A, cGMP-specific, rod, alpha | Pde6a | 1393426_at | 8.500 | −1.011 |
| complexin 3 | Cplx3 | 1384779_at | 8.061 | −1.099 |
| crystallin, alpha B | Cryab | 1370026_at | 7.197 | 1.812 |
| crystallin, beta A4 | Cryba4 | 1367608_at | 7.168 | −1.749 |
| Group B | | | | |
| interleukin 6 | Il6 | 1369191_at | 340.974 | 293.81 |
| colony stimulating factor 3 (granulocyte) | Csf3 | 1369529_at | 70.050 | 62.614 |
| matrix metallopeptidase 13 | Mmp13 | 1388204_at | 30.118 | 28.285 |
| prostaglandin E synthase | Ptges | 1368014_at | 19.449 | 15.069 |
| metallothionein 2A | Mt2A | 1388271_at | 17.356 | 13.067 |
| superoxide dismutase 2, mitochondrial | Sod2 | 1370173_at | 16.915 | 11.803 |
| interleukin I alpha | Il1a | 1371170_a_at | 14.637 | 5.275 |
| prostaglandin-endoperoxide synthase 2 | Ptgs2 | 1368527_at | 10.861 | 8.108 |
| metallothionein 1a | Mt1a | 1371237_a_at | 9.483 | 6.815 |
| lipocalin2 | Lcn2 | 1387011_at | 9.013 | 9.387 |
| immediate early response 3 | Ier3 | 1388587_at | 5.552 | 5.781 |
| prostaglandin E synthase | Ptges | 1368015_at | 5.433 | 5.051 |
| six transmembrane epithelial antigen of the prostate 1 | Steap1 | 1393706_at | 5.221 | 4.467 |
| cAMP responsive element modulator | Crem | 1393550_at | 5.213 | 4.998 |
| transferrin receptor | Tfrc | 1388750_at | 5.182 | 5.061 |
| mitogen-activated protein kinase 8 | Map3k8 | 1369393_at | 4.935 | 5.302 |
| B-cell translocation gene 2, anti-proliferative | Btg2 | 1386994_at | 4.931 | 4.677 |
| runt related transcription factor 1 | Runx 1 | 1368914_at | 4.924 | 3.913 |
| similar to F-box only protein 27 | RGD1563982 | 1375041_at | 4.717 | 3.358 |
| growth arrest, DNA-damage-inducible, alpha | Gadd45a | 1368947_at | 4.026 | 3.756 |

TABLE 11-continued

Microarray analysis of gene expression profiles in the cornea at 4 hours and 24 hours after injury. The top 20 transcripts upregulated by injury were shown in each group (Group A, B, and C).

| Gene Title | Gene symbol | Probe set | Change (x-Fold) Injured (4 h)/ con | Injured (24 h)/ con |
|---|---|---|---|---|
| Group C | | | | |
| secretory leukocyte peptide | Slpi | 1367998_at | 54.415 | 533.847 |
| chemokine (C—X—C motif) ligand 2 | Cxcl2 | 1368760_at | 52.728 | 404.344 |
| S100 calcium binding protein A9 | S100a9 | 1387125_at | 56.114 | 207.701 |
| interleukin 1 beta | Il1b | 1398256_at | 33.522 | 198.673 |
| chemokine (C-C motif) ligand 7 | Ccl7 | 1379935_at | 40.595 | 159.69 |
| S100 calcium binding protein A8 | S100a8 | 1368494_at | 33.206 | 155.69 |
| chemokine (C—X—C motif) ligand 3 | Cxcl3 | 1370633_at | 7.895 | 128.417 |
| chemokine (C-C motif) ligand 3 | Ccl3 | 1369815_at | 6.493 | 95.538 |
| interleukin 1 receptor, type II | Il1r2 | 1387180_at | 24.159 | 60.257 |
| chemokine (C—X—C motif) ligand 3 | Cxcl3 | 1370634_x_at | 4.934 | 59.166 |
| interleukin I alpha | Il1a | 1368592_at | 2.953 | 54.174 |
| Fc fragment of IgG, low affinity IIa, receptor | Fcgr2a | 1367850_at | 8.708 | 41.195 |
| Cd53 molecule | Cd53 | 1368518_at | 6.748 | 31.988 |
| chemokine (C-C motif) receptor 1 | Ccr1 | 1370083_at | 6.359 | 28.512 |
| chemokine (C—X—C motif) ligand 3 | Cxcl3 | 1388032_a_at | 2.331 | 24.419 |
| colony stimulating factor 3 receptor | Cst3r | 1386009_at | 8.094 | 21.987 |
| Fc fragment of IgG, high affinity Ia, receptor | FcgrIa | 1393038_at | 3.611 | 21.032 |
| laminin, gamma 2 | Lamc2 | 1379340_at | 5.817 | 20.577 |
| immunoglobulin superfamily, member 6 | Igsf6 | 1387687_at | 2.915 | 20.148 |
| complement component 3 | C3 | 1368000_at | 6.292 | 15.602 |

Symbols:
Injured (4 h)/con, cornea at 4 hours after injury vs. cornea right after injury;
Injured (24 h)/con, cornea at 24 hours after injury vs. cornea right after injury;
'−' means downregulation. The values are the results from collective samples of n = 4 per each group.

SN as a Candidate for Phase I and HSPB4 for Phase II

Figure 32A:
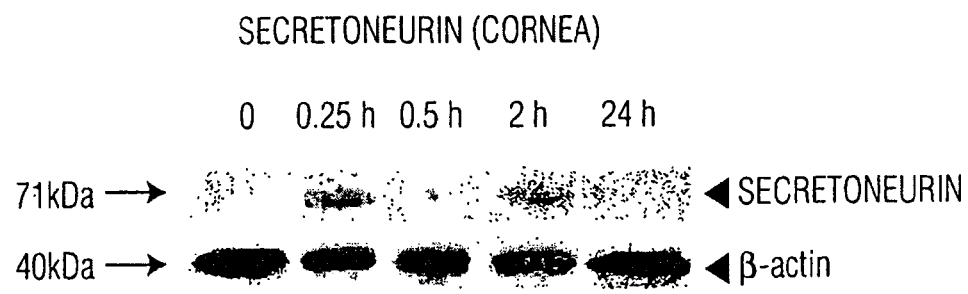
FIG. 32. Expression patterns of secretoneurin (SN) and HSPB4 in the injured cornea. A, E. Western blot of SN and HSPB4 in the cornea. SN was released into the cornea immediately after injury, and HSPB4 reached a peak at 4 h. B, F. G. ELISA of SN and HSPB4 in the serum and cornea. SN was released into the cornea and the serum within 0.25 h of the injury. HSPB4 was released into the extracellular space as measured in the supernatants of the ex vivo culture of corneas after 2 to 4 h. C, H. Immunohitochemistry of SN and HSPB4 in the cornea. D, I. Real time PCR of neuropeptides and crystallins. Among neuropeptides and crystallins analyzed, SN and HSPB4 showed the highest expression in the injured cornea. J. In response to necrotic extracts, keratocytes in culture expressed HSPB4. K. As measured by aconitase activity, oxidative stress was generated in the cornea by injury. L. The hydrogen peroxide increased the expression of HSPB4 in keratocytes. M. Temporal expression of IL-6, IL1β, CXCL1, and CCL2 in the cornea. ELISAs demonstrated that the expression of proteins of Group B (IL-6) and Group C (IL-1β, CXCL1, and CCL2) genes paralleled gene expression as assayed for mRNAs with microarrays and real time RT-PCR assays.
Figure 32B:
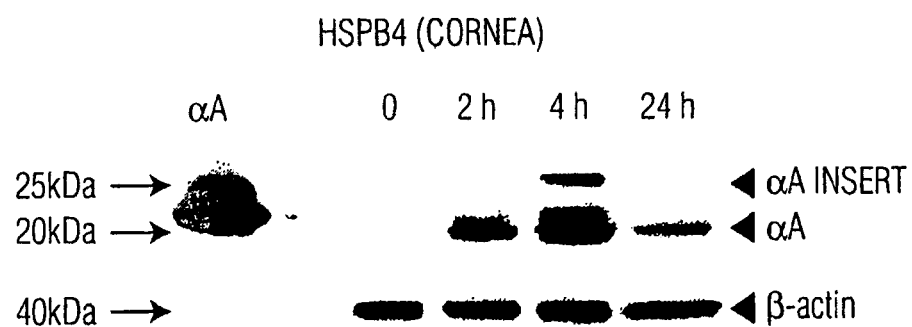

Data on the time course of expression were consistent with SN serving as an initiating signal for Phase I. SN was not detected in extracts of uninjured cornea, but appeared both in corneal extracts and the serum of the rats within 0.25 hour of the injury (FIGS. 32A and B). The levels of SN in extracts of injured corneas and the serum decreased at 0.5 hour and then increased apparently as a result of increased expression of the gene (FIGS. 32A-D). In contrast, there were little changes in the expression of genes for substance P and calcitonin gene-related peptide (CGRP), two other neuropeptides known to be expressed in the cornea (FIG. 32D) (Troger, et al., *Brain Res. Rev.*, Vol. 53, No. 1, pgs. 39-62 (2007).

Figure 32C:
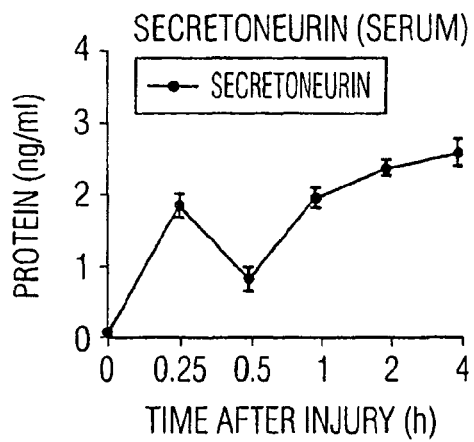
Figure 32D:
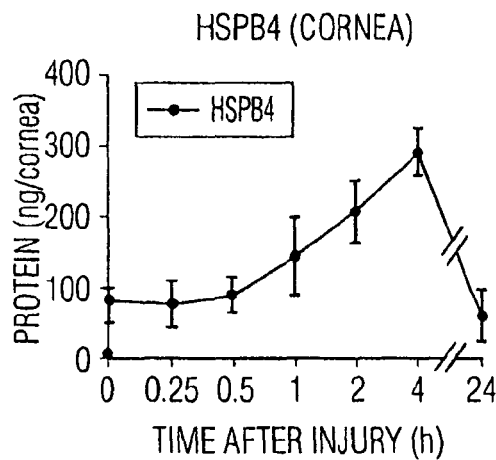
Figure 32E:
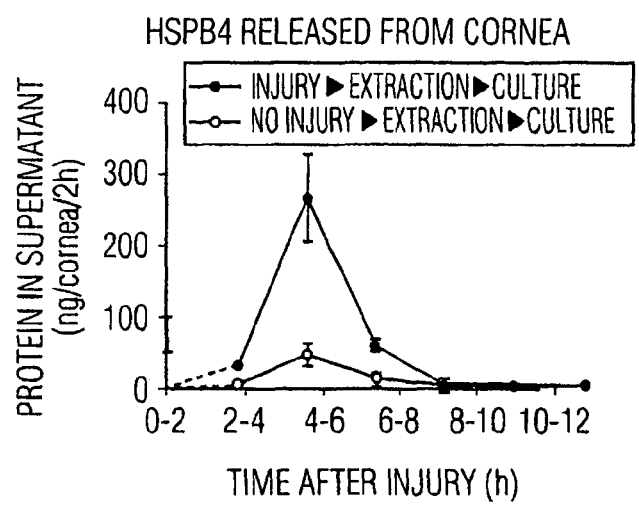
Figure 32F:
Figure 32G:
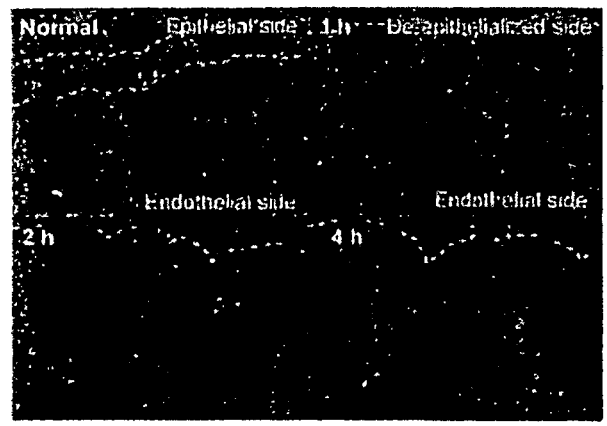
Figure 32H:
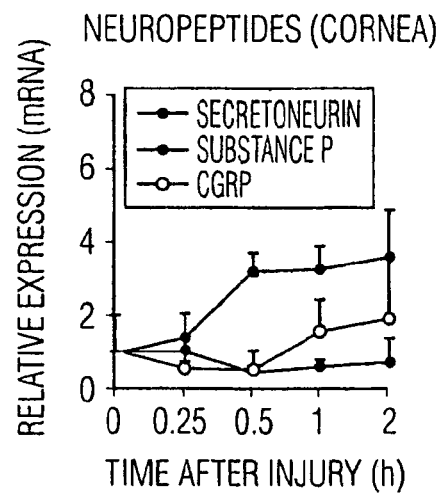
Figure 32I:
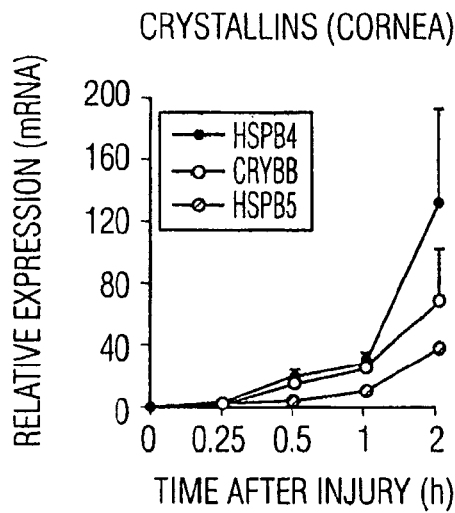

Similar data on the time course of expression were consistent with HSPB4 serving as a stimulus for Phase II. Uninjured cornea contained low levels of HSPB4 protein but the amount increased beginning after 0.5 hour of the injury and reached a peak at about 4 hours (FIGS. 32E and F). A similar time course was observed in the release of HSPB4 into the medium in experiments in which corneas were injured in vivo and then incubated ex vivo (FIG. 32G). As expected from the microarray data, there was increased expression of mRNAs for HSPB4 and related genes from Group A (FIG. 32I); however, the increases in expression of HSPB4 were delayed compared to the increase in the mRNA for SN (compare FIGS. 32D and I). Immunohistochemistry of injured cornea was consistent with the results. The SN-immunoreactive nerves were increased in the cornea at 2 hours following injury (FIG. 32C). The expression of HSPB4 was increased at about 4 hours following injury (FIG. 32H).

In addition, the expressions of SN and HSPB4 were dependent on the severity of injury. The concentrations of both the proteins and mRNAs were higher in the cornea or serum following severe injury (30 sec ethanol and scraping) compared to mild injury (15 sec ethanol and scraping) (FIG. 33F).

Keratocytes from the Corneal Stroma Synthesized HSBP4 in Response to Injury

Figure 32J:
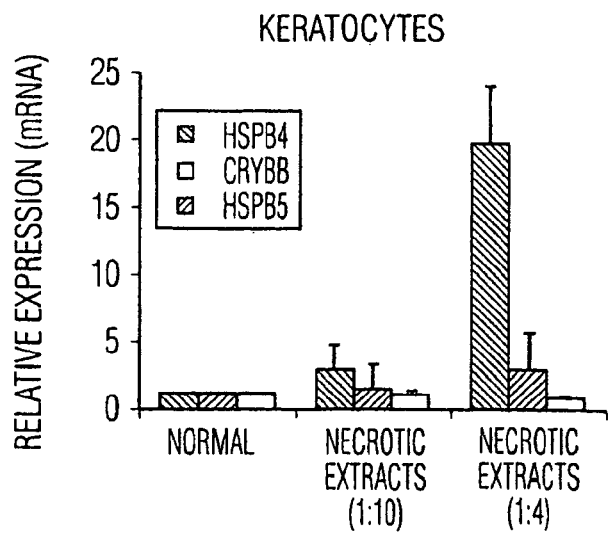

To define the cellular origin of HSPB4 in the injured cornea, keratocytes that are fibroblast-like cells from the corneal stroma were incubated with extracts of the cornea that were made necrotic by repeated freezing and thawing. The necrotic extracts induced the expression of HSPB4 in the keratocytes (FIG. 32J). The necrotic extracts did not increase significantly the expression of a second small heat shock protein HSPB5 or a third Group A gene, βB crystallin. Most sterile inflammations produce increases in reactive-oxygen species (ROS)

Figure 32K:
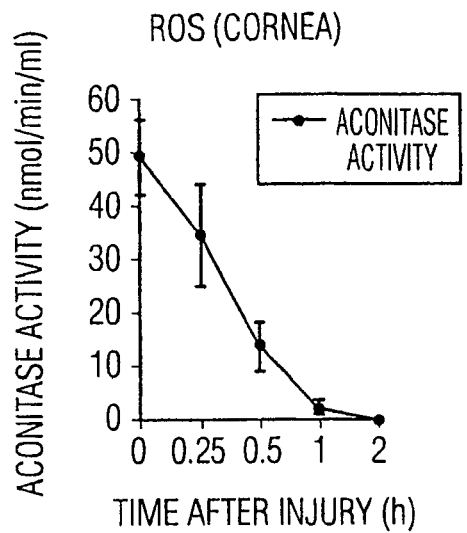
Figure 32L:
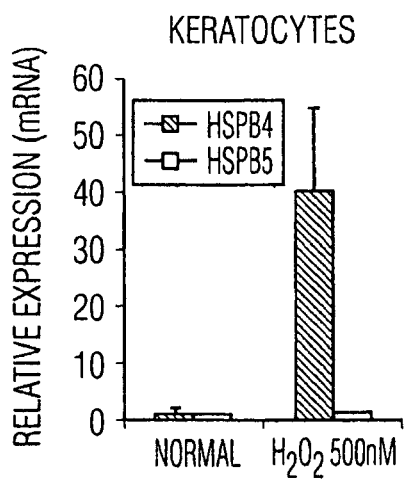
Figure 32M:
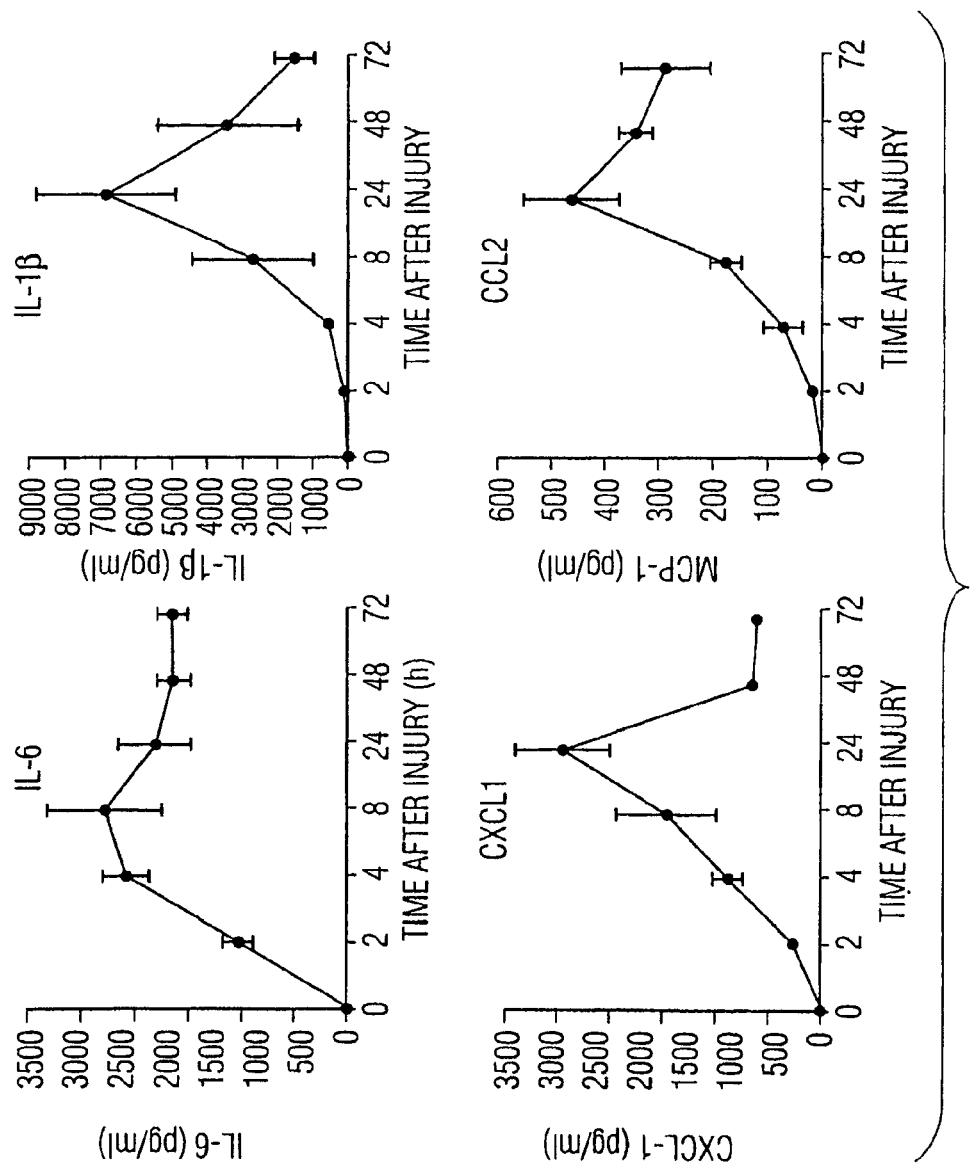

(Kolnitzer, et al., *Ann. N.Y. Acad. Sci.*, Vol. 1203, pgs 45-52 (2010); Martinon, *Eur. J. Immunol.*, Vol. 40, No. 3, pgs. 616-619 (2010). Assays of injured cornea demonstrated a rapid decrease in aconitase activity, a reflection of an increase in ROS (FIG. 32K). As expected, incubation of keratocytes with $H_2O_2$ to increase ROS also produced increased expression of HSPB4 (FIG. 32L).

Recombinant SN Reproduced Phase I and Recombinant HSPB4 Reproduced Phase II

Figure 33A:
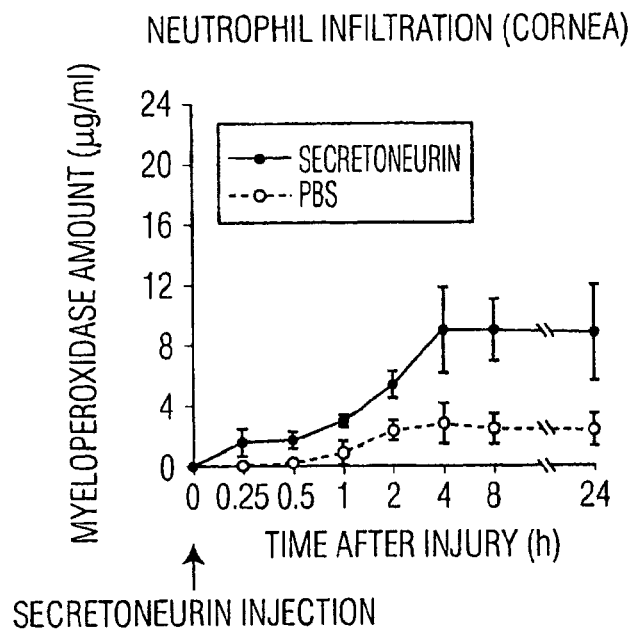
FIG. 33. SN reproduced the Phase I inflammatory response, and HSPB4 reproduced both the Phase I and Phase II. A. The injection of the recombinant SN induced the early infiltration of neutophils of Phase I, but of Phase II. B, C. HSPB4 injection induced the Phase I and Phase II responses accompanied by corneal opacity and neutrophil infiltration as shown in hematoxylin-eosin staining and immunostaining for neutrophil elastase of the region of the cornea into which HSPB4 was injected. D. The topical application of the calcium channel blocker Diltiazem inhibited significantly the Phase I response in corneal injury to chemical injury. E. The subconjunctival injection of polyclonal (pAb) or monoclonal (mAb) antibodies to HSPB4 decreased significantly the neutrophil infiltration in Phase II, compared to isotype control (IgG)-injected group. F. The amounts of SN and HSPB4 released into the cornea were dependent on the severity of injury as measured by real time PCR of SN and HSPB4 in the injured cornea and ELISA for SN and HSPB4 in the serum or cornea. The concentrations of mRNAs and proteins were higher in the cornea or serum by severe injury (30 sec ethanol and scraping), compared to mild injury (15 sec ethanol and scraping). G. After subconjunctival injections of clodronate-encapsulated liposome ($Cl_2$ MDP-LIP) on day −2 (i.e., 2 days before injury) and day 0 (immediately after injury), sections of the rat cornea were stained with hematoxylin-eosin (H&E), or antibodies to CD11b and CD68 to identify macrophages. The structure of the cornea on H&E was not affected by $Cl_2$ MDP-LIP. CD11b- and CD68-positive cells in the cornea, however, were decreased significantly by $Cl_2$MDP-LIP compared to PBS-encapsulated liposome-injected controls (PBS-LIP).

Injection of recombinant SN into the stroma of the cornea stimulated the neutrophil infiltration of Phase C (FIG. 33A). The effect was negated partially by topical application of a calcium blocker (Diltiazem) (FIG. 33D) that inhibits release of neuropeptides (Gonzalez, et al, *Invest. Ophthalmol. Vis. Sci.*, Vol. 34, No. 12, pgs. 3329-3335 (1993). The results therefore indicated that SN served as a major stimulus for Phase I, but they did not exclude the possibility that it acted in concert with other signals released by the injured cornea.

Figure 33B:
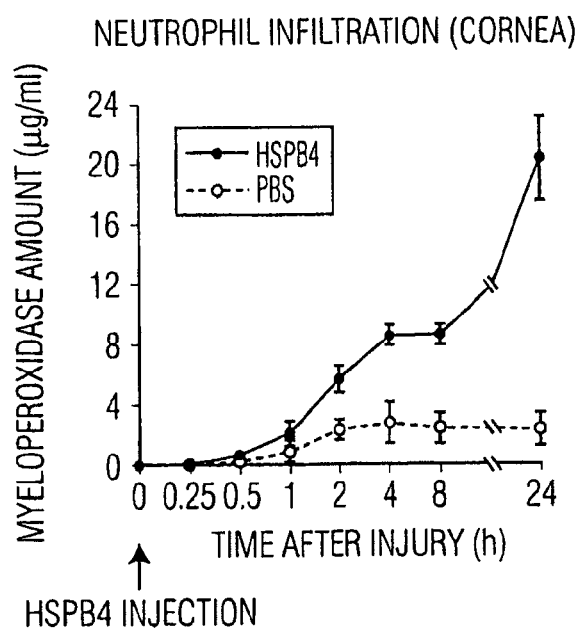
Figure 33C:
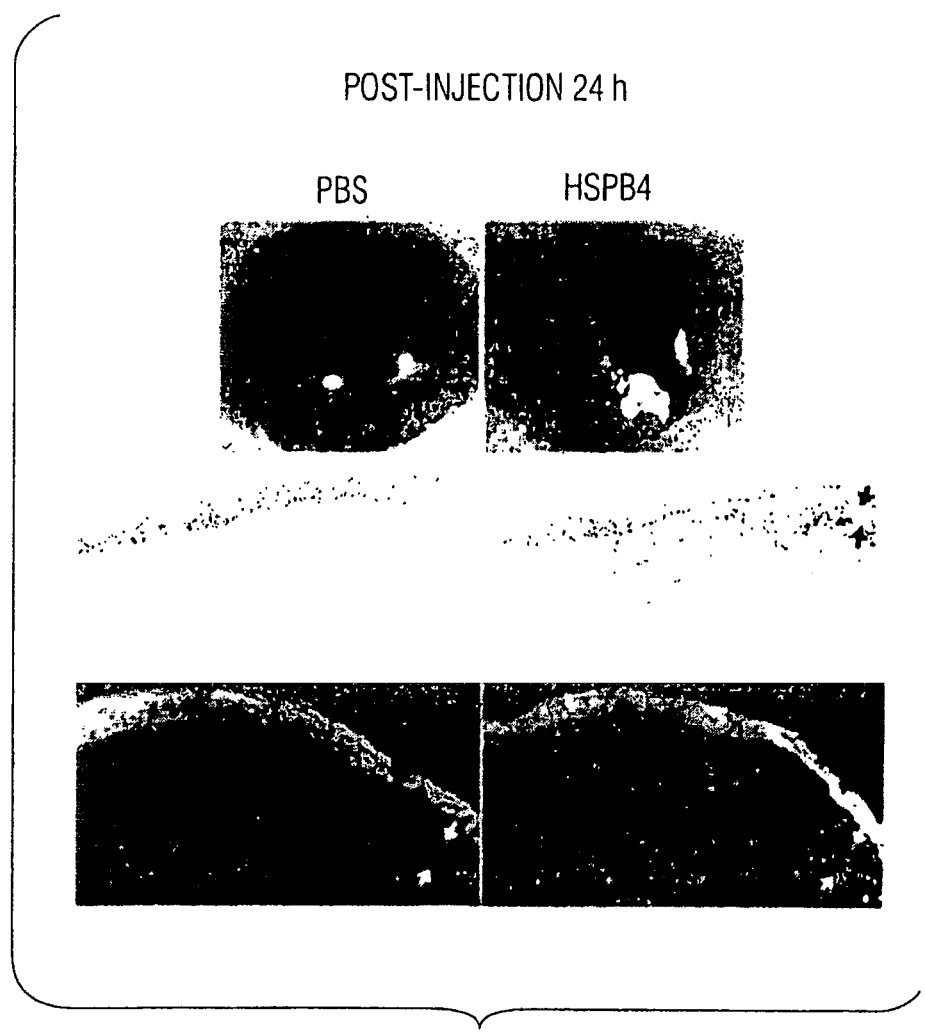
Figure 33D:
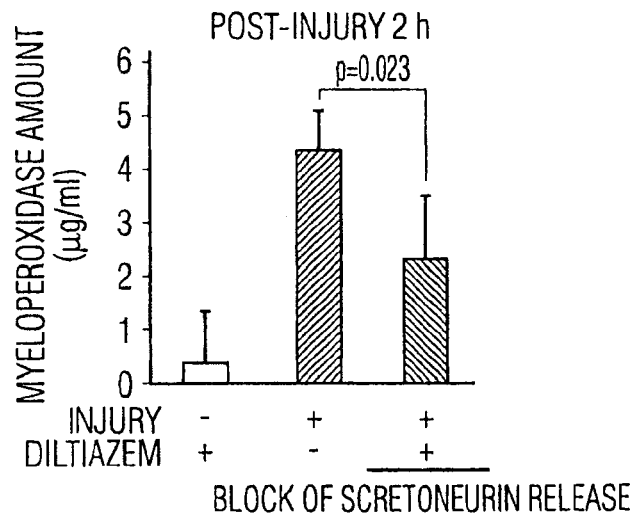
Figure 33E:
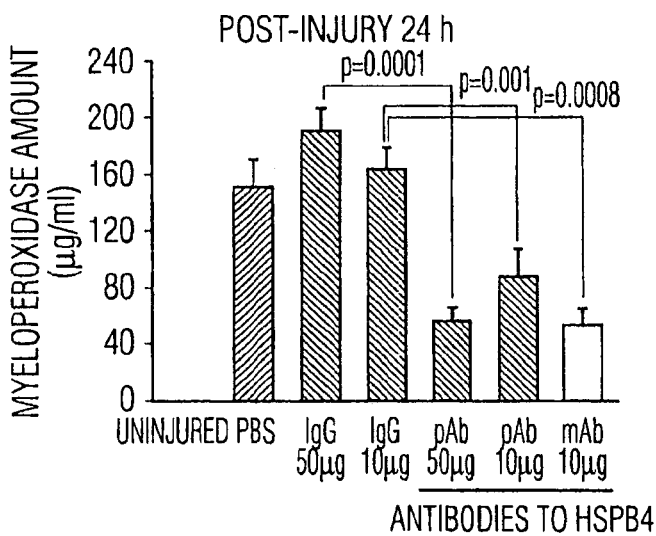
Figure 33F:
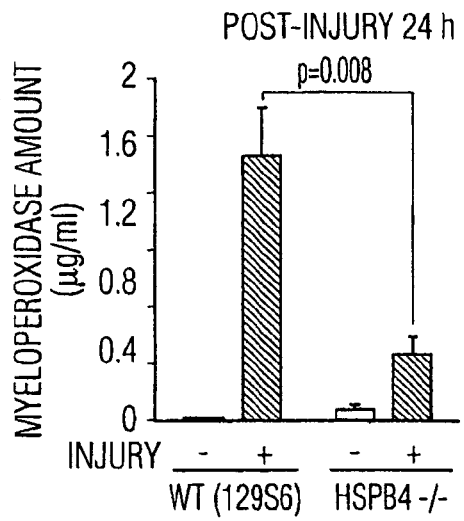

Injection of recombinant HSPB4 that was pyrogen-free (see Methods) stimulated the neutrophil infiltration of both Phase I and Phase II (FIGS. 33B and C). Reproduction of Phase I was explained apparently by the protein being injected earlier than it appears in the tissue after injury to the cornea (FIGS. 32E-H). Injection of recombinant HSPB4 into one region of the cornea also reproduced the opacity produced by sterile inflammation (FIG. 33C). The role of HSPB4 was confirmed by experiments in which antibodies to the protein were injected into the corneal stroma immediately after the injury (FIG. 33E). The antibodies to HSPB4 inhibited significantly the Phase II inflammatory response in the cornea after the injury. Also, the neutrophil infiltration of Phase II in the cornea after injury was decreased significantly in the corneas of HSPB4 knockout mice, compared to wild-type controls (FIG. 33F).

HSPB4 Activated Resident Macrophages Through TLR2/NF-kB Signaling.

Figure 33G:
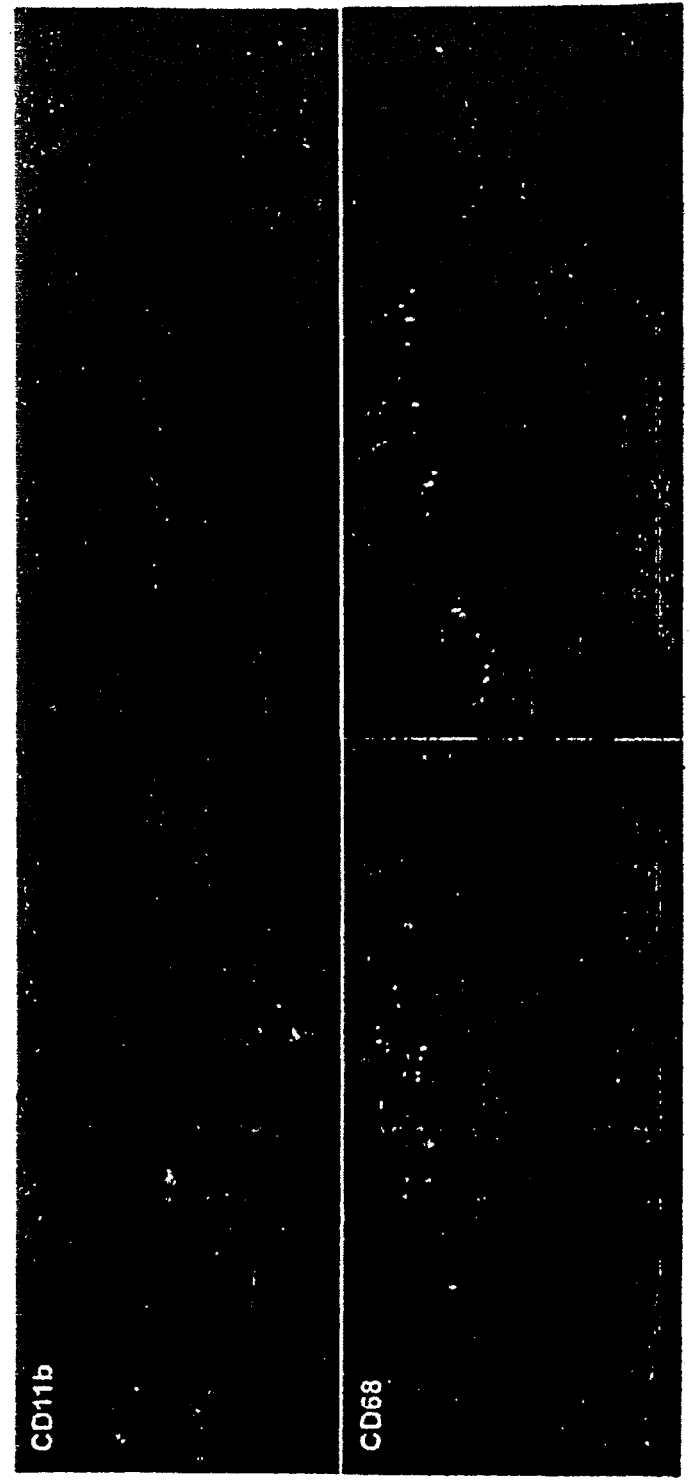
Figure 34A:
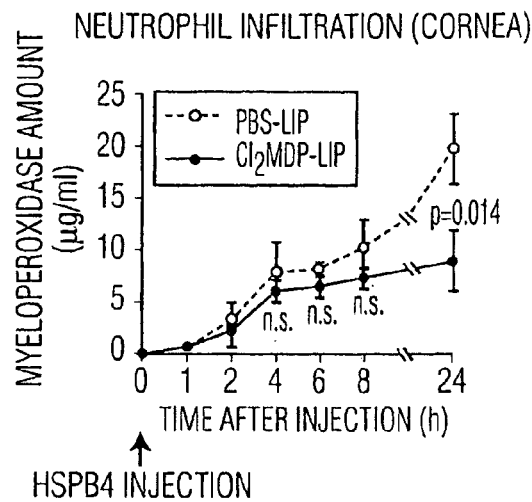
FIG. 34. HSPB4 activated macrophages through TLR2/NK-kB signaling. A. HSPB4 did not induce the Phase II response when corneal macrophages were depleted by subconjunctival injection of liposome-encapsulated clondronate ($Cl_2$MDP-LIP). B. An intracameral injection of TSG-6, an inhibitor of TLR2/NF-kB signaling, suppressed the Phase II inflammatory response of the cornea after injury. C. TSG-6 treatment also decreased significantly the neutrophil infiltration in Phase II in the cornea injected with HSPB4. D. Macrophages were activated to express pro-inflammatory cytokines when incubated with necrotic extracts of the cornea. Blocking HSPB4 with polyclonal (pAb) or monoclonal (mAb) antibodies negated significantly the effects of necrotic corneal extracts on macrophage activation. E. The addition of recombinant HSPB4 activated macrophages in culture in a dose-dependent manner. F. HSPB4 induced the translocation of NK-kB from the cytoplasm into nucleus in macrophages. G. Necrotic extracts of the cornea also stimulate the TLR2/NK-kB pathway in the reporter cell expressing TLR2 (HEK-TLR2), but antibodies to HSPB4 partially inhibited the effects. H, I, J. Recombinant HSPB4 stimulated NF-kB signaling in the cell line expressing TLR2 or TLR4 (HEK-TLR4) in a dose-dependent manner, while it had no effect in the cell without either receptor (HEK-null). K. Murine macrophages (RAW 264.7) were incubated with Group A molecules (HSPB4, HSPB5, or β-crystallin) and evaluated for expression of pro-inflammatory cytokines by real-time RT-PCR. Neither HSPB5 nor β-crystallin activated macrophages, while HSPB4 induced remarkably the expression of pro-inflammatory cytokines in macrophages. In contrast, heat-treated HSPB4 (boiling, 20 min) did not activate macrophages in culture, indicating that HSPB4, and not contaminating pyrogens, induced the macrophage activation. Human embryonic kidney cells expressing TLR-2 (HEK-TLR2) were incubated with HSPB5 or β-crystallin and evaluated for activation of NK-kB signaling. Neither HSPB5 nor β-crystallin activated TLR2/NK-kB signaling. L. Sterile injury was made to the rat cornea after resident macrophages were depleted by subconjunctival injections of clodronate-encapsulated liposome ($Cl_2$ MDP-LIP) on day −2 (2 days before injury) and day 0 (immediately after injury). The cornea was evaluated for neutrophil infiltration by assays for myeloperoxidase, hematoxylin-eosin (H&E) straining, and immunostaining for neutrophil elastase to identify neutrophils. Neutrophil infiltration measured by MPO was decreased markedly in the cornea 24 hours after injury by injection with clordronate-encapsulated liposome, compared to PBS-encapsulated liposome-injected controls (PBS-LIP). Infiltration of inflammatory cells and neutrophils also was decreased markedly in the macrophage-depleted cornea.
Figure 34B:
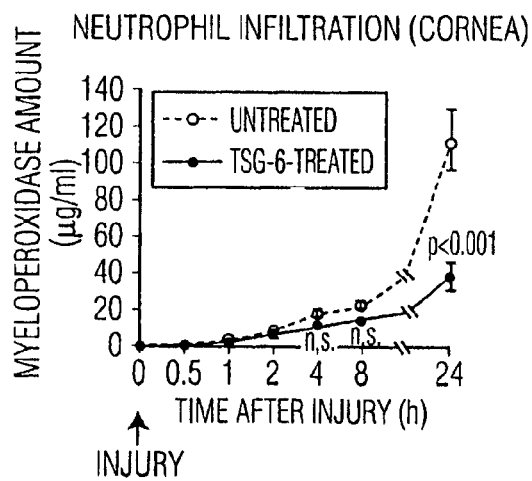
Figure 34C:
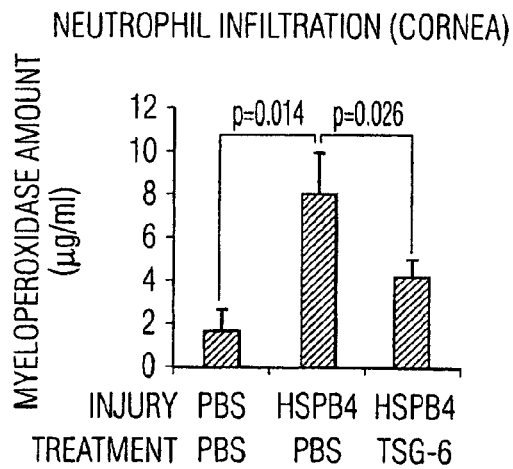

To identify the cells that responded to HSPB4 in the cornea, resident macrophages were depleted from the corneas of Lewis rats by injecting clodronate liposomes subconjunctivally, and then recombinant HSPB4 was injected into the corneal stromas. Macrophage depletion was confirmed with immunostaining for macrophage-specific markers CD68 and CD11b (FIG. 33G). The protein did not reproduce Phase II in rats in which macrophages were depleted (FIG. 34A), suggesting that the effects of HSPB4 were dependent on the presence of resident macrophages. Similarly, the inflammation was decreased markedly in the cornea after chemical/mechanical injury when resident macrophages were depleted prior to an injury (FIG. 34L), indicating a crucial role of resident macrophages in sterile injury-induced inflammation of the cornea. In parallel experiments, it was observed that neutrophil infiltration of Phase II, but not Phase I, was suppressed significantly by an intraocular injection of the anti-inflammatory protein, TSG-6 (FIG. 34B), that inhibits TLR2/NF-kB signaling in macrophages (Choi, *Blood*, in press; Lesley, et al., *J. Biol. Chem.*, Vol. 279, pgs. 25745-25754 (2004)). Also, TSG-6 suppressed significantly the Phase II inflammatory response caused by HSPB4 injection to the corneal stroma (FIG. 34C). The results suggested therefore that HSPB4 signaled Phase II by activating TLR2/NF-kB signaling in resident macrophages.

Figure 34D:
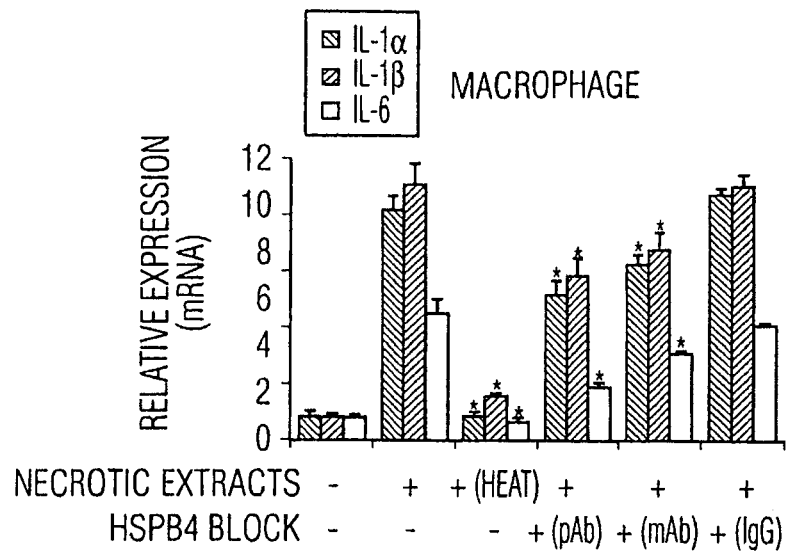
Figure 34E:
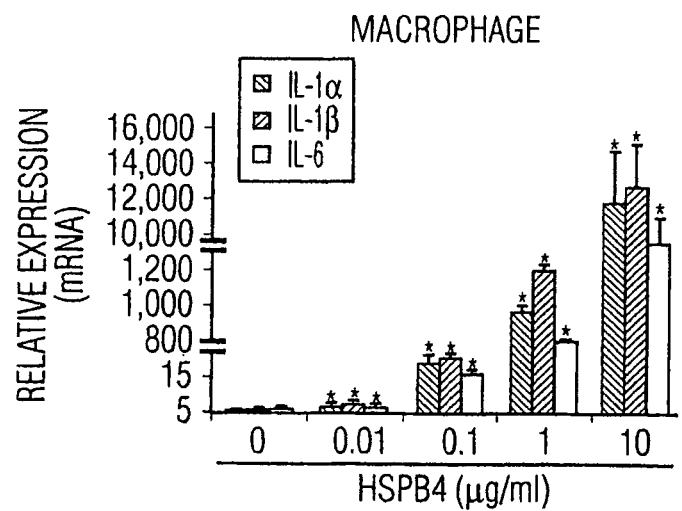
Figure 34F:
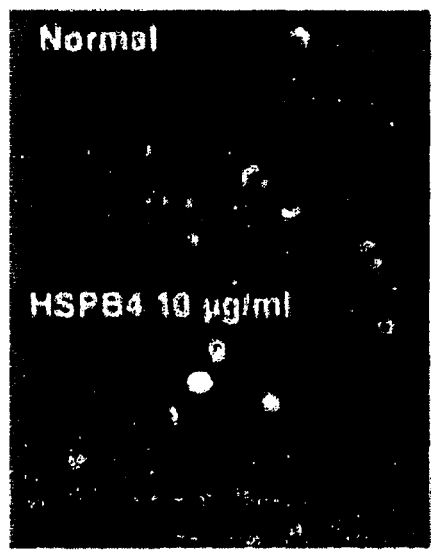
Figure 34G:
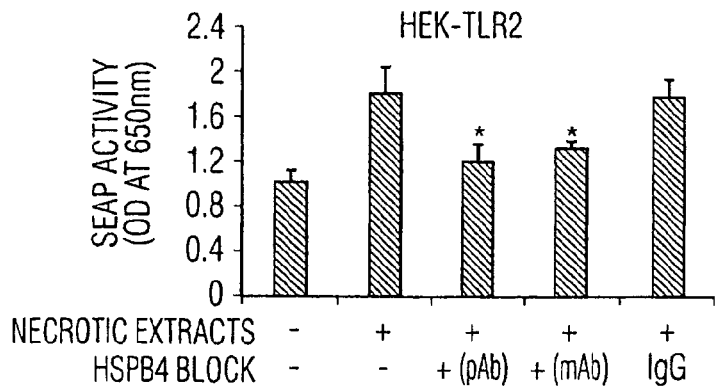
Figure 34H:
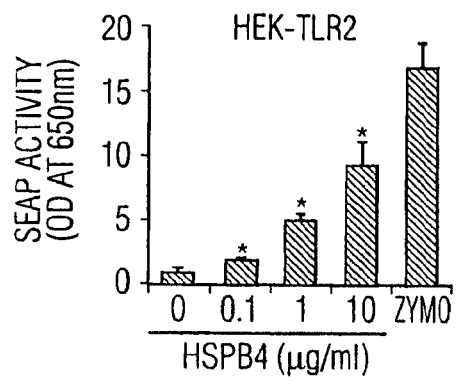
Figure 34I:
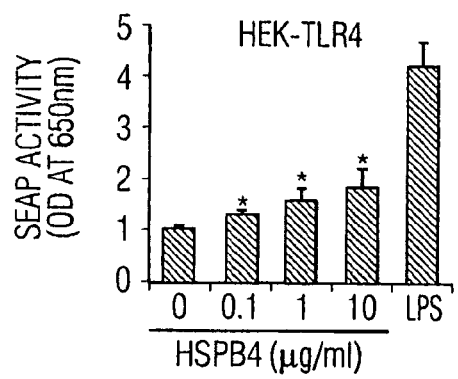
Figure 34J:
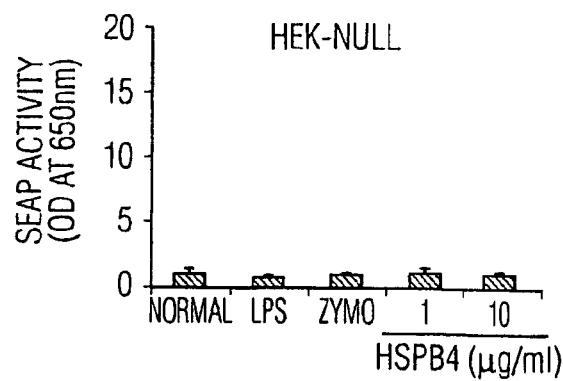
Figure 34K:
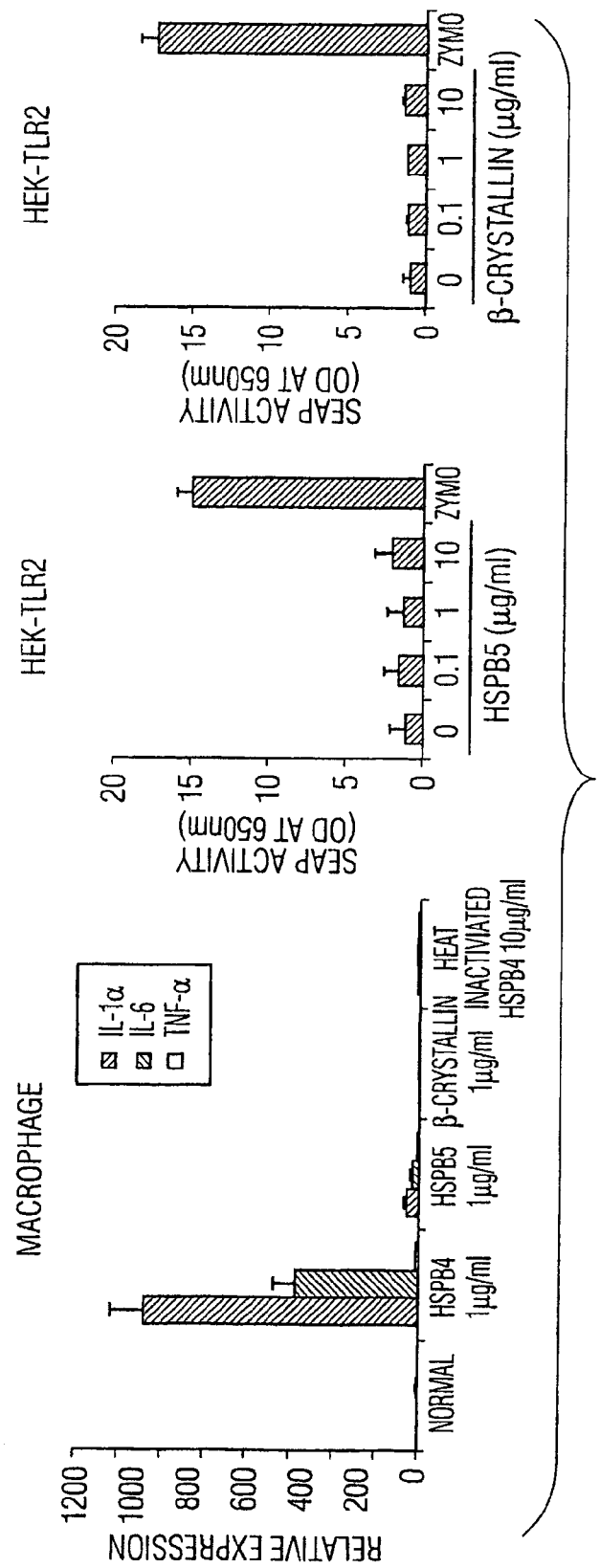
Figure 34L:
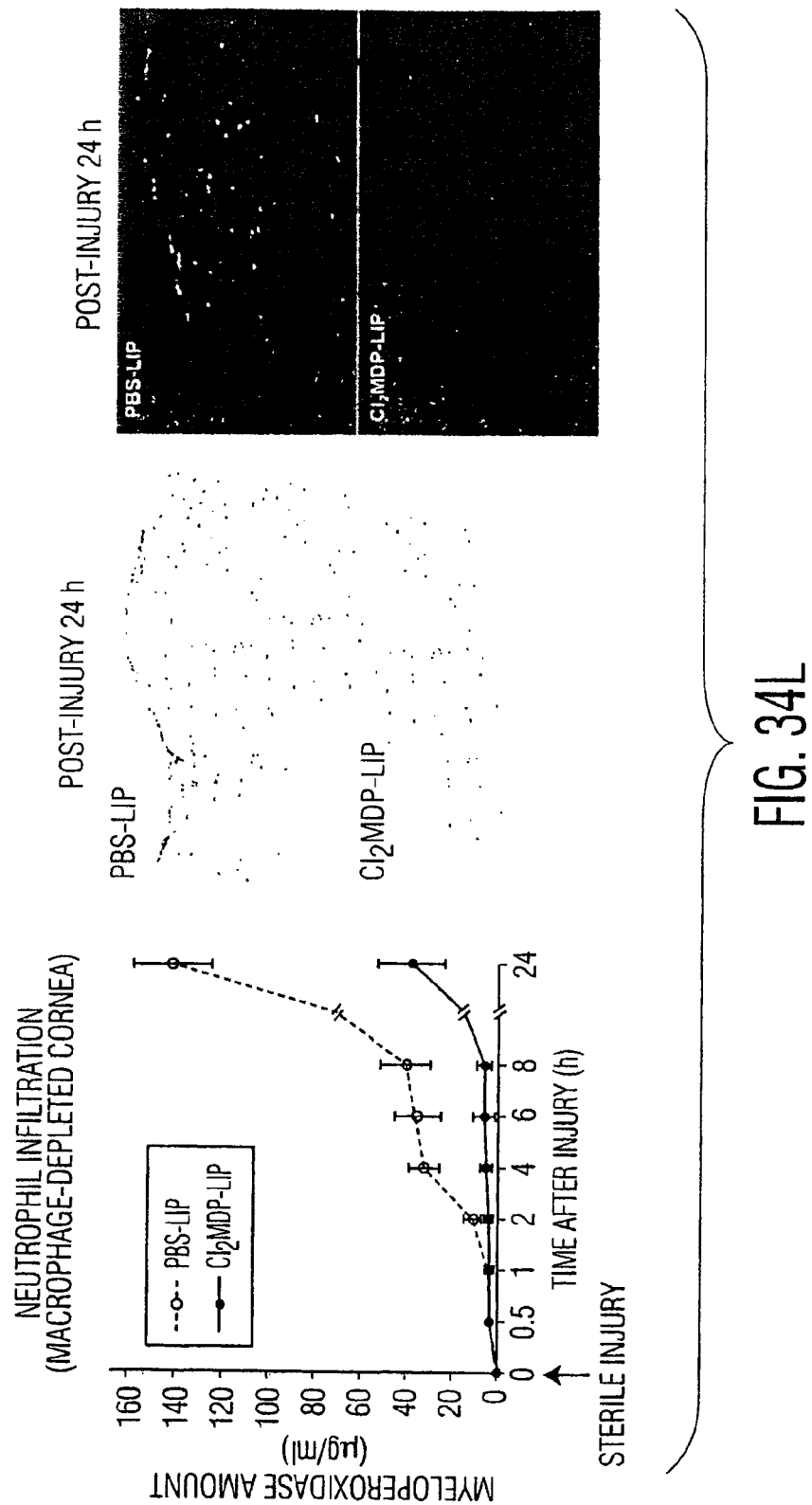
Figure 35A:
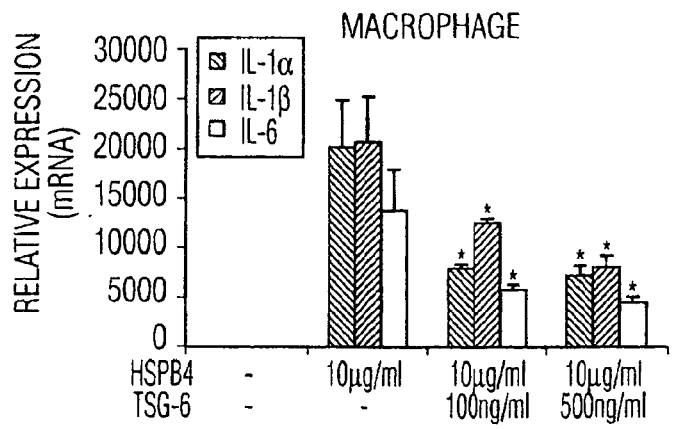
FIG. 35. TSG-6 suppressed HSPB4-induced activation in macrophages in a CD44-dependant manner. A, B. TSG-6 in a dose dependent manner suppressed the activation of macrophages by HSPB4. C, D. TSG-6 did not inhibit a HSPB4-mediated activation of NF-kB signaling in HEK-TLR2 cells which did not express CD44. However, after the cells were transfected to express CD44, TSG-6 dose-dependently inhibited HSPB4-mediated activation of NF-kB signaling. E. TSG-6 inhibited significantly the inflammation in the corneas of wild-type C57BL/6 mice, but it did not suppress inflammation in the corneas of CD44 knockout mice. F. Murine macrophages (RAW 264.7) were incubated with secretoneurin and evaluated for expression of pro-inflammatory cytokines by real time RT-PCR. Secretoneurin did not activate macrophages. Human keratocytes were cultured with either secretoneurin or HSPB4. Neither secretoneurin nor HSPB4 activated keratocytes to produce cytokines.
Figure 35B:
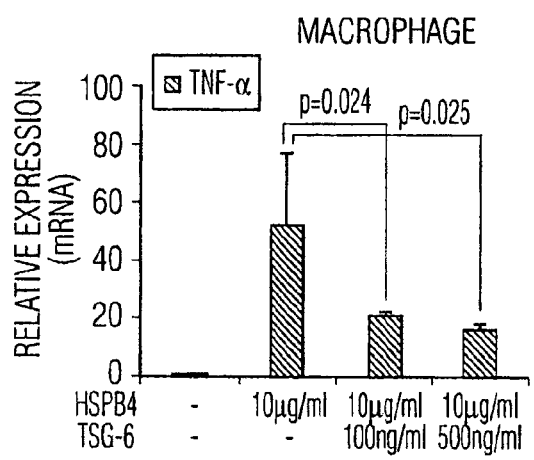
Figure 35C:
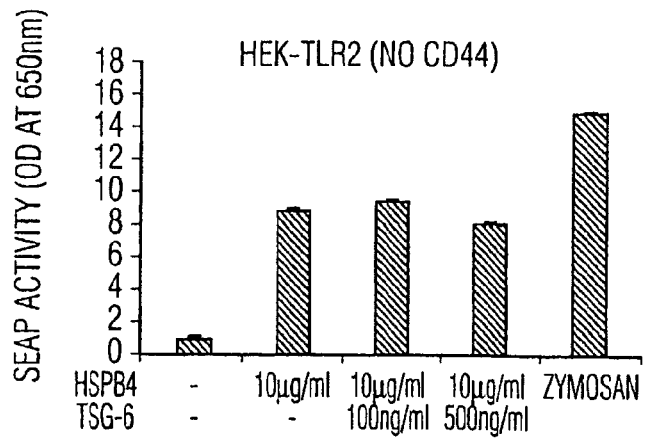
Figure 35D:
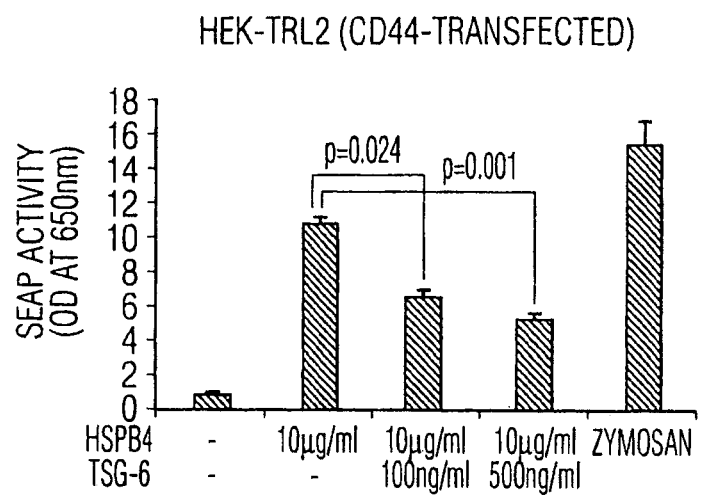
Figure 35E:
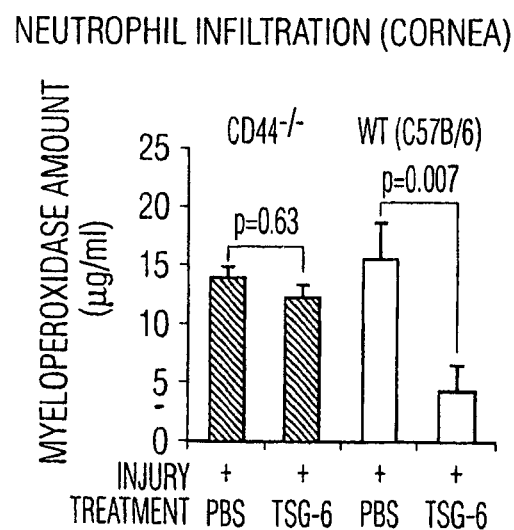
Figure 35F:
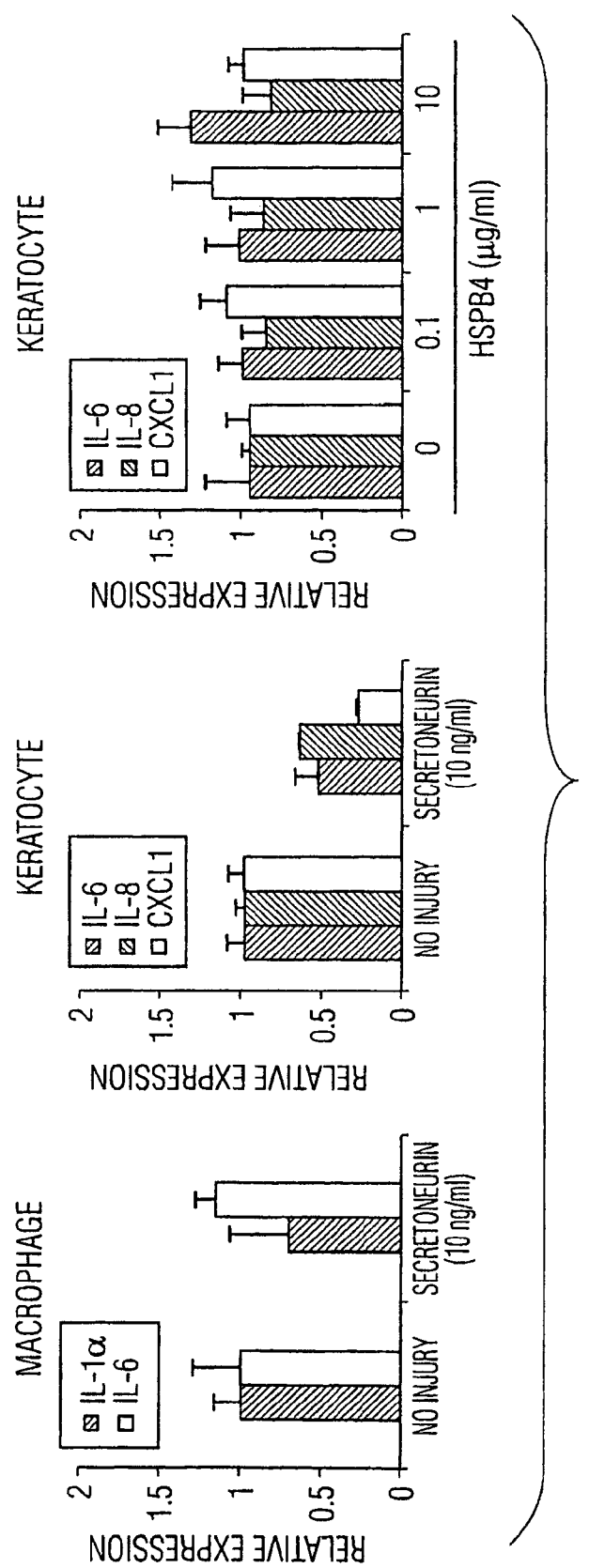

To test the effects of HSPB4 on macrophages, macrophages were incubated with extracts of necrotic corneas. The extracts increased the expression of the pro-inflammatory cytokines IL-1α, IL-1β, and IL-6 (FIG. 34D); however, heat inactivation of the extracts inhibited their effect, suggesting that the active factor(s) in the extracts was (were) protein(s). Addition of either a polyclonal or monoclonal antibody to HSPB4 suppressed significantly the effect of the necrotic extracts on macrophage activation, indicating that one of the active factors in necrotic corneal extracts was HSPB4 (FIG. 34D). In addition, recombinant HSPB4 increased the expression of the pro-inflammatory cytokines by macrophages in a dose-dependent manner (FIG. 34E). As expected, HSPB4 caused translocation to the nucleus of the NF-kB complex in macrophages (FIG. 34F). To test whether HSPB4 signaled through the TLR2/NF-kB pathway, a reporter cell line transduced was used to assay TLR2/NF-kB signaling (HEK-TLR2). Experiments in a HEK-TLR2 cell line demonstrated that the necrotic extracts of the cornea increased TLR2/NF-kB signaling and that antibodies to HSPB4 inhibited the effect (FIG. 34G). Recombinant HSPB4 stimulated NF-kB signaling in the same cell line in a dose-dependent manner (FIG. 34H). HSPB4 acted primarily through TLR2; it had a smaller effect in the reporter cell line that expressed TLR4 and no effect in the reporter cell without either receptor (FIGS. 34I and J); however, HSPB4 did not stimulate keratocytes in culture to express pro-inflammatory cytokines (FIG. 35F). Also, other Group A molecules such as HSPB5 and βB-crystallin had no effect on pro-inflammatory cytokine production in macrophages or on NF-KB activation in HEK-TLR2 cells (FIG. 34K). In addition, SN did not induce the expression of pro-inflammatory cytokines in either macrophages or keratocytes in vitro (FIG. 35F). Similarly, HSPB4 did not stimulate keratinocytes in culture to express pro-inflammatory cytokines. (FIG. 35F). Together, the results indicated that HSPB4 was a principal DAMP for Phase II and acted through the activation of resident macrophages in the cornea.

TSG-6 Suppressed HSPB4-induced Activation of Macrophages.

TSG-6 was shown previously to provide a potential therapy for chemical injuries of the cornea but its mechanism of action was not established (Oh, *Proc. Nat. Acad. Sci.*, 2010). Therefore, the hypothesis that TSG-6 inhibited the Phase II response, but not Phase I (FIGS. 34B and C) was tested by decreasing the HSPB4 induced activation of macrophages. Recombinant TSG-6 decreased expression of pro-inflammatory cytokines in macrophages stimulated by HSPB4 (FIGS. 35A and B). Because the protein was shown previously to inhibit TLR2/NFkB signaling in macrophages by interaction with CD44 (Choi, *Blood*, in press; Lesley J, Gal I, Mahoney D J, et al., TSG-6 modulates the interaction between hyaluronan and cell surface CD44. *J Biol Chem.*, 2004; 279:25745-25754). Whether the effects of TSG-6 were CD44-dependent also were examined. As expected, TSG-6 had no significant effect on NF-kB signaling in the HEK-TLR2 reported cell line unless the cell line were transduced to express CD44 (FIGS. 35C and D); however, TSG-6 had no effect on the parent cell line that did not express CD44. Also, TSG-6 had no effect the Phase II inflammatory response after chemical/mechanical injury to the cornea of CD44 knockout mice (FIG. 35E), indicating that the action of TSG-6 an macrophages was CD44-dependent.

Discussion

Figure 36:
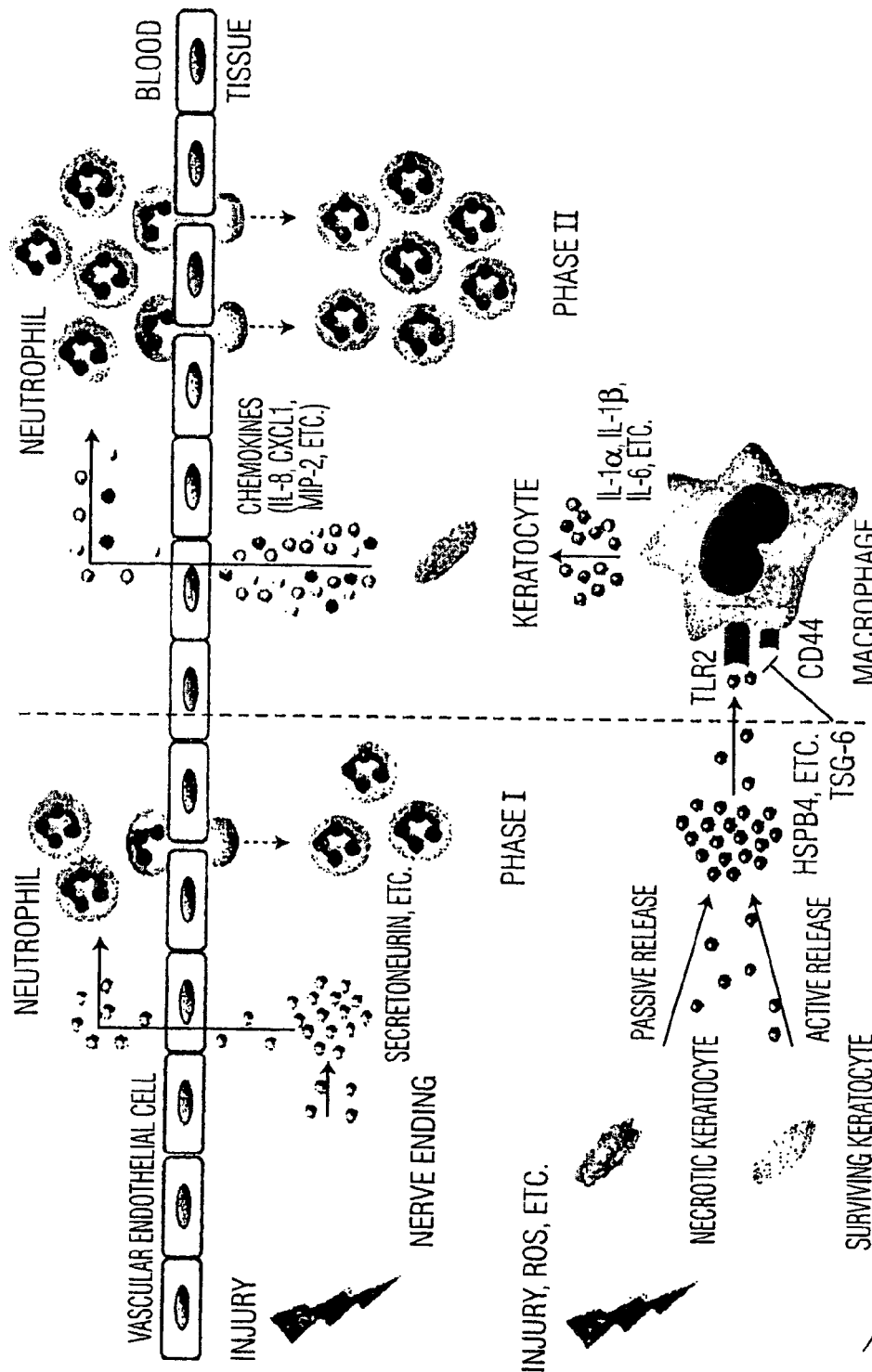
FIG. 36. The schematic diagram of sterile inflammation in the cornea. Immediately after injury, SN is released from nerve endings in the cornea and circulating neutrophils are recruited, thereby inducing the Phase I inflammatory response. In response to injury including oxidative stress, necrotic or injured keratocytes secrete HSPB4. The HSPB4 activates resident macrophages in the cornea via the TLR2/NF-kB signaling pathway to produce pro-inflammatory cytokines including IL-1 and IL-6. These injury signals are propagated rapidly and amplified by keratocyte activation to produce chemokines that induce neutrophil infiltration of Phase II. TSG-6 decreased neutrophil infiltration by inhibiting the initial step of macrophage activation via TLR2/CD44/NF-kB signaling.

As summarized in FIG. 36, the results here demonstrated that there were two distinct phases of neutrophil infiltration in the cornea after sterile injury: (a) a small initial Phase I that began within 15 min, and reached a plateau level in 4 to 8 hours, and (b) a much larger Phase II with a peak at 24 to 48 hours. In search for the stimuli for Phase I and II responses, the upregulated molecules after an injury were screened on the assumption that the molecules tissues actively produce after injury may be the major stimuli to induce sterile inflammation.

A major stimulus for the Phase I response was the neuropeptide SN. The Phase I response began within 15 min of the injury and, as indicated by the depletion experiments with clodronate, it did not require participation of macrophages. Neuropeptides are attractive candidates for Phase I stimuli because they are preformed and released rapidly from sensory nerve endings in response to injury. Also, the cornea is one of the most densely innervated tissues. Intrastromal injection of recombinant SN reproduced the Phase I response and an inhibitor of neuropeptide blocked the effect. As indicated by experiments with macrophage depletion, Phase I did not require participation of resident macrophages. SN did not elicit the further, intense infiltration of neutrophils in Phase II that was mediated by activation of resident macrophages. Therefore, the Phase I response was independent of the Phase II response.

Neuropeptides are attractive candidates for the stimuli of the initial inflammatory responses of the tissues because they are preformed and are released rapidly from nerve endings by injury. Neuropeptides may be important particularly in the response of the cornea to an injury because the cornea is one of the most heavily innervated tissues in the body. (Nishida, Cornea, $2^{nd}$ Edition (Krachmer, et al., eds.), pg. 4. (Elsevier Mosby, Philadelphia, 2005)). SN is a member of the granin family of neuropeptide/neurotransmitter, and it contributes to innate immunity by activating chemotactic migration and transendothelial extravasation of immune cells (Helle, 2010; Taupenot, 2003). Importantly, SN was shown to be as effective as TNF-α in stimulating transmigration of neutrophils through an endothelial cell barrier (Kahler, et al., Exp. Lung. Res., Vol. 27, No. 1, pgs. 25-46 (2001); Kahler, et al., Regul. Pept., Vol. 105, No. 1, pgs. 35-46 (2002). Also, recent in vivo studies suggest that SN has a role not only in neurogenic inflammation, but also a more complex role in common diseases, such as myocardial infarction, chronic heart failure, essential hypertension, rheumatoid diseases, or acute inflammatory bowel syndromes than appreciated previously (Helle, 2010; Taupenot, 2003; Wiedermann, Peptides, Vol. 21, No. 8, pgs. 1289-1298 (2000).

The data demonstrated that the principal DAMP for the Phase II response was the small heat shock protein HSPB4. The recombinant HSPB4 protein free of pyrogens reproduced the Phase II response by activating resident macrophages via the TLR2 NF-KB signaling pathway. The role of HSPB4 was confirmed by the observation that the Phase II response in injured cornea was diminished greatly by injection of blocking antibodies to HSPB4. Injury to the cornea released HSPB4 extracellularly. Addition of necrotic extracts from corneal tissues increased the synthesis of HSPB4 by stromal keratocytes, probably as a result of increased ROS and other stimuli in the necrotic cornea. Moreover, HSPB4 stimulated the TLR2/NF-KB signaling in macrophages to release a cascade of pro-inflammatory cytokines such as IL-1α and IL-1β.

The role of HSPB4 as a DAMP is consistent with previous observations with the protein and other heat shock proteins such as HSP60, 70, 72, or 96. (Lehnardt, et al. J. Neurosci; Vol. 28, pgs. 2320-2331 (2008); Asea, et al., Nat. Med., Vol. 6, pgs. 435-442 (2000); Wheeler, et al.; Respir. Res., Vol. 10, pgs. 31-43 (2009). Huang, et al., J. Immunol., Vol. 182, pgs 4965-4973 (2009); Chen, et al., Eur. J. Immunol., Vol. 40, pgs. 1541-1544 (2010)). HSPB4 is a member of small molecular weight heat shock proteins (sHSPs) that range in size from 15-30 kDa. Like other heat shock proteins, sHSPs are induced by heat and other stimuli such as oxidative and inflammatory stresses, and they act as a chaperones to protect cells from damage produced by misfolded proteins. However, HSPs have paradoxical effects. (Kobba, et al., Shock, Dec. 9, 2010 online publication; DeMeester, et al., FASEB J., Vol. 15, pgs. 270-274 (2000); Chen, et al., Inflamm. Allergy Drug Targets, Vol. 6, pgs. 91-100 (2007)). Heat shock pre-treatment induces intracellular HSPs to protect against inflammation (Ousman, et al., Nature, Vol. 448, pgs. 474-479 (2007); Saraswathy, et al., Invest. Ophtalmol. Vis. Sci., Vol. 51, No. 7, pgs. 3680-3686 (2010); Munemasa, et al., Invest. Ophthalmol. Vis. Sci., Vol. 50, No. 8, pgs. 3869-3875 (2009), whereas after inflammatory injury has been primed or cell integrity has been compromised, heat shock induces expression of HSPs that are released from damaged or stressed cells and exacerbates cell injury (Asea, et al., Nat. Med., Vol. 6, No. 4, pgs. 435-442 (2000); Quintana, et al. J. Immunol., Vol. 175, No. 5, pgs. 2777-2782 (2005); Lehnardt, et al., J. Neurosci, Vol. 28, No. 10, pgs. 2320-2331 (2008); Huang, et al., J. Immunol., Vol. 182, No. 8, pgs. 4965-4973 (2009); Wheeler, et al., Respir. Res., Vol. 10, pg. 31 (2009). Furthermore, HSPs are known to function as an endogenous adjuvant to facilitate the binding of other danger signals to immune cells and thus to enhance the immunogenicity. (Chen, et al., Eur. J. Immunol., Vol. 40, pgs. 1541-1544 (2010)). Consistent with these reports, it now is reported that a small HSP, HSPB4, stimulated macrophages in vitro through the TLR2/NF-kB pathway and acted as the principal DAMP for the Phase II inflammatory response in the injured cornea. On the other hand, another small HSP, HSPB5, did not induce this response.

The identification of HSPB4 as the principal DAMP for the Phase II inflammatory response has several implications for potential therapies. One is that the results provide an explanation for the beneficial effects observed previously with applications of TSG-6 following chemical injury to the cornea (Oh, 2010). TSG-6 interacts with CD44 on macrophages and decreases thereby the HSPB4 induced TLR2/NFkB signaling that has been induced by HSPB4 released from injured cornea. (Choi, in press).

Another implication is that antibodies or antagonists to HSPB4 might serve as a therapy alone or in combination with TSG-6 to modulate or prevent sterile inflammation of the cornea. (Oh, 2010). Still another implication is that the results may provide a guide to developing therapies for other diseases of the eye or of nonocular tissues. HSPB4 was shown to be expressed and upregulated in the retina in models for uveitis (Sarawathy, et al., Invest. Ophthalmal. Vis-Sci., Vol. 51, pgs. 3680-3686 (2010); Rao, et al., Invest. Ophthalmol. Vis. Sci., Vol. 49, pgs. 1161-1171 (2008)), glaucoma (Munemasa, et al., Invest. Ophthalmol. Vis. Sci., Vol. 50, pgs. 3869-3875 (2009)), age-related macular degeneration (Kapphahn, et al., Biochemistry, Vol. 42, pgs. 15310-15325 (2003)), and hypoxic retinopathy (Miyara, et al., Jpn. J. Ophthalmol., Vol. 52, pgs. 84-90 (2008)). HSPB4 also is known to be expressed in nonocular tissues such as spleen, thymus, pancreas, and kidney. (Deng, et al., Biochem. Biophys. Acta, Vol. 1802, pgs. 621-631 (2010); Srinivasan, et al., J. Biol. Chem., Vol. 267, pgs. 23337-23341 (1992)). Because sterile inflammation contributes to the pathogenesis of many diseases (Chen, et al. Nat. Rev. Immunol., Vol. 10, pgs. 826-837 (2010); Rock, et al., Ann. Rev. Immunol., Vol. 28, pgs. 321-342 (2010); Spite, et al., Circ. Res., Vol. 107, pgs. 1170-1184 (2010)), the strategy of modulating the activities of HSPs or related receptors using TSG-6 or antibodies or antagonists to extracellular HSPs may present useful drug targets to treat a variety of inflammatory diseases where HSPs are the primary signals for inflammation, such as ischemia-reperfusion injury, acute lung injury, various kidney diseases, atherosclerosis, obesity, and diabetes. (Gill, et al., Free Radic. Biol. Med., Vol. 48, pgs. 1121-1132 (2010)).

The disclosures of each and every patent, patent application, publication, database accession number, and depository accession number cited herein are hereby incorporated herein by reference in their entirety to the same extent as if each patent, patent application, publication, database accession number, and depository accession number were incorporated individually by reference.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

REFERENCES

Aggarwal et al., 2005, Blood 105:1815-22
Akiyama et al., 2002, Glia 39(3): 229-36
Armstrong et al., 1998, Angiogenesis. 2(1):93-104.
Avila et al., 2001, Cornea 20:414-20
Block et al., 2009, Stem Cells 27(3):670-81
Callaghan et al., 2001, Rheumatology (Oxford) 46:105-11
Caplan, 1990, Biomaterials 11:44-6
Caplan et al., 2005, Tissue Eng 11:1198-1211
Caplan et al., 2006, J Cell Biochem 98(5):1076-84
Castro-Malaspina et al., 1980, Blood 1980 56(2):289-301
Cauchi et al., 2008, Am J Ophthalmol 146:251-9
Cho et al, 1998, Cornea 17:68-73
Chen et al., 2006, Immunol Cell Biol 84:413-21
Clegg et al., 2006, Ophthalmic Epidemiol 13:263-74
D'Amato et al., 1994, Proc Natl Acad Sci USA 91:4082-5
Daya et al., 2005, Ophthalmology 112:470-7
De Ban et al., 2003. J Cell Biol 160(6) 909-18
Dooner et al., 2004, Blood Cells Mal Dis 32(1):47-51
Eaves et lt., 2001, Ann N Y Acad Sci 938:63-70, discussion 70-1
Espana et al., 2003, Br J Ophthalmol 87:1509-14
Fantes et al., 1990, Arch Ophthalmol 108:665-75
Foster C S, Letko E, Ba-Abbad R A Stevens-Johnson Syndrome [Internet] [updated 2007 Dec. 18, cited 2008 Mar. 7] Available from http://emedicine.medscape.com/article/1197450-overview
Fukuda et al., 2006, Circ Res 98(8): 1002-13
Gao et al., 2001, Cells Tissues Organs 169(1):12-20
Gerdoni et al., 2007, Ann Neurol 61(3):219-27
Guilak et al., 2004, Biorheology 41(3-4):389-99
Gupta et al., 2007, J Immunol 179(3):1855-63
Hogg et al., 1994, J Appl Physiol 77(4): 1795-800
Homma et al., 2004, Invest Ophthalmol Vis Sci 45:4320-6
Horwitz et al., 2002, Proc Natl Acad Sci USA 99(13):8932-7
Horwitz et al., 1999, Nat Med 5:309-13
Ilari et al., 2002, Ophthalmology 109:1278-84
Iso, et a]., 2007, Biochem Biophys Res Commun 354:700-6
Javazon et al., 2001, Stem Cells 19:219-25
Jenkins et al., 1993, Eye 7:629-33
Kim et al., 2006, Brain Res 1123(1):27-33
Koc et al., 2002, Bone Marrow Transplant 30:215-22
Krampera et al., 2007, Bone 40(2):382-90
Kuznetsov et al., 2001, J Cell Biol 153(5):1133-40
Le Blanc et al., 2007, J Intern Med 262(5):509-25
Lee et al., 2006, Proc Natl Acad Sci USA 103:17438-43
Lee et al., 2009, Cell Stem Cell 5:54-63
Limb et al., 2008, Br Med Bull 85:47-61
MacDonald et al., 2002, Bioessays 24(10):885-93
Mareschi et al., 2006, Exp Hematol 34(11) 1563-72
Melsaether C, Rosen CL Burns. Ocular [Internet] [updated 2009 Aug. 12] Available from http://emedicine.medscape.com/article/798696-overview
Mertzants et al., 2005, Invest Ophthalmol Vis Sci 46:46-50
Mets et al., 1981, Mech Ageing Dev 16(1):81-9
Mitjanovic et al., 2007, Am J Ophthalmol 143:409-15
Milner et al., 2003, J Cell Sci 116:1863-73
Milner et al., 2006, Biochem Soc Trans 34:446-50
Mishra, 2008, J Cardiovasc Med (Hagerstown) 9(2):122-8
Moss et al, 2000, Arch Ophthatmol 118:1264-8
Moss et al., 2008, Optom Vis Sci 85:668-74
Munoz et al., 2005, Proc Natl Acad Sci USA 102:18171-6
Nomura et al., 2005, Neuroscience 136(1):16t-9
Oh et al., 2008, Stem Cells 26:1047-55
Oh et al., 2009b, Curr Eye Res 34(2):85-91
Oh et al., 2009a, Cytokine 46(1)100-3
Ohtaki et al., 2008, Proc Natl Acad Sci USA 105:14638-43
Ortiz et al., 2007, Proc Natl Acad Sci USA 104:11002-7
Owen et al., Ciba Found Symp 136:42-60
Penolazzi et al., 2008, Cell Biol Int 32:320-5
Pereira et al., 1998, Proc Natl Acad Sci USA 95(3):! 142-7
Pflugfetder et al., 2008, Am J Manag Care 14:S102-S 106
Piersma et al., 1983, Br J Haematol 54(2):285-90
Prockop, 1985, J Clin Invest 75(3):783-7
Prockop et al., 1995, Annu Rev Biochem 64:403-34
Prockop, 1997, Science 276:71-4
Prockop et al., 2003, Proc Natl Acad Sci USA 100; 119 17-23
Prockop, 2007, Clin Pharmacol Ther 82:241-3
Prockop, 2009, Mol Ther 17:939-46
Rao et al., 1999, Ophthalmology 106:822-8
Reddy et al., 2004, Cornea 23:751-61
Ren et al., 2008, Cell Stem Cell 0.2:141-50
Reinhard et al., 2004, Ophthalmology 111:775-82
Ringden et al., 2006, Transplantation 81:1390-7
Rosada et al., 2003, Calcif Tissue 72(2):135-42
Schaumberg et al., 2003, Am J Ophthalmol 136:318-26
Schinkothe et al, 2008, Stem Cells Dev 17:199-206
Schrepfer et al., 2007, Transplant Proc 39(2) 573-6
Seo et al., 2005, J Dent Res 2005 84(10):907-12
Sharpe et al., 2007, Tissue Eng 13:123-32
Shi et al., 2008, Clin Exp Ophthalmol 36:501-7
Shorn et al., 2007. Surv Ophthalmol 52:483-502
Solomon et al., 2002, Ophthalmology 109:1159-66
Spees et al, 2006, Proc Natl Acad Sci USA 103(5):1283-8
Tang et al., 2007, Cell Transplant 16(2)159-69
Ti et al., 2002, Invest Ophthalmol Vis Sci 43:2584-92
Tseng et al., 1998, Arch Ophthalmol 116:431-41
Tsubota et al, 1999 N Engl J Med 340:1697-703
Ueno et al., 2007, Cornea 26:1220-7
Wakitani et al., 1995, Muscle Nerve 18(12): 1417-26
Wisniewski et al, 2004, Cytokine Growth Factor Rev 15: 129-46
Woodbury et al., 2000, J Neurosci Res 61(4):364-70
Wu et al, 2008, Cell Transplant 16(10):993-1005
Zacharek et al., 2007, J Cereb Blood Flow Metab 27:1684-91

What is claimed is:

1. A method of treating dry eye syndrome in a patient, comprising:
administering to said patient a therapeutic agent comprising TSG-6 protein or a biologically active fragment, or variant thereof, wherein said TSG-6 protein or biologically active fragment, or variant thereof, is administered in an amount effective to treat said dry eye syndrome in said patient.

2. The method of claim 1 wherein said TSG-6 protein or a biologically active fragment, or variant thereof, is administered to said patient in an amount of from about 0.01 mg to about 20 mg per kilogram of body weight.

3. The method of claim 2 wherein said TSG-6 protein or a biologically active fragment, or variant thereof, is administered to said patient in an amount of from about 0.1 mg to about 5 mg per kilogram of body weight.

4. The method of claim 1 wherein said therapeutic agent is administered intraocularly.

5. A method of treating dry eye syndrome in a patient, comprising:
   administering to the eye of said patient eye drops containing a therapeutic agent comprising TSG-6 protein or a biologically active fragment, or variant thereof, and wherein said TSG-6 protein or biologically active fragment, or variant thereof, is contained in said eye drops in an amount effective to treat said dry eye syndrome in said patient.

* * * * *